United States Patent [19]

Sugihara et al.

[11] 4,035,512
[45] July 12, 1977

[54] AMINOTETRALOLS

[75] Inventors: Hirosada Sugihara, Osaka; Masazumi Watanabe, Takatsuki; Michio Motohashi, Kobe; Masao Nishikawa, Nagaokakyo; Yasushi Sanno, Ikeda, all of Japan

[73] Assignee: Takeda Chemical Industries, Ltd., Osaka, Japan

[21] Appl. No.: 586,282

[22] Filed: June 12, 1975

[51] Int. Cl.² .............. A61K 31/13; A61K 31/205; A61K 31/24; C07C 91/42

[52] U.S. Cl. ............. 424/330; 260/327 R; 260/335; 260/345.9; 260/347.7; 260/456 A; 260/457; 260/463; 260/476 C; 260/479 C; 260/479 R; 260/479 S; 260/486 R; 260/487; 260/488 C; 260/488 D; 260/501.18; 260/501.19; 260/570.5 P; 260/570.7; 260/570.8 R; 260/570.9; 260/573; 260/574; 260/575; 260/934; 424/275; 424/283; 424/285; 424/303; 424/308; 424/311; 424/316

[58] Field of Search .......... 260/456 A, 463, 476 C, 260/479 R, 501.18, 501.19, 570.5 P, 570.7, 570.8 R, 570.9, 573, 574, 575

[56] References Cited

U.S. PATENT DOCUMENTS 2,549,684  4/1951  Heinzelmann ............... 260/570.5
3,458,577  7/1969  Galantay ..................... 260/571
3,930,022  12/1975  Hauck et al. .................. 260/574

OTHER PUBLICATIONS

Chiemprasert et al., Ann. Chem., Band 685, pp. 141–148 (1965).

Primary Examiner—Dolph H. Torrence
Attorney, Agent, or Firm—Wenderoth, Lind & Ponack

[57] ABSTRACT

Novel aminotetralol compounds of the formula

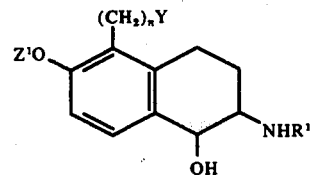

wherein $R^1$ is hydrogen, acyl derived from carboxylic acid, or a hydrocarbon group which may be substituted; $-OZ^1$ is hydroxyl which may be protected; Y is hydrogen, acyl, hydroxyl which may be protected, amino which may be substituted, nitro, cyano or halogen; and $n$ is zero, 1 or 2 with a proviso that when Y is hydrogen or hydroxyl which may be protected, $n$ is not zero, and their salts, have excellent pharmacological activities such as strong bronchodilating activity. They are useful as medicines, for example, for treatment of asthma.

49 Claims, No Drawings

AMINOTETRALOLS

The present invention relates to novel and useful aminotetralol compounds. More particularly, the present invention relates to novel aminotetralol compounds of the formula

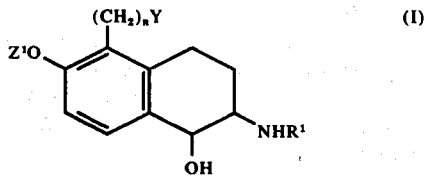

wherein $R^1$ is hydrogen, acyl derived from carboxyic acid, or a hydrocarbon group which may be substituted, $-OZ^1$ is hydroxyl which may be protected, Y is hydrogen, acyl, hydroxyl which may be protected, amino which may be substituted, nitro, cyano or halogen, and n is zero, 1 or 2 with a proviso that when Y is hydrogen or hydroxyl which may be protected, n is not zero, and their salts which have excellent pharmacological activities such as strong bronchodilating activity, and which are useful as medicines, for example, for treatment of asthma.

As medicines for the treatment of asthma, isoproterenol and metaproterenol, both of which have a stimulating action of β-adrenergic receptors, have been widely employed. However, while isoproterenol has a bronchodilator action which is said to be associated with $β_2$-adrenergic receptors, it has potent side effects due to its strong cardiac stimulation which is said to be associated with $β_1$-adrenergic receptors; metaproterenol on the other hand has only moderate side effects of the above type but is decidedly inferior in bronchodilator activity. Therefore, neither of them has been thought to be satisfactory as a selective bronchodilator.

The above situation provided an impetus to our intensive research, which has led us to success in synthesizing the novel compound (I), which has strong bronchodilator activity and, yet, has only moderate, or is substantially devoid of, side effects caused by $β_1$-adrenergic stimulation.

Thus, the principal object of the present invention is to provide the compound (I) and its physiologically acceptable salts, which are useful as medicines for treatment of asthma. Another object of the present invention is to provide processes for producing the novel and useful compound (I) and its salts. A further object is to provide an advantageous intermediate for producing the said compound (I). Other objects will be made clear from the description and claims hereinafter.

Referring, now, to the formula (I), the hydrocarbon group which may be substituted, designated by symbol $R^1$, may be acyclic or cyclic. The acyclic hydrocarbon group may be saturated or unsaturated, and straight-chain or branched, thus being exemplified by lower alkyl, advantageously of up to six carbon atoms (e.g. methyl, ethyl, n-propyl, i-propyl, n-butyl, i-butyl, t-butyl, sec-butyl, n-pentyl, 1-ethylpropyl, 1,2-dimethylpropyl, i-pentyl, t-pentyl, n-hexyl, i-hexyl, 2-methylpentyl, 1-methylpentyl, 1,3-dimethylbutyl, etc.), lower alkenyl, advantageously of up to six carbon atoms (e.g. ethenyl, propenyl, butenyl, pentenyl, hexenyl, methylpropenyl, ethylpentenyl, ethylhexenyl, etc.), lower alkynyl, advantageously of up to six carbon atoms (e.g. ethynyl, propynyl, butynyl, pentynyl, hexynyl, etc.) and so on. Among them more advantageous is lower alkyl branching at the α-position to the amino group of the formula (I), especially of up to four carbon atoms, such as i-propyl, 1-methylpropyl and t-butyl. As the substituent or substituents on the aforementioned acyclic hydrocarbon group which may be substituted, there may be mentioned, among others, cycloalkyl, advantageously of 3 to 7 membered-ring (e.g. cyclopropyl, cyclobutyl, cyclopentyl, cyclohexyl, cycloheptyl, etc.), cycloalkenyl, advantageously of 3 to 7 membered-ring (e.g. 2-cyclopentenyl, 3-cyclohexenyl, etc.), a cycloalkylidene group advantageously of 3 to 6 membered-ring (e.g. cyclohexylidene, cyclopentylidene, etc.), aryl (e.g. phenyl, naphthyl, etc.), a heterocyclic group (for example, a heterocyclic group containing one oxygen (e.g. tetrahydrofuryl, tetrahydropyranyl, dihydropyranyl, furyl, etc.), a heterocyclic group containing one nitrogen (e.g. piperidyl, pyridyl, indolyl, quinolyl, etc.), a heterocyclic group containing one sulfur (e.g. thienyl, tetrahydrothienyl, etc.), a heterocyclic group containing two or more and same or different heteroatoms (e.g. thiazolyl, pyrimidyl, oxazolyl, etc.), etc.), hydroxyl, lower alkoxy of 1 to 4 carbon atoms (e.g. methoxy, ethoxy, propoxy, etc.), aryloxy (e.g. phenoxy, naphthoxy, etc.), halogen (e.g. chlorine, fluorine, bromine, iodine, etc.), esterified hydroxyl, lower alkoxycarbonyl group, acyl derived from a carboxylic acid (e.g. acetyl, propionyl, butyryl, benzoyl, etc.), amino or substituted amino (where the substituent or substituents may be alkyl, acryl or other groups), nitro, cyano and other groups. The aforementioned cycloalkyl, cycloalkenyl, aryl and heterocyclic groups may further contain appropriate substituent or substituents such as lower alkyl of 1 to 4 carbon atoms (e.g. methyl, ethyl, propyl, etc.), hydroxyl, lower alkoxy of 1 to 4 carbon atoms (e.g. methoxy, ethoxy, propoxy, etc.), halogen (e.g. chlorine, bromine, iodine, fluorine). Among typical examples of the aforementioned substituted acyclic hydrocarbon group are cyclohexylmethyl, 1-cyclohexylethyl, 2-cyclopentylethyl, 3-cyclohexyl-1-methylpropyl, 4-methylcyclohexylmethyl, 1-cyclohexenylmethyl, 1-cyclopentenylmethyl, benzyl, 4-methoxybenzyl, 4-hydroxybenzyl, α-methylbenzyl, 3,4-dimethoxybenzyl, α-methylphenethyl, 4-methoxy-α-methylphenethyl, 4-hydroxy-α-methylphenethyl, 4-hydroxy-α,α-dimethylphenethyl, 4-methoxy-α,α-dimethylphenethyl, 4-chlorophenethyl, 3-phenylpropyl, phenethyl, 4-methoxyphenethyl, 2-phenylpropyl, α,4-dimethylphenethyl, 1-methyl-2-cyclohexylidenethyl, tetrahydropyran-2-ylmethyl, 2,3-dihydropyran-2-ylmethyl, tetrahydrofuran-2-ylmethyl, 2-(furan-2-yl)-1-methylethyl, 2-thienylmethyl, piperidin-2-ylmethyl, 2-(2-indolyl)-1-methylethyl, 2-pyridylmethyl, 2-(2-thiazolyl)ethyl, 2-hydroxyethyl, 2-methoxyethyl, 3-ethoxy-1-methylpropyl, 6-methoxyhexyl, 1-methyl-2-phenoxyethyl, 3-chloro-1-propylbutyl, 2-fluoro-1-methylethyl, 2-ethoxycarbonylethyl, 2-aminoethyl, 3-dimethylaminopropyl, 3-morpholino-1-methylpropyl, 2-piperidino-1-methylethyl, nitromethyl, 2-cyano-1-methylethyl, styryl, 3-phenyl-2-propenyl and so on. Among them, more advantageous is the lower alkyl, especially of four carbon atoms, substituted with the phenyl which may have hydroxyl or lower alkoxy as a substituent(s). This lower alkyl is advantageously one branching at its α-position.

With reference to the formula (I), the cyclic hydrocarbon group which may be substituted, denoted by $R^1$, is exemplified by cycloalkyl, advantageously of 3 to 7 membered-ring (e.g. cyclopropyl, cyclobutyl, cyclopentyl, cyclohexyl, cycloheptyl, etc.), cycloalkenyl, advantageously of 3 to 7 membered-ring (e.g. cyclopentenyl, cyclohexenyl, etc.), aryl (e.g. phenyl, naphthyl, etc.) and so on. Among them more advantageous is cycloalkyl of 3 to 7 membered-ring. These groups may contain, in optional positions, appropriate substituent or substituents such as the lower alkyl, hydroxyl, lower alkoxy, halogen and other groups mentioned hereinbefore for the substituent or substituents of the cycloalkyl, cycloalkenyl, aryl and heterocyclic groups mentioned in connection with the substituted acyclic hydrocarbon group. Among typical examples of the cyclic hydrocarbon group which may be substituted are cyclopropyl, cyclobutyl, cyclopentyl, cyclohexyl, cycloheptyl, 2-methylcyclopropyl, 2-methylcyclobutyl, 3-methylcyclobutyl, 2,2-dimethylcyclobutyl, 3,3-dimethylcyclobutyl, 4-methylcyclohexyl, 4-hydroxycyclohexyl, 4-methoxycyclohexyl, 2-chlorocyclopentyl, 2-cyclohexenyl, 2-cyclopentenyl, phenyl, α-naphthyl, 4-chlorophenyl, 4-methoxyphenyl, 2-fluorophenyl, 4-hydroxyphenyl, 3,4-dimethoxyphenyl and so on.

The acyl derived from a carboxylic acid represented by $R^1$, is exemplified by the acyl derived from the carboxylic acid corresponding to the aforementioned acyclic hydrocarbon, cyclic hydrocarbon and heterocyclic groups which may be substituted, such as those mentioned hereinbefore as the varieties of $R^1$ (e.g. formyl, acetyl, methoxyacetyl, chloroacetyl, propionyl, butyryl, isobutyryl, methacryloyl, cyclohexanecarbonyl, benzoyl, toluoyl, mesitoyl, 4-chlorobenzoyl, 4-hydroxybenzoyl, phenylacetyl, p-methoxyphenylacetyl, 3-phenylpropionyl, 2-phenylpropionyl, cinnamoyl, etc.). The advantageous is lower alkanoyl, especially of up to 6 cabon atoms. Referring to the formula (I) the acyl for Y may be exemplified by acryl groups derived from carboxylic acids, carbonic acids, carbamic acids, sulfenic acids, sulfinic acids and sulfonic acids. As the acyl derived from carboxylic acid, there may be mentioned various acyls similar to those acyls described above in connection with the definition of $R^1$. As examples of the carbonic acid-acyl groups, there may be mentioned lower alkoxycarbonyls (e.g. methoxycarbonyl, ethoxycarbonyl, propoxycarbonyl, butoxycarbonyl, etc.). Among said carbamic acid-acyl groups are carbamoyl, N-mono- or di-lower alkyl-carbamoyl (e.g. N-methylcarbamoyl, N-ethylcarbamoyl, N,N-dimethylcarbamoyl, etc.) and so on. The acyl groups derived from sulfenic, sulfinic or sulfonic acids include, among others, lower alkylthio (e.g. methylthio, ethylthio, propylthio, butylthio, etc.), lower alkanesulfinyl (e.g. methanesulfinyl, ethanesulfinyl, propanesulfinyl, butanesulfinyl, etc.), lower alkanesulfonyl (e.g. methanesulfonyl, ethanesulfonyl, propanesulfonyl, butanesulfonyl, etc.) halogenated lower alkanesulfonyl (e.g. trifluoromethanesulfonyl, etc.) and so on.

Where there exists a protective group on the hydroxyl which may be protected, as designated by symbol Y hereinbefore, the said protective group may be any group that is able to protect the hydroxyl Y. Thus, such protective group may be exemplified of lower alkyl, advantageously of up to six carbon atoms (e.g. methyl, ethyl, n-propyl, i-propyl, n-butyl, i-butyl, t-butyl, sec-butyl, n-pentyl, i-pentyl, t-pentyl, n-hexyl, etc.), lower alkenyl, advantageously of up to six carbon atoms (e.g. vinyl, propenyl, butenyl, pentenyl, hexenyl, etc.), lower alkynyl, advantageously of up to six carbon atoms (e.g. ethynyl, propynyl, butynyl, pentynyl, hexynyl, etc.), lower cycloalkyl, advantageously of 3 to 7 membered-ring (e.g. cyclopentyl, cyclohexyl, etc.), substituted lower alkyl (e.g. methoxymethyl, butoxymethyl, 1-butoxybutyl, 1-methoxy-1-methylethyl, methylthiomethyl, benzylthiomethyl, phenylthiomethyl, dimethylaminomethyl, monochloromethyl, dichloromethyl, trichloromethyl, bis-(2-chloroethoxy)methyl, tributoxymethyl, etc.), aralkyl (e.g. benzyl, phenethyl, 3-phenylpropyl, α-methylbenzyl, diphenylmethyl, trytyl, etc.), phenacyl (phenacyl, p-bromophenacyl, etc.), acyl derived from carboxylic acid, sulfonic acid, carbonic acid or carbamic acid (e.g. formyl, acetyl, propionyl, butyryl, 2-methyl-2-butenoyl, monochloroacetyl, dichloroacetyl, trifluoroacetyl, benzoyl, toluoyl mesitoyl, 4-chlorobenzoyl, 3-benzoylpropanoyl, xanthene-9-carbonyl, benzenesulfonyl, toluenesulfonyl, methanesulfonyl, trifluoromethanesulfonyl, benzyloxycarbonyl, t-butyloxycarbonyl, i-bornyloxycarbonyl, carbamoyl, trichloromethylimidoyl, etc.), silyl (e.g. trimethylsilyl, etc.), ester residues of inorganic acid (e.g. nitrous acid ester residues, sulfuric acid ester residues, boric acid ester residues, dibenzylphosphoryl, p-nitrobenzylphosphoryl, p-bromobenzylphosphoryl, etc.), pyranyl, tetrahydropyranyl, tetrahydrofuranyl, thiopyranyl, 4-methoxytetrahydropyran-4-yl, 2-nitro-4-methoxyphenylthio and so on. When the symbol Y is hydrogen or hydroxyl which may be protected, n is 1 to 2.

The amino which may be subsituted, for Y, may be any of amino, secondary amino (mono-substituted amino), tertiary amino(di-substituted amino) and cycloamino groups. Examples of the secondary or tertiary amino groups are methylamino, ethylamino, isopropylamino, benzylamino, dimethylamino, diethylamino, N-benzyl-N-methylamino, formylamino, acetylamino, propionylamino, N-methyl-N-formylamino, N-methyl-N-acetylamino, N-methyl-N-trifluoroacetylamino, N-benzoyl-N-methylamino, N-benzyloxycarbonyl-N-methylamino, methanesulfonylamino, ethanesulfonylamino, N-methyl-N-methanesulfonylamino, N-benzyl-N-methanesulfonylamino, methoxycarbonylamino, ethoxycarbonylamino, propoxycarbonylamino, butoxycarbonylamino, carbamoylamino, methylcarbamoylamino, ethylcarbamoylamino and so on. The cycloamino group may be exemplified by piperidino, morpholino and so on. Advantageous examples of said amino group which may be substituted include amino, mono- and di-lower alkylamino, (the lower aklyl moieties of which advantageously contain not more than 3 carbon atoms, e.g. methyl, ethyl, n-propyl, i-propyl, etc.) and monoacylamino groups (e.g. formylamino, acetylamino, methanesulfonylamino, methoxycarbonylamino, carbamoylamino, methylcarbamoylamino, etc.). Particularly advantageous are amino and mono-lower alkylamino groups (advantageously, an amino substituted by a lower alkyl group of not more than 3 carbon atoms, e.g. methylamino, ethylamino, n-propylamino, i-propylamino, etc.).

Halogen for Y includes fluorine, chlorine, bromine, and iodine.

Referring to the formula (I), where the hydroxyl designated by $-OZ^1$ is protected, the protective group may be one of those protective groups mentioned hereinbefore in connection with the hydroxyl for Y which, also, may be protected.

When the compound (I) and their salts are used for the therapy and prophylaxis of asthma, those compounds, inclusive of salts thereof, in which, referring to formula (I), $-OZ^1$ is an unprotected hydroxyl group, and Y is the acyl derived from carboxylic or sulfonic acid (n is zero or 1), the hydroxyl which may be protected by lower alkyl or acyl (n is 1 to 2), the amino which may be substituted (n is zero), nitro (n is zero), cyano (n is zero) or halogen (n is zero) are advantageous; those compounds in which $-OZ^1$ is an unprotected hydroxyl and Y is the amino which may be substituted (n is zero) or an unprotected hydroxyl (n is 1 to 2), as well as their salts, are still more desirable; and the compounds wherein $-OZ^1$ is an unprotected hydroxyl and Y is amino (n is zero), mono-lower alkylamino (n is zero) or an unprotected hydroxyl (n is 1), inclusive of their salts, are the most beneficial.

The compound (I) of the present invention and its salts can be produced by variety of means.

For example:

Process-1

The compound (I) and its salts may be produced by reducing a compound of the formula

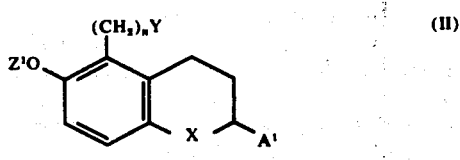

wherein Y, n and $OZ^1$ have the same meanings as defined above, $A^1$ is a group of the formula $-NHR^1$ (wherein $R^1$ has the same meaning above) or a group which can be converted to $-NHR^1$ by reduction, and X is $>C=O$ or $>CH-OH$, with a proviso that when $A^1$ is a group of the formula $-NHR^1$, X is not $>CH-OH$.

Process-2

The compound (I) and its salts may be produced by reducing a compound of the formula

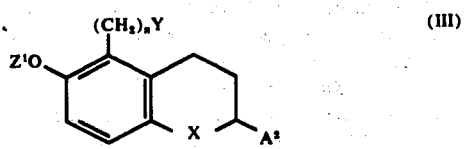

wherein Y, n, $OZ^1$ and X have the same meanings as defined above, and $A^2$ is amino or a group which can be converted to amino by reduction, in the presence of a carbonyl compound of the formula

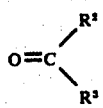

wherein $R^2$ is hydrogen or lower alkyl and $R^3$ is hydrogen, or a hydrocarbon or heterocyclic group which may be substituted, including a case where $R^2$ and $R^3$ form a ring group taken together with the adjacent carbon atom.

Process-3

The compound (I) and its salts may be produced by subjecting a compound of the formula

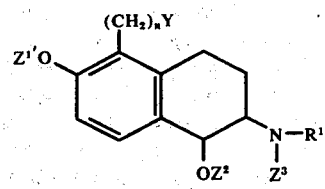

wherein $R^1$, Y and n have the same meanings as defined above, $OZ^{1'}$ and $OZ^2$, respectively, are hydroxyl which may be protected and $Z^3$ is hydrogen or a protective group, to a reaction leading to removal of the protective group.

Referring to the formula (II), the group which can be converted to $-NHR^1$ by reduction, designated by symbol $A^1$, may be any group that is convertible to $-NHR^1$ in whatever manner of reduction. Examples of such groups, in the case where $R^1$ is the hydrocarbon group, include amino substituted with acyl derived from carboxylic acid (e.g. formylamino, acetylamino, propionylamino, butyrylamino, isopropionylamino, sec-butyrylamino, α,α-dimethylpropionylamino, crotonylamino, cyclohexylcarbonylamino, 2-cyclohexene-1-ylcarbonylamino, cyclopentylcarbonylamino, benzoylamino, β-phenylpropionylamino, etc.), $-N=R^1$, $=N-R^1$,

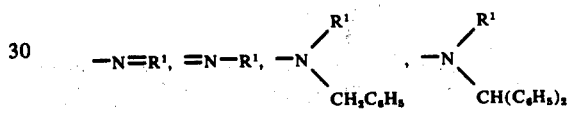

(wherein $R^1$ has the same meaning as defined hereinbefore) and so on. In the case where $R^1$ is hydrogen, the group which can be converted into $-NHR^1$ by reduction is exemplified by the group mentioned hereinafter for $A^2$.

Referring to the formula (III), the group which can be converted to amino by reduction, as designated by symbol $A^2$, may be any groups insofar as they are ready to be converted into amino in whatever manner of reduction, for example, nitro, nitroso, isonitroso (oxyimino), hydroxyamino, imino, acyloxyimino, diazo, azido, phenylhydrazono and so on.

Referring to the formula (IV), the lower alkyl designated by $R^2$ may be straight or branched, advantageously of up to six carbon atoms, for example, methyl, ethyl, n-propyl, i-propyl, n-butyl, i-butyl, sec-butyl and so on. The hydrocarbon group designated by $R^3$ is exemplified by the hydrocarbon groups mentioned hereinbefore for $R^1$. As the heterocyclic groups for $R^3$ there may be enumerated those heterocyclic groups mentioned hereinbefore in connection with the substituents of the acyclic hydrocarbon groups for $R^1$. It should be noticed that $R^2$ and $R^3$ may form a ring group as taken together with the adjacent carbon atoms; examples of said ring include cycloalkane, advantageously of 3 to 7 membered-ring (e.g. cyclopropane, cyclobutane, cyclopentane, cycloheptane, etc.), cycloalkene, advantageously of 3 to 7 membered-ring (e.g. cyclopentene, cyclohexene, etc.) and so on. Among them more advantageous is cycloalkane of 3 to 7 membered-ring.

Referring to the formula (V), when $-OZ^{1'}$ and/or $-OZ^2$ is protected hydroxyl, each of the protective groups is exemplified by the protective groups mentioned hereinbefore in connection with the hydroxyl Y or $-OZ^1$ which may be protected.

Referring to the formula (V), the protective group designated by symbol $Z^3$ may be any groups insofar as they are ready to protect the amino, and to be removed by a reaction for removing the protective group. Examples of such groups include acyl and aralkyl respectively mentioned hereinbefore for the protective group in —$OZ^1$. The protective group $Z^3$ may protect the amino and/or hydroxyl, in the forms linked together with the protective group in —$OZ^2$ and/or $R^1$. In the case that $Z^3$ links with —$OZ^2$, the linking protective group is exemplified by lower alkylidene of up to six carbon atoms (e.g. methylidene, ethylidene, propylidene, isopropylidene, butylidene, pentylidene, hexylidene, etc.), substituted lower alkylidene (e.g. 1-methoxyethylidene, 1-ethoxyethylidene, phenylmethylidene, diphenylmethylidene, phenethylidene, 1-phenylethylidene, acetylisopropylidene, oxomethylidene, iminomethylidene, thioxomethylidene, etc.) or the like.

Other linking examples are shown as the following formulas (V'), (V'') and (V'''):

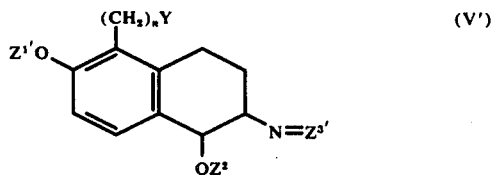

wherein Y, n, -$OZ^{1\,\prime}$ and -$OZ^2$ have the same meanings as defined hereinbefore and $Z^{3\,\prime}$ is lower alkylidene of up to six carbon atoms (e.g. methylidene, ethylidene, propylidene, isopropylidene, butylidene, etc.), substituted lower alkylidene (e.g. benzylidene, phenethylidene, 1-methoxyethylidene, 1-ethoxyethylidene, 1-phenylethylidene, 1-ethoxyethylidene, acetylisopropylidene, etc.), fluoroenylidene, phthaloyl or succinoyl.

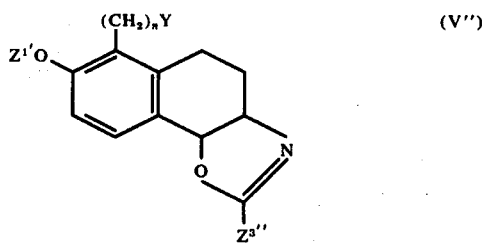

wherein Y, n and -$OZ^{1\,\prime}$ have the same meanings as defined hereinbefore, and $Z^{3\,\prime\prime}$ is hydrogen, or lower alkyl of up to six carbon atoms (e.g. methyl, ethyl, propyl, butyl, pentyl, hexyl, etc.), aralkyl (e.g. benzyl, phenethyl, etc.), methylthio or methoxy, and these groups as $Z^{3\,\prime\prime}$ may have a substituent or substituents (e.g. hydroxyl, lower alkoxy of up to six carbon atoms, halogen, etc.).

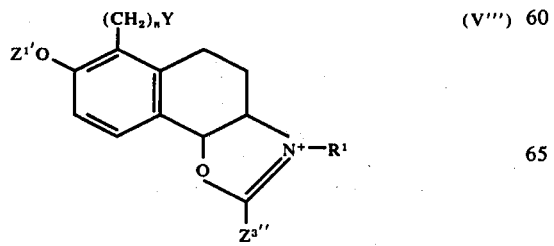

wherein Y, n, $R^1$, -$OZ^{1\,\prime}$ and $Z^{3\,\prime\prime\prime\prime}$ have the same meanings as defined hereinbefore.

When the compound of the formula (V') or (V'') is subjected to a reaction for removing the protective group in Process-3, the compound of the formula (I) wherein $R^1$ is hydrogen is ordinary obtained.

Processes-1 to 3 will be explained in detail as follows.

The reduction in Process-1 or 2 may be conducted by a reducing procedure suitably selected, according to the starting material then employed. from conventional ones such as given below; (1) catalytic reduction with platinum, palladium, rhodium, nickel, or the like as catalyst, (2) reduction by means of a metal hydride such as lithium aluminum hydride, lithium borohydride, lithium cyanoborohydride, sodium borohydride, sodium cyanoborohydride or the like, (3) Meerwein-Ponndorf-Verley reduction by means of aluminum alkoxide, e.g. aluminum isopropoxide, (4) reduction by means of metallic sodium, metallic magnesium or the like with, for example, alcohol, (5) reduction by means of zinc dust with base such as caustic alkali, (6) reduction by means of a metal such as iron or zinc with an acid such as hydrochloric acid or acetic acid, (7) electrolytic reduction, (8) reduction with the aid of reducing enzymes. It should be understood that, aside from the above procedures, any method can be employed insofar as it is able to attain the object of the present invention. While the advantageous reaction temperature varies with starting materials and reduction procedures then employed, ordinarily it falls within the range of about −20° to about 100° C. This reaction is ordinarily carried out at atmospheric pressure but, if desired, it may be carried out at reduced or elevated pressure. The reduction is usually conducted in the presence of a suitable solvent. The solvent is of optional type, insofar as it is capable of dissolving, more or less, the starting material and will not adversely affect the reaction, such as water, an alcohol (e.g. methanol, ethanol, propanol, etc.), an ether (e.g. dimethyl ether, diethyl ether, methyl ethyl ether, tetrahydrofuran, dioxane, etc.), an ester (e.g. ethyl acetate, butyl acetate, etc.), a ketone (e.g. acetone, methyl ethyl ketone, etc.), an aromatic hydrocarbon (e.g. benzene, toluene, xylene, etc.), an organic acid (e.g. acetic acid, propionic acid, etc.) or a mixture of two or more thereof.

In the reduction in Process-2, it is possible to carry out the reaction using an excess of the carbonyl compound (IV) also in role of the solvent.

The reduction in Process-1 or 2 may be carried out step by step, for example, when the starting material has more than two moieties which can be reduced, it is possible to obtain the compound (I) by reducing these moieties step by step.

In Process-1 or 2 of the present invention, starting materials include various compounds, giving respectively corresponding object compounds (I). Thus, in accordance with the starting material and the desired object compound, the suitable reduction means and conditions are selected from those mentioned above.

The reaction in Process-3 is conducted by subjecting the compound (V) to a reaction leading to removal of the protective group. The reaction for removal of the protective group may be any reaction that is able to remove the protective group. Advantageous examples of such reaction include reduction, oxidation, solvolysis (e.g. hydrolysis, alcoholysis, etc.) and so on. More detailed examples of these reactions are given as follows; (1) catalytic reduction with platinum, palladium, rhodium, Raney-nickel or the like as catalyst, (2) reduction by means of metallic sodium, metallic potassium or the like with liquid ammonia or alcohol such as ethanol or butanol, (3) reduction by means of a metal hydride such as lithium aluminum hydride, sodium aluminum hydride, sodium borohydride or the like, (4) reduction by means of a metal such as zinc, iron or the like with an acid such as an organic acid (e.g. formic acid, acetic acid, etc.), an inorganic acid (e.g. hydrochloric acid, sulfuric acid, etc.) or the like, (5) reaction by means of a Lewis acid such as aluminum chloride, aluminum bromide, zinc chloride, magnesium iodide, ferric chloride, boron trichloride, boron tribromide, or the like, (6) reaction by means of an acid such as a hydrohalogenic acid (e.g. hydrogen fluoride, concentrated hydrobromic acid, hydrogen bromide-acetic acid, hydrogen chloride, hydrogen iodide, etc.), sulfuric acid, nitric acid, phosphoric acid, perchloric acid, boric acid or the like, or a solution of said acid such as an aqueous solution, an alcoholic solution or the like, (7) reaction by means of an organic acid such as trifluoroacetic acid, acetic acid, oxalic acid, paratoluenesulfonic acid, formic acid or the like, or an aqueous solution of said organic acid, (8) reaction by means of an inorganic base such as sodium hydroxide, potassium hydroxide, barium hydroxide, potassium carbonate, sodium hydrogen carbonate, aqueous ammonia, hydrazine hydrate or the like, or an organic base such as pyridine hydrochloride, tetramethylammonium hydroxide, collidine-lithium iodide, or the like, (9) reaction by means of an oxidizing agent such as concentrated nitric acid, chromic anhydride, potassium permanganate, ozone, benzoyl peroxide or the like, (10) reaction by means of a chemical substance such as thiourea, mercaptide, lead acetate or the like, (11) reaction by means of a solvent such as water, methanol, ethanol or the like, (12) physical treatment such as electrolytic reduction, electrolytic oxidation, irradiation of ultraviolet rays or the like, (13) enzymatic reaction and so on. While the advantageous reaction temperature varies with reaction procedures then employed, ordinarily it falls within the range of about $-40°$ to about $150°$ C. This reaction is ordinarily carried out at atmospheric pressure but, if desired, it may be carried out at reduced or elevated pressure.

The reaction in Process-3 may be carried out step by step; for example, when the starting compound (V) has more than two protective groups, it is possible to obtain the compound (I) by removing these protective groups step by step.

In the case that reduction is employed as the reaction for removing the protective group, an advantageous group as the protective group in $-OZ^{1'}$ and/or $-OZ^2$ of the starting compound (V) among the various protective groups mentioned hereinbefore for $-OZ^{1'}$ and $-OZ^2$ is the lower alkenyl, lower alkynyl, aralkyl, phenacyl, acyl or the like. In the case that solvolysis, e.g. (5), (6), (7), (8) or (11) described above, is employed, an advantageous group as the protective group in $-OZ^{1'}$ and/or $-OZ^2$ among them is the lower alkyl, lower alkenyl, lower alkynyl, substituted lower alkyl, aralkyl, acyl, silyl, ester residues of inorganic acid, pyranyl, tetrahydropyranyl, tetrahydrofuranyl, thiopyranyl or the like.

In Process-1 or 2, when $R^1$, $R^3$, $-(CH_2)_nY$, and/or $-OZ^1$ in the starting compound (II), (III) and/or (IV) are the groups which can be reduced by the reduction reaction of the present invention, these groups may be also reduced whereby corresponding compounds are obtained in which the aforementioned moieties have been reduced. To describe a few such cases, where $R^1$ or $R^3$ in the starting compound is an unsaturated group, there is obtained the product compound with the corresponding saturated group; where $R^1$ in the starting compound is acyl derived from carboxyl acid, there is obtained the product compound in which the ($-CO-$) moiety has been converted to ($-CH_2-$); where the $-(CH_2)_nY$ moiety of the material compound is a nitro group, there is obtained the product compound wherein the nitro group has been converted to an amino group; where the $-(CH_2)_nY$ moiety is formyl, there is obtained the product compound with a hydroxymethyl group in the corresponding position; and where $-OZ^1$ in the starting compound is a benzyloxy group, there is obtained the product compound with a hydroxyl group in the corresponding position.

In Process-3, when $R^1$ and/or $-(CH_2)_nY$ contain the groups modifiable by the reaction leading to removal of protective groups, there are cases in which there is obtained a compound in which the aforementioned groups have been modified. For example, when a reductive procedure is adopted for the reaction leading to removal of protective groups, the same modifications as those mentioned in connection with Processes-1 and 2 may take place. Where a hydrolytic procedure is employed, there are cases in which the product compound is obtained wherein the aforementioned $R^1$ and/or $-(CH_2)_nY$ moieties have been hydrolyzed.

Thus, as will be apparent from the above exemplary cases, the symbols $R^1$, $R^2$, $R^3$, $-(CH_2)_nY$, $-OZ^1$, etc. as used in common for the starting compounds and product compounds in connection with Processes-1 to 3 mean that they represent the groups falling within the respective defined categories, and they are not intended to mean that these groups each remain the same before and after the reaction.

The contemplated compound (I) of this invention can by easily isolated from the respective reaction mixtures by separation and purification procedures which are conventional per se, such as concentration, filtration, column chromatography, recrystallization, and so on.

The compound (I) may occur in several stereo-isomers such as geometrical isomers and optical isomers due to the presence of some asymmetrical carbon atoms and, therefore, is generally obtained as mixtures of such isomers.

If desired, an optional geometrical isomer (for example, trans-isomer, cis-isomer) can be obtained by suitable procedures such as (1) reduction with the use of the starting compound (II) wherein X is $>CH-OH$ which has the same configuration as that of the contemplated compound (I), (2) stereospecific reduction (e.g. the compound (I) of transisomer is obtained by the reduction of the starting compound (II) wherein X is $>C=O$ with the use of sodium borohydride), (3) isolation of the optional isomer from a mixture of isomers by using suitably selected procedures among the aformentioned separation and purification procedures such as recrystallization, column chromatography, and so on.

The racemic mixture may, if desired, be resolved by conventional procedures, for example by causing it to form a salt with an optically active acid or base or, alternatively, by physical adsorption on a porous adsorptive resin. It is to be understood that all individual isomeric forms as well as their mixture are included in the scope of the present invention.

The contemplated compound (I) of this invention may also be isolated after it has been converted to salts, especially to physiologically acceptable salts such as acid addition salts in the conventional manner; for example, an inorganic acid salt (such as hydrochloride, hydrobromide, sulfate, etc.), an organic acid salt (such as maleate, fumarate, tartrate, toluenesulfonate, naphthalenesulfonate, methanesulfonate, etc.).

The contemplated products of this invention thus obtained, i.e. the compound of the formula (I) and its physiologically acceptable salts, have excellent pharmacological activities such as the activity to stimulate or block $\beta$-adrenergic receptors, coronary vasodilator activity, analgetic activity, hypotensive activity, central nervous system depressant activity, antidepressive activity and so on. Especially the activity to stimulate $\beta_2$-adrenergic receptors such as bronchodilating activity is noticeable. Because of these useful properties of the compound (I) and its salts, they are of value in the therapy and prophylaxis of diseases such as asthma, arrhythmia, angina pectoris, migraine, hypertension, neuralgia, and so on, in mammals.

In the pharmaceutical usage of any of the contemplated compounds and their salts of this invention, they may be administered to mammals including human beings as they are or in admixture with a pharmaceutically acceptable carrier or carriers, orally or by other routes in such dosage forms as powders, granules, tablets, capsules, injections, inhalations, etc.

Pharmaceutical compositions containing one or more of the compound (I) or its salts can be prepared by conventional techniques for the preparation of powders, granules, tablets, capsules, injections, inhalations and the like. The choice of carriers may be determined depending upon the route of administration, the physical and chemical properties of the compound (I) and its salts, and so on. If desired, stabilizers such as sodium bisulfite and ascrobic acid may be employed.

While the proper dosage depends upon the particular disease and symptom to be dealt with, the route of administration and other conditions, advantageous dose levels in the therapy of asthma in adult humans are in the range of about 1 to 100 milligrams daily by the oral route, about 0.01 to 1 milligram per day intravenously or about 0.1 to 10 milligrams per dose by topical route in such dosage forms as nebulized products (aerosol inhalations).

Table 1, below, shows the effect of 1,6-dihydroxy-5-hydroxymethyl-2-isopropylamino-1,2,3,4-tetrahydronaphthalene, which is one typical compound among the contemplated products of the present invention, on isolated guinea-pig tracheal muscles and atria, in comparison with the corresponding effect of isoproterenol, a known drug. The value given is relative to the value 100 for isoproterenol.

Table 1

| Effect on tracheal muscle [1] | Effect on atria [2] |
| --- | --- |
| Ca. 150 | Ca. 6 |

[1] and [2]: Determined by the methods of Masao Nishikawa et al. appearing in Life Sciences Vol. 16, pp. 305–314.

The compound (I) of the present invention is also of use as synthetic intermediates for the production of various drugs.

The starting compounds (II), (III) and (V) can be produced by, for example, processes as set forth below:

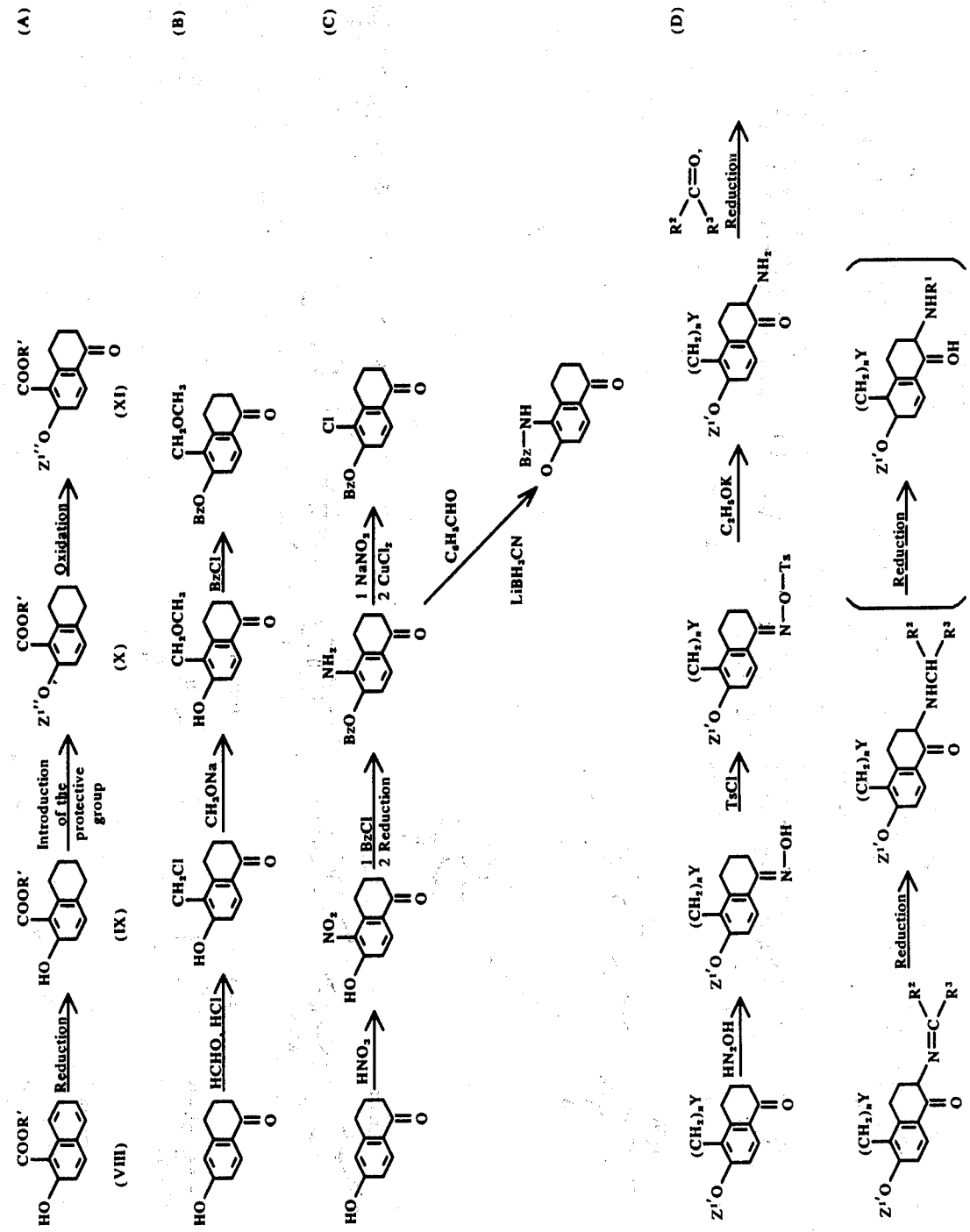

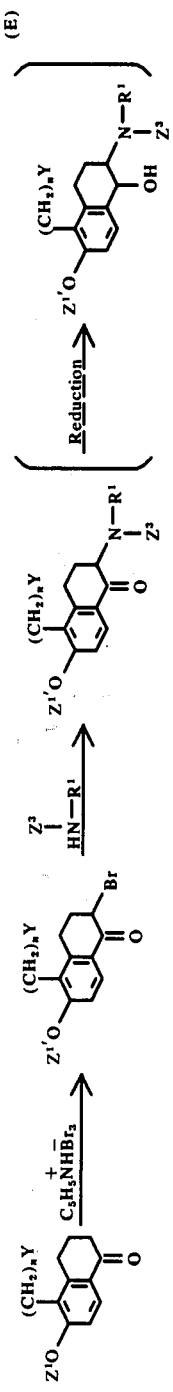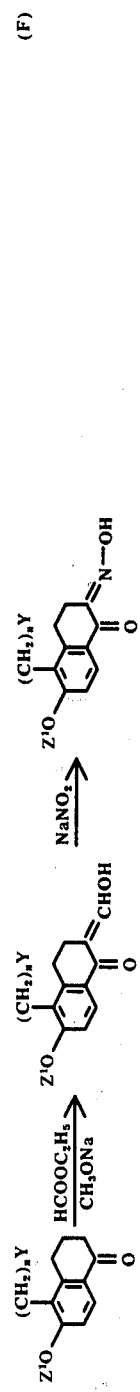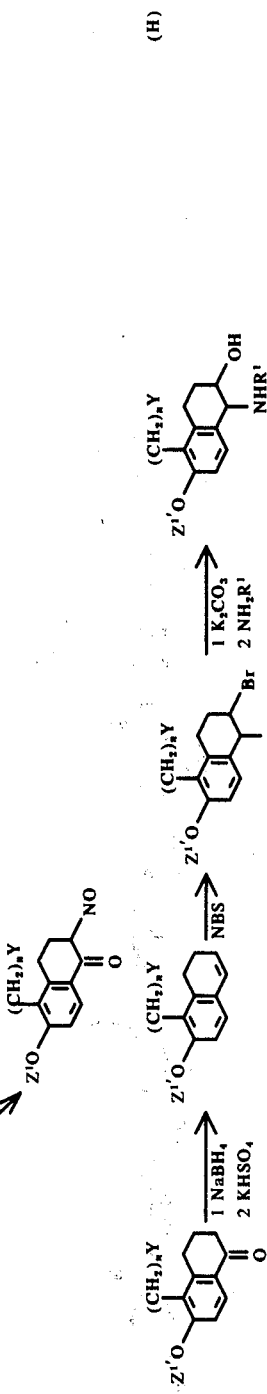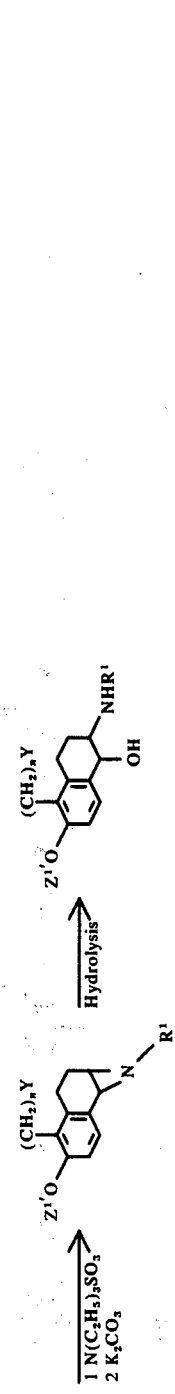

In the above formulas, $R^1$, $R^2$, $R^3$, Y, n $-OZ^1$, $-OZ^{1'}$, and $Z^3$ have the same meanings as defined hereinbefore; Bz is benzyl; Ts is tosyl; NBS is N-bromosuccinimide; $-OZ^{1''}$ is a protected hydroxyl; and $R'$ is hydrogen or lower alkyl.

Among the above-mentioned processes, the compound of the formula (XI) is especially advantageous as the intermediate for industrial production of the object compound of the formula (I) wherein Y is an unprotected hydroxyl, n is 1 and $-OZ^1$ is an unprotected hydroxyl, i.e. 2-(substituted) amino-1,6-dihydroxy-5-hydroxymethyl-1,2,3,4-tetrahydronaphthalene compounds (I'). Thus, the present invention also provides the industrially advantageous intermediate (XI) for producing the said compound (I'). A further detailed explanation for Process (A) to produce the compound (XI) is as follows:

Referring to the formulas (VIII) to (XI), the lower alkyl for R' is advantageously a straight-chain or branched lower alkyl of up to four carbon atoms, such as methyl, ethyl, n-propyl, i-propyl, n-butyl, i-butyl, sec-butyl and t-butyl.

Referring to the formulas (X) and (XI), the protective group of the protected hydroxyl designated by $-OZ^{1''}$ is exemplified by the protective groups mentioned hereinbefore in connection with the hydroxyl $-OZ^1$ or Y.

In Process (A), a compound of the formula (VIII) is first reduced to a compound of the formula (IX). This reduction may be practically accomplished by catalytic reduction, for instance. The catalytic reduction may be advantageously conducted in water, a nonreducible organic solvent (e.g. methanol, ethanol, ethyl ether, dioxane, tetrahydrofuran, ethyl acetate, formic acid, acetic acid, etc.), or a mixture of such solvent and in the presence of a metal catalyst such as palladium, platinum, Raney nickel, rhodium or the like, ordinarily at a temperature within the range of room temperature to about 100° C and at a pressure in the range of about 1 to 200 atmospheres, advantageously of about 50 to 150 atmospheres, in a current of hydrogen. While the reaction time depends upon the pressure and the type of catalyst employed, the time when a stoichiometric amount, i.e. about 2 mole equivalents, of hydrogen has been absorbed and the reaction does not proceed any longer may be expediently taken as the end point of the reaction.

By introducing a protective group into the hydroxyl of the compound (IX) thus obtained, there can be produced a compound of the formula (X). The introduction of a protective group into the hydroxyl group of the compound (IX) in this reaction stage may be accomplished by a procedure known per se for the introduction of each of the aforementioned various protective groups. For example, benzyl may be thus introduced by permitting benzyl chloride to act upon the compound (IX) in the presence of a base, e.g. potassium carbonate or sodium carbonate, using dimethylformamide, for instance, as the solvent at a temperature in the range of about 50° to about 100° C. Acyl derived from carboxylic acid can be introduced by permitting the corresponding acid anhydride or acid halide, for instance, to act upon the compound (IX) in a solvent such as pyridine or triethylamine at a reaction temperature of about 0° to about 100° C.

The compound (XI) can be produced by oxidizing the compound (X) thus obtained. In this case, the compound (X) may be isolated and purified from the reaction mixture of the preceding reaction stage or, alternatively, the reaction mixture as such may be subjected to the oxidation reaction. The oxidation in this step may be accomplished by any procedure known per se only if it is capable to oxidize the compound (X) to the compound (XI). Thus, oxidation by means of an oxidizing agent may be mentioned by way of example. For this purpose, oxidation with chromic acid, permanganic acid, manganese dioxide, selenium dioxide or the like may prove of advantage.

As for oxidizing agents for chromic acid oxidation, there may be mentioned chromic anhydride, chromic acid, dichromates (e.g. potassium dichromate, sodium dichromate, ammonium dichromate, etc.), chromates (e.g. potassium chromate, sodium chromate, ammonium chromate, etc.), chromic acid chlorides (e.g. chromyl chloride, etc.) and so on. As for permanganic acid oxidation, there may for example be mentioned such oxidizing agents as permanganates (e.g. potassium permangante, sodium permanganate, barium permanganate, calcium permanganate, magnesium permanganate, etc.). The oxidation reaction with such an oxidizing agent is commonly carried out in a suitable inert solvent such as acetone, benzene, pyridine, dioxane, ethyl acetate, acetic acid, sulfuric acid or water or a mixture of such solvents. While the reaction temperature depends upon the type of oxidizing agent and of solvent, among others, it is generally selected from the range of about −10° to about 150° C. The time required for completing the reaction also varies with the oxidizing agent, reaction temperature and solvent employed, among other factors. If necessary, the progress of the reaction may be monitored by thin-layer chromatography (TLC). The compound (XI) thus-produced can be easily isolated from the reaction mixture by a conventional recovery-purification procedure such as extraction, concentration, filtration, recrystallization, distillation, column chromatography and so on, in the free form where R' is lower alkyl, or in the free form or as a salt where R' is hydrogen. The aforementioned salt may be the salt of an alkali metal (e.g. sodium, potassium, lithium, etc), alkaline earth metal (e.g. calcium magnesium, etc.), aluminum or other metal, or ammonium salt or a salt of an organic amine (e.g. methylamine, ethylamine, dimethylamine, diethylamine, trimethylamine, triethylamine, etc.). It should be understood that when the compound (XI) is used as the intermediate it may be used without isolation from the reaction mixture or as acrude product.

When this compound (XI) is employed as the intermediate for producing the above-mentioned compound (I'), the compound (XI) is converter to the compound (XII) shown in Process (I) by, for example, an appropriate one of Processes (D) to (H) or a suitable combination of the reactions involved in these processes. For instances, the compound (XII) can be obtained with a good yield by subjecting the (XI) to Process (D) or Process (H). Thus-obtained compound (XII) is subjected to Process (I) to obtain the compound (XIII), which is subjected to Process-3, i.e. to the reaction for removal of the protective group, whereby the compound (I') is obtained in a good yield.

Reverting now to the starting compounds (II), (III) and (V), these compounds with various substituents for $-(CH_2)_nY$, $A^1$, $A^2$, $-OZ^{1'}$, $-OZ^2$, $Z^3$ and $R^1$ may be easily converted to the starting compounds with desired substituents, for example, by subjecting the compound obtained in Process (B) or (C) or the compound obtained therefrom in Process (D), (E), (F) or (G), to a reaction that is known per se.

The following Reference Examples and Examples are further illustrative of this invention. It should, of course, be understood that the scope of the invention is by no means limited by and to these examples.

Throughout the foregoing description as well as in the following Reference Examples and Examples, "g.", "mg.", "l.", "ml.", "N" and "°C" respectively refer to "gram(s)", "milligram(s)", "liter(s)", "milliliter(s)", "Normal(s)" and "degree(s) centigrade", and "NMR" means "nuclear magnetic resonance".

REFERENCE EXAMPLE 1

To a mixture of 20 g. of 6-hydroxy-3,4-dihydro-1(2H)-naphthalenone and 110 ml. of concentrated hydrochloric acid is added 4.6 g. of paraformaldehyde and the mixture is agitated at room temperature for 20 hours. To the reaction mixture is added 200 ml. of water, and the resulting precipitate is recovered by filtration, rinsed with water and benzene and dried. The described procedure provides 5-chloromethyl-6-hydroxy-3,4-dihydro-1(2H)-naphthalenone. Yield 21 g.; melting point: 172°–174° C (decomp.).

Elemental analysis; for $C_{11}H_{11}O_2Cl$; Calculated C, 62.71; H, 5.26; Found C, 62.66; H, 5.13.

REFERENCE EXAMPLE 2

In 300 ml. of methanol is dissolved 21 g. of 5-chloromethyl-6-hydroxy-1(2)-naphthalenone, followed by addition of 17 ml. of triethylamine. The mixture is refluxed for 3 hours, after which time it is concentrated under reduced pressure. To the residue are added water, ethyl acetate and 5 ml. of acetic acid, and the mixture is extracted with ethyl acetate. The ethyl acetate layers are pooled, washed with water and dried over anhydrous sodium sulfate. The solvent is then distilled off under reduced pressure. The residue is then recrystallized from a mixture of benzene and n-hexane. The procedure provides 6-hydroxy-5-methoxymethyl-3,4-dihydro-1(2H)-naphthalenone as colorless prisms. Yield 19 g.; melting point: 142°–143° C.

Elemental analysis; for $C_{12}H_{14}O_3$; Calculated C, 69.88; H, 6.84; Found C, 69.87; H, 6.82.

REFERENCE EXAMPLE 3

To 300 ml. of dimethylformamide are added 52 g. of 5-hydroxy-6-methoxymethyl-3,4-dihydro-1(2H)-naphthalenone, 32 g. of benzyl chloride and 35 g. of anhydrous potassium carbonate, and the mixture is stirred at 100° C for 4 hours. The reaction mixture is poured in 1 liter of water and the liberated oily layer is separated. To this layer is added 300 ml. of ethyl acetate and, after washing with water, the solution is dried over anhydrous sodium sulfate. The solvent is then distilled off under reduced pressure and the residue is recrystallized from hexane. The procedure provides 6-benzyloxy-5-methoxymethyl-3,4-dihydro-1(2H)-naphthalenone as colorless needles. Yield 58 g.; melting point; 55°–56° C.

Elemental analysis; for $C_{19}H_{20}O_3$; Calculated C, 77.00; H, 6.80; Found C, 76.75; H, 6.83.

REFERENCE EXAMPLE 4

In 200 ml. of glacial acetic acid is dissolved 58 g. of 6-benzyloxy-5-methoxymethyl-3,4-dihydro-1(2)-naphthalenone, followed by the addition of 34 ml. of a 47 % aqueous solution of hydrobromic acid. The mixture is allowed to stand at 40°–50° C for 4 hours. The reaction mixuture is concentrated under reduced pressure and the residue is dissolved in 500 ml. of benzene. The solution is washed with water and dried over anhydrous sodium sulfate. The solvent is then distilled off under reduced pressure and the residue is recrystallized from cyclohexane. The procedure provides 6-benzyloxy-5-bromomethyl-3,4-dihydro-1(2H)-naphthalenone as colorless needles. Yield 44 g.; melting point: 103°–104° C.

Elemental analysis: for $C_{18}H_{17}O_2Br$; Calculated C, 62.62; H, 4.96; Found C, 62.23; H, 4.54.

REFERENCE EXAMPLE 5

To 400 ml. of dimethylsulfoxide is added 80 g. of sodium hydrogen carbonate and, with agitation and under heating at 100° C in a current of molecular nitrogen, 44 g. of 6-benzyloxy-5-bromomethyl-3,4-dihydro-1(2H)-naphthalenone is added. The mixture is agitated for 20 minutes. The reaction mixture is poured in ice-water and extracted with benzene. The benzene layer is washed with water and dried over anhydrous sodium sulfate.

The solvent is then distilled off under reduced pressure and the residue is recrystallized from methanol. The procedure yields 23 g. of 6-benzyloxy-5-formyl-3,4-dihydro-1(2H)-naphthalenone as colorless needles melting at 97°–98° C.

Elemental analysis; for $C_{18}H_{16}O_3$; Calculated C, 76.57; H, 6.43; Found C, 76.53; H, 6.28.

REFERENCE EXAMPLE 6

In 50 ml. of benzene is dissolved 2.0 g. of 6-benzyloxy-5-formyl-3,4-dihydro-1(2H)-naphthalenone, followed by addition of 5 ml. of ethylene glycol and 20 mg. of p-toluenesulfonic acid. The mixture is refluxed for 2 hours, the by-product water being continually expelled. The reaction mixture is washed with an aqueous solution of sodium hydrogen carbonate and dried over anhydrous sodium sulfate. The solvent is then distilled off under reduced pressure and the residue is recrystallized from ether-n-hexane. The procedure yields 2.0 g. of 6-benzyloxy-5-formyl-3,4-dihydro-1(2H)-naphthalenone ethyleneacetal as colorless prisms melting at 88°–89° C.

Elemental analysis; for $C_{20}H_{20}O_4$; Calculated C, 74.05; H, 6.22; Found C, 74.12; H, 6.46.

REFERENCE EXAMPLE 7

In 20 ml. of methanol is dissolved 1.3 g. of sodium methoxide and, under cooling with ice, a solution of 1.4 g. hydroxylamine hydrochloride in 20 ml. methanol is added dropwise. The mixture is stirred for 30 minutes, after which time a solution of 5.2 g. of 6-benzyloxy-5-formyl-3,4-dihydro-1(2H)-naphthalenone ethyleneacetal in 20 ml. of methanol is added dropwise. The mixture is stirred at room temperature for 20 hours and, then, poured in 300 ml. of dilute hydrochloric acid, followed by stirring for 2 hours. The resulting precipitate is recovered by filtration, rinsed with water, dried and recrystallized from benzene-n-hexane. The procedure yields 3.1 g. of 6-benzyloxy-5-formyl-3,4-dihydro-1(2H)-naphthalenone 1-oxime as colorless needles melting at 176°–177° C.

Elemental analysis; for $C_{18}H_{17}O_3N$; Calculated C, 73.20; H, 5.80; N, 4.74; Found C, 73.21; H, 5.75; N, 4.75.

REFERENCE EXAMPLE 8

In 15 ml. of anhydrous pyridine is dissolved 3.17 g. of 6-benzyloxy-5-formyl-3,4-dihydro-1(2H)-naphthalenone 1-oxime and, under cooling with ice, 2.1 g. of benzenesulfonyl chloride is added dropwise. After stirring for 3 hours, the reaction mixture is left standing in a refrigerator overnight. The reaction mixture is then poured in 100 ml. of ice-water and the resulting precipitate is recovered by filtration, rinsed with water, dried and recrystallized from benzene-cyclohexane. The procedure yields 4.2 g. of 1-benzenesulfonyloxyimino-6-benzyloxy-5-formyl-1,2,3,4-tetrahydronaphthalene as colorless needles melting at 142°–143° C.

Elemental analysis; for $C_{24}H_{21}O_5NS$; Calculated C, 66.19; H, 4.86; N, 3.34; Found C, 66.51; H, 4.59; N, 3.17.

REFERENCE EXAMPLE 9

An ethanolic solution of potassium ethoxide, prepared from 25 ml. of anhydrous ethanol and 900 mg. of potassium metal, is cooled to 5° C with ice-water and, while molecular nitrogen is bubbled into the solution, a solution of 7.6 g. of 1-benzenseulfonyloxyimino-6-benzyloxy-5-formyl-1,2,3,4-tetrahydronaphthalene in 100 ml. of anhydrous benzene is added dropwise. After stirring for 2 hours, the mixture is allowed to stand in a refrigerator overnight. The reaction mixing is filtered over Celite and washed with benzene. To the filtrate is added dilute hydrochloric acid, followed by stirring for 30 minutes. The mixture is then evaporated to dryness under reduced pressure and the residue is dissolved in ethanol. The solution is treated with activated carbon and recrystallized from ethanol-ethyl acetate. The above procedure yields 3.1 g. of 2-amino-6-benzyloxy-5-formyl-3,4-dihydro-1(2H)-naphthalenone hydrochloride as colorless needles melting at 180°–185° C(decomp.).

Elemental analysis; for $C_{18}H_{17}O_3N.HCl$; Calculated C, 65.16; H, 5.47; N, 4.22; Found C, 64.95; H, 5.01; N, 4.01.

REFERENCE EXAMPLE 10

In a mixture of 10 ml. of acetone and 15 ml. of methanol is dissolved 1.0 g. of 2-amino-6-benzyloxy-5-formyl-3,4-dihydro-1(2H)-naphthalenone hydrochloride and, with the introduction of molecular nitrogen, the reaction mixture is cooled to 5°–10° C with ice and 500 mg. of the adduct of dioxane (1 mole) to lithium cyanoborohydride ($LiBH_3CN$·dioxane) is added. The mixture is stirred for 2 hours. To this reaction mixture is added ethanolic hydrogen chloride so that the mixture is acidic, and the solvent is distilled off under reduced pressure. The residue is dissolved in 95% ethanol and, after treatment with activated carbon, recrystallized from ethanol-ethyl acetate. The procedure yields 620 mg. of 6-benzyloxy-5-formyl-2-ispropylamino-3,4-dihydro-1(2H)-naphthalenone hydrochloride as white crystals melting at 175°–180° C (decomp.).

Elemental analysis; for $C_{21}H_{23}O_3N\cdot HCl$; Calculated C, 67.46; H, 6.47; N, 3.75; Found C, 67.16; H, 6.31; N, 3.38.

Mass spectrum, m/e: 337 ($M^+$-HCl)

REFERENCE EXAMPLE 11

In 100 ml. of ethanol are suspended 7.6 g. of 6-benzyloxy-5-formyl-3,4-dihydro-1(2H)-naphthalenone and 2.4 g. of anhydrous sodium acetate and, under stirring at room temperature, 2.0 g. of hydroxylamine hydrochloride is added. The mixture is stirred at room temperature for 3 hours, after which time the ethanol is distilled of under reduced pressure. To the residue is added water and the resulting precipitate is recovered by filtration. The precipitate is rinsed with water and crystallized from ethanol. The procedure yields 5.9 g. of 6-benzyloxy-5-formyl-3,4-dihydro-1(2H)-naphthalenone aldoxime as pale-yellow needles melting at 171°–173° C.

Elemental analysis; for $C_{18}H_{17}O_3N$; Calculated C, 73.20; H, 5.80; N, 4.74; Found C, 72.75; H, 5.71; N, 4.63.

REFERENCE EXAMPLE 12

In 30 ml. of pyridine is dissolved 5.9 g. of 6-benzyloxy-5-formyl-3,4-dihydro-1(2H)-naphthalenone aldoxime followed by addition of 5.3 g. of benzenesulfonyl chloride. The mixture is stirred at room temperature overnight. To the reaction mixture is added water and the resulting crystals of 6-benzyloxy-5-cyano-3,4-dihydro-1(2H)-naphthalenone are recovered by filtration. The crystals are rinsed with water and recrystalized from ethanol. The procedure yields 4.7 g. of pale-yellow needles melting at 140°–141° C.

Elemental analysis; for $C_{18}H_{15}O_2N$; Calculated C, 77.96; H5.45; N, 5.05; Found c, 77.92; H, 5.40; N, 4.94.

REFERENCE EXAMPLE 13

In 70 ml. of acetate acid is dissolved 4.7 g. of 6-benzyloxy-5-cyano-3,4-dihydro-1(2H)-naphthalenone and, under stirring at room temperature, 5.4 g. of pyridine hydrobromide perbromide ($C_5H_5N\cdot NBr\cdot Br_2$) is added. The mixture is stirred at room temperature for 3 hours, after which time the acetic acid is distilled off under reduced pressure. The residue is shaken well with water and acetic acid. The ethyl acetate layer is taken, washed with water and dried over anhydrous sodium sulfate. The solvent is then distilled off under reduced pressure and the residue is crystallized from ethyl acetate-n-hexane. The procedure yields 4.9 g. of 6-benzyloxy-2-bromo-5-cyano-3,4-dihydro-1-(2H)-naphthalenone as colorless needles melting at 115°–116° C.

Elemental analysis: for $C_{18}H_{14}O_2NBr$; Calculated C, 60.69; H, 3.96; N, 3.93; Found C, 60.90; H, 3.81; N, 3.80.

REFERENCE EXAMPLE 14

In anhydrous benzene are dissolved 2.0 g. of 6-benzyloxy-2-bromo-5-cyano-3,4-dihydro-1(2H)-napthalenone and 2.0 g. of N-methylbenzylamine and the solution is refluxed in a current of nitrogen for 5 hours. After cooling, in nitrogen streams, ethyl acetate and water are added, and the mixture is shaken well. The organic layer is taken, washed with water and aqueous sodium chloride, dried over anhydrous sodium sulfate, and concentrated under reduced pressure. The solution is cooled with ice and the resulting yellow crystals are recovered by filtration and rinsed with ethyl acetate. The procedure yields 1.3 g. of 6-benzyloxy-2-N-benzyl-N-methylamino-5-cyano-3,4-dihydro-1(2H)-naphthalenone. Crystallization from ethyl acetate yields light-brown platelets melting at 142°–143° C.

Elemental analysis; for $C_{26}H_{24}O_2N_2$; Calculated C, 78.76; H, 6.10; N, 7.07; Found C, 78.62; H, 5.94; N, 7.05.

REFERENCE EXAMPLE 15

In 40 ml. of ethanol is dissolved 5.0 g. of 6-benzyloxy-5-formyl-3,4-dihydro-1(2H)-naphthalenone, followed by addition of 5.0 g. of hydroxylamine hydrochloride and 6.0 g. of anhydrous sodium acetate. The mixture is refluxed for 4 hours, after which time it is poured in 200 ml. of ice-water. The precipitation formed is recovered by filtration, rinsed with water, dried and recrystallized from benzenethyl acetate. The procedure yields 5.2 g. of 6-benzyloxy-5-formyl-3,4-dihydro-1(2H)-naphthalenone 1,5-dioxime as colorless prisms melting at 162°–164° C.

Elemental analysis; for $C_{18}H_{18}O_3N_2$; Calculated C, 69.66; H, 5.85; N, 9.03; Found C, 69.53; H, 5.48; N, 8.85.

REFERENCE EXAMPLE 16

In 8 ml. of anhydrous pyridine is dissolved in 1.5 g. of 6-benzyloxy-5-formyl-3,4-dihydro-1(2)-naphthalenone 1,5-dioxime and, under cooling with ice, 1.9 g. of benzenesulfonyl chloride is added dropwise. The mixture is stirred and cooled with ice for 2 hours and, then, allowed to stand in a refrigerator overnight. The reaction mixture is poured in 100 ml. of ice-water and the resulting precipitate is recovered by filtration and rinsed with water. The residue is dissolved in 100 ml. of benzene and washed with dilute hydrochloric acid and, then, with water. After drying over anhydrous sodium sulfate, the solvent is distilled off under reduced pressure and the residue is recrystallized from benzene. the procedure yields 1.6 g. of 1-benzenesulfonyl oxyimino-6-benzyloxy-5-cyano-1,2,3,4-tetrahydronaphthalene as colorless needles melting at 161°–163° C.

Elemental analysis; for $C_{24}H_{20}O_4N_2S$; Calculated C, 66.65; H, 4.66; N, 6.48; Found C, 66.53; H, 4.40; N, 6.47.

REFERENCE EXAMPLE 17

In a manner similar to that of Reference Example 9, 6.5 g. of 1 benzenesulfonyloxyimino-6-benzyloxy-5-cyano-1,2,3,4-tetrahydronaphthalene is converted to 4.0 g. of 2-amino-6-benzyloxy-5-cyano-3,4-dihydro-1(2H)-napthalenone hydrochloride. Recrystallization from methanol-ethyl acetate yields colorless needles melting at 208°–213° C(decomp.).

Elementanalysis; for $C_{18}H_{16}O_2N_2 \cdot HCl \cdot H_2O$; Calculated C, 62.33; H, 5.52; N, 8.08; Found C, 61.98; H, 5.41; N, 7.95.

Mass spectrum, m/e: 292 ($M^+$-HCl)

REFERENCE EXAMPLE 18

In a manner similar to that of Reference Example 10, 3.6 g. of 2-amino-6-benzyloxy-5-cyano-3,4-dihydro-1(2H)-naphthalenone hydrochloride is converted to 3.0 g. of 6-benzyloxy-5-cyano-2-isopropylamino-3,4-dihydro-1(2H)-naphthalenone hydrochloride as colorless prisms melting at 195°–199° C (decomp.).

Elemental analysis; for $C_{21}H_{22}O_2N_2 \cdot HCl \cdot \frac{1}{2}H_2O$; Calculated C, 66.39; H, 6.37; N, 7.37; Found C, 66.34; H, 6.24; N, 7.35.

REFERENCE EXAMPLE 19

In a mixture of 10 ml. of ethanol and 4 ml. of water is dissolved 200 mg. of trans-5-aminomethyl-6-bemnzyloxy-1-hydroxy-2-isopropylamino-1,2,3,4-tetrahydronaphthalene hydrochloride, followed by the addition of 50 mg. of potassium cyanide. The mixture is refluxed for 3 hours. The reaction mixture is concentrated under reduced pressure and the residue is rendered alkaline with saturated aqueous sodium chloride solution and aqueous sodium hydrogen carbonate solution. The mixture is then extracted with ethyl acetate. The ethyl acetate layers are pooled, washed with saturated aqueous sodium chloride solution and dried over anhydrous sodium sulfate. The solvent is distilled of under reduced pressure and the residue is recrystallized from ethanol-ethyl acetate. The procedure yields 103 mg. of trans-6-benzyloxy-1-hydroxy-2-isopropylamino-5-ureidomethyl-1,2,3,4-tetrahydronaphthalene as white crystals melting at 202°–204° C (decomp.).

elemental analysis; for $C_{22}H_{29}O_3N_3$; Calculated C, 68.90; H, 7.62; N, 10.96; Found C, 68.56; H, 7.95; N, 11.15.

REFERENCE EXAMPLE 20

Together with 13 g. of sodium acetate, 13 g. of hydroxylamine hydrochloride and 70 ml. of ethanol, 60 g. of 6-benzyloxy-5-methoxymethyl-3,4-dihydro-1(2H)-naphthalenone is heated on reflux for 4 hours. After cooling, the reaction mixture is poured in 200 ml. of ice-water. The resulting precipitate is recovered by filtration and recrystallized from ethanol. The procedure provides 6.0 g. of 6-benzyloxy-5-methoxymethyl-3,4-dihydro-1(2H)-naphthalenone 1-oxime as colorless prisms melting at 138°–140° C.

Elemental analysis; for $C_{19}H_{21}O_3$; Calculated C, 73.29; H, 6.80; N, 4.50; Found C, 72.90; H, 6.61; N, 4.30.

REFERENCE EXAMPLE 21

In manners similar tothose of Reference Examples 8 and 9, 6-benzyloxy-5-methoxymethyl-3,4-dihydro-1(2H)-naphthalenone 1-oxime is converted to 2-amino-6-benzyloxy-5-methoxy methyl-3,4-dihydro-1(2H)-naphthalenone hydrochloride. Colorless prisms melting at 180°–185° C(decomp.).

Element analysis; for $C_{19}H_{21}O_3N \cdot HCl$; Calculated C, 65.61; H, 6.38; N, 4.03; Found C, 65.13; H, 6.01; N, 4.25.

REFERENCE EXAMPLE 22

In a manner similar to that of Reference Example 10, 710 mg. of 2-amino-6-benzyloxy-5-methoxymethyl-3,4-dihydro-1(2H)-naphthalenone hydrochloride is converted to 420 mg. of 6-benzyloxy-2-isopropylamino-5-methoxymethyl-3,4-dihydro-1(2H)-naphthalenone hydrochloride. Colorless prisms melting at 175°–180° C (decomp.).

Elemental analysis: for $C_{22}H_{27}O_3N \cdot HCl \cdot 2/3H_2O$; Calculated C, 65.74; H, 7.36; N, 3.48; Found C, 65.60; H, 6.93; N, 3.55.

REFERENCE EXAMPLE 23

In 40 ml. of 0.2N hydrochloric acid is dissolved 6-benzyloxy-2-isopropylamino-5-methoxymethyl-3,4-dihydro-1(2H)-naphthalenone hydrochloride and, under nitrogen sparging, the solution is heated on reflux for 20 hours. The reaction mixture is treated with activated carbon and concentrated under reduced pressure at a temperature not exceeding 40° C. The residue is recrystallized from ethanol-ether. The procedure yields 230 mg. of 6-hydroxy-5-hydroxymethyl-2-isopropylamino-3,4-dihydro-1(2H)-naphthalenone hydrochloride as colorless crystals melting at 200°–205° C(decomp.).

Elemental analysis; for $C_{14}H_{19}O_3N \cdot HCl \cdot \frac{1}{2}H_2O$; Calculated C, 53.68; H, 6.43; N, 4.47; Found C, 53.42; H, 6.55; N, 4.76.

REFERENCE EXAMPLE 24

In 60 ml. of concentrated sulfuric acid is dissolved 15 g. of 6-hydroxy-3,4-dihydro-1(2H)-naphthalenone and, at $-5° - 0°$ C, 20 ml. of mixed acid (prepared from 12 ml. of concentrated sulfuric acid and 8 ml. of concentrated nitric acid) is added dropwise with vigorous stirring. After the dropwise addition has been completed, the mixture is poured in ice-water and the resulting precipitate is recovered by filtration. It is then dissolved in ethyl acetate, washed with water, dried and concentrated to dryness under reduced pressure. The residue is rinsed with benzene. The procedure yields 8.0 g. of 6-hydroxy-5-nitro-3,4-dihydro-1(2H)-naphthalenone as colorless prisms melting at 196°–198° C.

Elemental analysis; for $C_{10}H_9O_4N$; Calculated C, 57.97; H, 4.38; N, 6.76; Found C, 58.10; H, 4.26; N, 6.70.

REFERENCE EXAMPLE 25

In a manner similar to that of Reference Example 3, 14 g. of 6-hydroxy-5-nitro-3,4-dihydro-1(2H)-naphthalenone is converted to 18 g. of 6-benzyloxy-5-nitro-3,4-dihydro-1(2H)-naphthalenone as colorless prisms melting at 105°–107° C.

Elemental Analysis; for $C_{17}H_{15}O_4N$; Calculated C, 68.67; H, 5.08; N, 4.71; Found C, 68.60; H, 4.96; N, 4.45.

REFERENCE EXAMPLE 26

To a solution of 18 g. of 6-benzyloxy-5-nitro-3,4-dihydro-1(2H)-naphthalenone in 240 ml. of ethanol is added 2 g. of Raney nickel and, under reflux and stirring, a solution of 14 g. of hydrazine hydrate in 30 ml. of ethanol is added dropwise. After the dropwise addition, the Raney nickel is filtered off and the filtrate is concentrated under reduced pressure to about half its initial volume. The concentrate is allowed to stand in a refrigerator. The procedure yields 14 g. of 5-amino-6-benzyloxy-3,4-dihydro-1(2H)-naphthalenone as colorless needles melting at 124°–126° C.

Elemental analysis; for $C_{17}H_{17}O_2N$; Calculated C, 76.38; H, 6.41; N, 5.24; Found, C, 76.07; H, 6.34; N, 4.98.

REFERENCE EXAMPLE 27

To a solution of 13 g. of 5-amino-6-benzyloxy-3,4-dihydro-1(2H)-naphthalenone in 100 ml. of pyridine is added 6 g. of methanesulfonyl chloride in droplets.

The mixture is stirred at room temperature for 3 hours, after which time it is added to ice-water. The resulting crystals are recovered by filtration, rinsed with water, dried and recrystallized from ethanol. The procedure yields 15 g. of 6-benzyloxy-5-methanesulfonylamino-3,4-dihydro-1-(2H)-naphthalenone as colorless needles melting at 184°–185° C.

Elemental analysis; for $C_{18}H_{19}O_4NS$; Calculated C, 62.60; H, 5.55; N, 4.06; Found C, 62.57; H, 5.54; N, 3.89.

REFERENCE EXAMPLE 28

In a manner substantially similar to that of Reference Example 3, 36 g. of 6-benzyloxy-5-methanesulfonylamino-3,4-dihydro-1(2H)-naphthalenone is converted to 37 g. of 6-benzyloxy-5-(N-benzyl-N-methanesulfonylamino)-3,4-dihydro-1(2H)-naphthalenone. Pale-yellow prisms melting at 206°–208° C.

Elemental analysis; for $C_{25}H_{25}O_4NS$; Calculated C, 68.95; H, 5.79; N, 3.22; Found C, 68.65; H, 5.71, N, 2.80.

REFERENCE EXAMPLE 29

In manners similar to those of Examples 20 and 21, 6-benzyloxy-5-(N-benzyl-N-methaneslfonylamino-3,4-dihydro-1(2H)-naphthalenone is converted to 2-amino-6-benzyloxy-5-(N-benzenyl-N-methanesulfonylamino)-3,4-dihydro-1(2H)-napthalenone hydrochloride. Colorless needles melting at 193°–195° C.

Elemental analysis; for $C_{25}H_{26}O_4N_2S \cdot HCl$; Calculated C, 61.66; H, 5.59; N, 5.75; Found C, 61.78; H, 5.57; N, 5.60.

REFERENCE EXAMPLE 30

In manners similar to those of Reference Examples 20 and 21, 6-benzyloxy-5-nitro-3,4-dihydro-1(2H)-naphthalenone is converted to 2-amino-6-benzyloxy-5-nitro-3,4-dihydro-1(2H)-naphthalenone hydrochloride. Colorless scales melting at 220°–222° C.

Elemental analysis; for $C_{17}H_{16}O_4N_2 \cdot HCl$; Calculated C, 58.54; H, 4.91; N, 8.03; Found C, 58.60; H, 5.16; N, 7.64.

REFERENCE EXAMPLE 31

To a solution of 7.0 g. 2-amino-6-benzyloxy-5-nitro-3,4-dihydro-1(2H)-naphthalenone hydrochloride are added 6.1 g. of benzaldehyde and 1.5 g. of sodium cyanoborohydride. The mixture is stirred at room temperature for 5 hours and the resulting crystals are recovered by filtration, rinsed with water and dried. The procedure provides 5.4 g. of 2-benzylamino-6-benzyloxy-5-nitro-1(2H)-naphthalenone as pale-yellowish prisms. The crystals are dissolved in alcoholic hydrochloric acid and the crystals formed on addition of ethyl ether are recovered by filtration. The procedure provides the hydrochloride of the above-mentioned compound as pale yellowish prisms melting at 173°–176° C.

Elemental analysis; for $C_{24}H_{22}O_4N_2 \cdot HCl$; Calculated C, 65.67; H, 5.28; N, 6.38; Found, C, 65.62; H, 5.18; N, 6.30.

REFERENCE EXAMPLE 32

In a mixture of 3 ml. of formic acid and 5 ml. of acetic anhydride is dissolved 1.0 g. of cis-5-amino-2-(N-benzyl-N-methylamino)-6-benzyloxy-1-hydroxy-1,2,3,4-tetrahydronaphthalene and the solution is allowed to stand at room temperature overnight. The reaction mixture is concentrated under reduced pressure and the residue is dissolved in 50 ml of methanol. Following addition of 2 ml. of water and 2 g. of sodium carbonate, the solution is stirred for 1 hour. The reaction mixture is concentrated under reduced pressure and the residue is extracted with ethyl acetate. After drying, the extract is fractionally purified by column chromatography on silica gel, elution being carried out with a solvent mixture of acetone and benzene (1:1). The procedure provides 0.4 g. of cis-2-(N-benzyl-N-methylamino)-6-benzyloxy-5-N-formylamino-1-hydroxy-1,2,3,4-tetrahydronaphthalene.

Elemental analysis; for $C_{26}H_{28}O_3N_2$; Calculated C, 74.97; H, 6.78; N, 6.73; Found C, 74.46; H, 6.56; N, 6.69.

REFERENCE EXAMPLE 33

In a manner similar to that of Reference Example 32, 1.0 g. of trans-5-amino-2-(N-benzyl-N-methylamino)-6-benzyloxy-1-hydroxy-1,2,3,4-tetrahydronaphthalene is converted to 0.3 g. of trans-2-(N-benzyl-N-methylamino)-6-benzyloxy-5-N-formylamino-1-hydroxy-1,2,3,4-tetrahydronaphthalene.

Infrared absorption spectrum: 1690 cm$^{-1}$(carbonyl).

REFERENCE EXAMPLE 34

To a solution of 0.5 g. of cis-5-amino-2-(N-benzyl-N-methylamino)-6-benzyloxy-1-hydroxy-1,2,3,4-tetrahydronaphthalene in 5 ml. of methanol is added 1 ml. of acetic acid, followed by vigorous stirring. To this solution is added 3 ml. of an aqueous solution of 0.5 g. potassium cyanate, and the mixture is stirred at room temperature for 1 hour. The reaction mixture is concentrated under reduced pressure and, following the addition of water, the residue is rendered alkaline with a saturated aqueous solution of sodium hydrogen carbonate. The resulting oily precipitate is extracted with ethyl acetate. The extract is washed with water, dried and concentrated under reduced pressure. The procedure provides 0.5 g. of cis-2-(N-benzyl-N-methylamino)-6-benzyloxy-1-hydroxy-5-ureido-1,2,3,4-tetrahydronaphthalene.

Infrared absorption spectrum: 1685 cm$^{-1}$(carbonyl).

REFERENCE EXAMPLE 35

In a manner similar to that of Reference Example 34, 0.5 g. of trans-5-amino-2-(N-benzyl-N-methylamino)-6-benzyloxy-1-hydroxy-1,2,3,4-tetrahydronaphthalene is converted to 0.5 g. of trans-2-(N-benzyl-N-methylamino)-6-benzyloxy-1-hydroxy-5-ureido-1,2,3,4-tetrahydronaphthalene.

Infrared absorption spectrum: 1690 cm$^{-1}$(carbonyl).

REFERENCE EXAMPLE 36

In a manner similar to that of Reference Example 10, 6-benzyloxy-2-isopropylamino-5-nitro-3,4-dihydro-1(2H)-naphthalenone hydrochloride is obtained from 2-amino-6-benzyloxy-5-nitro-3,4-dihydro-1(2H)-naphthalenone hydrochloride and acetone. Yellowish green prisms melting at 225°–227° C.

Elemental analysis; for $C_{20}H_{22}O_4N_2 \cdot HCl$; Calculated C, 61.45; H, 5.93; N, 7.17; Found C, 61.08; H, 5.77; N, 7.08.

REFERENCE EXAMPLE 37

In a manner similar to that of Reference Example 34, 0.6 g. of 5-amino-6-benzyloxy-1-hydroxy-2-isopropylamino-1,2,3,4-tetrahydronaphthalene is converted to 0.5 g. of 6-benzyloxy-1-hydroxy-2-isopropylamino-5-ureido-1,2,3,4-tetrahydronaphthalene.

Infrared absorption spectrum: 1685 cm$^{-1}$(carbonyl)

REFERENCE EXAMPLE 38

A solution of 13.5 g. of 5-amino-6-benzyloxy-3,4-dihydro-1(2H)-naphthalenone in a mixture of 100 ml. dimethylformamide and 22 ml. concentrated hydrochloric acid is cooled to 0° C, and 10 ml. of an aqueous solution of 3.5 g. sodium nitrite is added dropwise with constant stirring. During this operation, the reaction temperature is maintained at 5° C or less. The diazo compound formed is added dropwise to a mixture of 7.0 g. cuprous chloride and 22 ml. concentrated hydrochloric acid. After the dropwise addition has been completed, the reaction mixture is maintained at temperature for 1 hour and, following the addition of water, the precipitate is extracted with ethyl acetate. The extract is washed with water and dried. The ethyl acetate is then distilled off under reduced pressure and the residue is purified by column chromatography on silica gel (eluted with benzene). The procedure provides 4.0 of 6-benzyloxy-5-chloro-3,4-dihydro-1(2H)-naphthalenone as colorless scales melting at 99°–100° C.

Elemental analysis; for $C_{17}H_{15}O_2Cl$; Calculated C, 71.20; H, 5.27; Found C, 71.33; H, 4.83.

REFERENCE EXAMPLE 39

In manners similar to those of Reference Examples 20 and 21, 6-benzyloxy-5-chloro-3,4-dihydro-1(2H)-naphthalenone is converted to 2-amino-6-benzyloxy-5-chloro-3,4-dihydro-1-(2H)-naphthalenone hydrochloride. Colorless needles melting at 251°–253° C.

Elemental analysis; for $C_{17}H_{16}O_2NCl \cdot HCl$; Calculated C, 60.36; H, 5.07; N, 4.14; Found C, 59.98; H, 4.94; N, 4.36.

REFERENCE EXAMPLE 40

To a solution of 7.0 g. 6-benzyloxy-5-methanesulfonylamino-3,4-dihydro-1(2H)-naphthalenone in 90 ml. dioxane is added 18.9 g. of sodium methoxide and the mixture is stirred at 0° C for 30 minutes. To this solution is added 4.7 g. of ethyl formate dropwise and the reaction is carried out at 0°–5° C for 4 hours. Following the addition of water, the reaction mixture is rendered acidic with acetic acid and the resulting oily precipitate is extracted with benzene. The extract is washed with water and dried. The benzene is distilled off under reduced pressure and the residue is recrystallized from ethyl ether. The procedure provides 8.2 g. of 6-benzyloxy-2-formyl-5-methanesulfonylamino-3,4-dihydro-1(2H)-naphthalenone as colorless prisms melting at 135°–138° C.

Elemental analysis; for $C_{19}H_{19}O_5NS$; Calculated C, 61.12; H, 5.13; N, 3.75; Found C, 61.31; H, 5.12; N, 3.70.

REFERENCE EXAMPLE 41

In a mixture of 65 ml. dichloromethane, 310 ml. acetic acid and 15.5 ml. water is dissolved 8.2 g. of 6-benzyloxy-2-formyl-5-methanesulfonylamino-3,4-dihydro-1(2H)-naphthalenone and, under cooling with ice, 41 ml. of a solution of 2.7 g. sodium nitrite in water is added dropwise. After the dropwise addition has been completed, the mixture is stirred for 2 hours. Following the addition of water, the reaction mixture is extracted with dichloromethane. The extract is washed with water and dried. The dichloromethane is then distilled off and the residue is recrystallized from ethyl acetate. The procedure provides 3.0 g. of 6-benzyloxy-5-methanesulfonylamino-2-oxyimino-3,4-dihydro-1(2H)-naphthalenone as yellow prisms melting at 225°–227° C.

Elemental analysis; for $C_{18}H_{18}O_5N_2S$; Calculated C, 57.75; H, 4.85; N, 7.48; Found C, 57.70; H, 4.73; N, 6.82.

REFERENCE EXAMPLE 42

To a solution of 0.2 g. 6-benzyloxy-2-bromo-5-nitro-3,4-dihydro-1(2H)-naphthalenone in 2 ml. dimethylformamide are added 90 mg. of phloroglucinol and 75 mg. of sodium nitrite and the mixture is stirred at room temperature for 2 hours. Following the addition of water, the reaction mixture is extracted with ethyl acetate and the extract is washed with water, dried and concentrated under reduced pressure. The residue is recrystallized from a mixture of ethanol and petroleum ether. The procedure provides 0.17 g. of 6-benzyloxy-2,5-dinitro-3,4-dihydro-1(2H)-naphthalenone as pale-yellow needles melting at 97°–98° C.

Elemental analysis; for $C_{17}H_{14}O_6N_2$; Calculated C, 59.64; H, 4.12; N, 8.18; Found C, 59.35; H, 3.71; N, 7.71.

REFERENCE EXAMPLE 43

In 20 ml. of ethanol is dissolved 1.0 g. of 2-amino-6-benzyloxy-5-methoxymethyl-3,4-dihydro-1(2H)-naphthalenone hydrochloride, followed by the addition of 10 ml. concentrated hydrochloric acid. The mixture is heated at 60° C for 3 hours. The reaction mixture is concentrated under reduced pressure and the residue is recrystallized from methanol-ethyl acetate. The procedure provides 930 mg. of 2-amino-6-benzyloxy-5-chloromethyl-3,4-dihydro-1(2H)-naphthalenone hydrochloride as colorless prisms melting at 175°–179° C (decomp.).

Elemental analysis; for $C_{18}H_{18}ClNO_2 \cdot HCl$; Calculated C, 61.37; H, 5.44; N, 3.98; Found C, 61.53; H, 5.01; N, 3.54.

REFERENCE EXAMPLE 44

Together with 20 ml. glacial acetic acid, 1 ml. acetic anhydride and 500 mg. sodium acetate, 900 mg. of 2-amino-6-benzyloxy-5-chloromethyl-3,4-dihydro-1(2H)-naphthalenone hydrochloride is refluxed for 3 hours. The reaction mixture is concentrated under reduced pressure and, following the addition of ethyl acetate and water, the concentrate is extracted with ethyl acetate. The ethyl acetate layers are pooled, washed with water and dried over anhydrous sodium sulfate. The solvent is distilled off under reduced pressure and the residue is recrystallized from ethyl acetate. The procedure provides 350 mg. of 2-acetylamino-5-acetoxymethyl-6-benzyloxy-3,4-dihydro-1(2H)-naphthalenone as colorless needles melting at 192°–194° C.

Elemental analysis; for $C_{22}H_{23}NO_5$; Calculated C, 69.27; H, 6.08; N, 3.67; Found C, 69.23; H, 5.98; N, 3.63.

REFERENCE EXAMPLE 45

Together with 200 ml. of acetic anhydride, 200 ml. of glacial acetic acid and 15 g. of sodium acetate, 30 g. of 5-chloromethyl-6-hydroxy-3,4-dihydro-1(2H)-naphthalenone is heated on reflux for 2 hours. After cooling, the reaction mixture is filtered off and the filtrate is concentrated under reduced pressure. The residue is dissolved in 200 ml. of benzene, washed with water and dried over anhydrous sodium sulfate. The solvent is distilled off under reduced pressure and the residue is distilled under reduced pressure. The fraction boiling at 193°–195° C (1 mmHg) is recovered. The above procedure provides 30 g. of 6-acetoxy-5-acetoxymethyl-3,4-dihydro-1(2H)-naphthalenone as a colorless oil.

Elemental analysis; for $C_{15}H_{16}O_5$; Calculated C, 65.21; H, 5.84; Found C, 65.32; H, 5.54.

REFERENCE EXAMPLE 46

To an ethanolic solution of sodium ethoxide, prepared from 6.0 g. sodium metal and 300 ml. anhydrous ethanol, there is added a solution of 15 g. 6-acetoxy-5-acetoxymethyl-3,4-dihydro-1(2H)-naphthalenone in 20 ml. ethanol dropwide at 50°–60° C and under stirring. The mixture is stirred at 40°–50° C, and then at 50°–60° C 45 g. of dimethyl sulfate is added dropwise, followed by stirring at the same temperature for 2 hours. After cooling, the reaction mixture is concentrated under reduced pressure and the residue is dissolved in ethyl acetate, washed with water and dried over anhydrous sodium sulfate. The solvent is distilled off and the residue is recrystallized from cyclohexane. The procedure provides 8.0 g. of 5-ethoxymethyl-6-methoxy-3,4-dihydro-1(2H)-naphthalenone as colorless needles melting at 85°–86° C.

Elemental analysis; for $C_{13}H_{16}O_3$; Calculated C, 71.77; H, 7.74; Found C, 71.72; H, 7.92.

REFERENCE EXAMPLE 47

In manners similar to those of Reference Examples 20 and 21, 5-ethoxymethyl-6-methoxy-3,4-dihydro-1(2H)-naphthalenone is converted to 2-amino-5-ethoxymethyl-6-methoxy-3,4-dihydro-1(2H)-naphthalenone hydrochloride. Colorless prisms melting at 190°–198° C(decomp.).

Elemental analysis; for $C_{14}H_{19}NO_3 \cdot HCl \cdot \frac{1}{2}H_2O$; Calculated C, 57.04; H, 7.18; N, 4.75; Found C, 56.72; H, 6.97; N, 4.69.

REFERENCE EXAMPLE 48

To 100 ml. of ethanol are added 10 g. of 5-chloromethyl-6-hydroxy-3,4-dihydro-1(2H)-naphthalenone and 5.4 g. of sodium methanesulfinate, and the mixture is heated on reflux for 2 hours. Then, the reaction mixture is concentrated and the residue is dissolved in chloroform and washed with water. The chloroform layer is dried in the conventional manner and the chloroform is distilled off. The procedure provides 5-methanesulfonylmethyl-6-hydroxy-3,4-dihydro-1(2H)-naphthalenone melting at 225°–230° C(decomp.).

Elemental analysis; for $C_{12}H_{14}O_4S$; Calculated C, 56.68; H, 5.55; Found C, 56.90; H, 5.59.

REFERENCE EXAMPLE 49

In a manner similar to that of Reference Example 3, 5-methanesulfonylmethyl-6-hydroxy-3,4-dihydro-1(2H)-naphthalenone is converted to 5-methanesulfonylmethyl-6-benzyloxy-3,4-dihydro-1(2H)-naphthalenone. Melting point: 159.0°–160.5° C.

Elemental analysis; for $C_{19}H_{20}O_4S$; Calculated C, 66.26; H, 5.85; Found C, 65.94; H, 5.72.

REFERENCE EXAMPLE 50

In manners similar to those of Reference Example 40 and 41, 5-methanesulfonylmethyl-6-benzyloxy-3,4-dihydro-1(2H)-naphthalenone is converted to 2-isonitroso-5-methanesulfonylmethyl-6-benzyloxy-3,4-dihydro-1(2H)-naphthalenone. Melting point: 170°–180° C(decomp.).

Elemental analysis; $C_{19}H_{19}O_5NS$; Calculated C, 61.11; H, 5.13; N, 3.75; Found C, 61.38; H, 5.28; N, 3.61.

REFERENCE EXAMPLE 51

In a mixture of 40 ml. ethanol and 20 ml. tetrahydrofuran is dissolved 1.3 g. of 6-benzyloxy-2-(N-benzyl-N-methylamino)-5-cyano-3,4-dihydro-1(2H)-naphthalenone and, at room temperature, 0.25 g. of sodium borohydride is added. The mixture is stirred for 4 hours, after which time the solvent is distilled off under reduced pressure. To the residue are added benzene and water and, after shaking well, the benzene layer is taken, washed with water and dried over anhydrous sodium sulfate. The solvent is then distilled off and the residue is subjected to column chromatography on silica gel. Upon elution with chloroform, there emerges 0.32 g. of trans-6-benzyloxy-2-N-benzyl-N-methylamino-5-cyano-1-hydroxy-1,2,3,4-tetrahydronaphthalene and 0.15 g. of cis-6-benzyloxy-2-(N-benzyl-N-methylamino)-5-cyano-1-hydroxy-1,2,3,4-tetrahydronaphthalene. The trans-compound is recrystallized from ethyl acetate-n-hexane to obtain colorless prisms melting at 140°–141° C. This product is treated with ethanolic hydrochloric acid and recrystallized from ethanol. This procedure provides colorless needles of the corresponding hydrochloride melting at 234°–236° C (decomp.). The cis-compound is recrystallized from ethyl acetate-n-hexane to obtain colorless platelets melting at 141°–142° C. This product, when treated in the same manner as the trans- compound, yields the corresponding hydrochloride as colorless prisms melting at 245°–247° C(decomp.).

Elemental analysis:

Trans-compound; $C_{26}H_{26}O_2N_2$; Calculated C, 78.36; H, 6.58; N, 7.03; Found C, 78.23; H, 6.42; N, 6.97.

Trans-hydrochloride; $C_{26}H_{26}O_2N_2 \cdot HCl$; Calculated C, 71.79; H, 6.26; N, 6.44; Found C, 71.76; H, 6.15; N, 6.43.

Cis-compound; $C_{26}H_{26}O_2N_2$; Calculated C, 78.36; H, 6.58 N, 7.03; Found C, 78.09; H, 6.38 N, 7.29.

Cis-hydrochloride; $C_{26}H_{26}O_2N_2 \cdot HCl$; Calculated C, 71.79; H, 6.26; N, 6.44; Found C, 71.78; H, 6.26; N, 6.63.

REFERENCE EXAMPLE 52

In manners similar to those of Reference Example 13, 14 and 51, 6-benzyloxy-5-nitro-3,4-dihydro-1(2H)-naphthalenone is converted to trans-2-(N-benzyl-N-methylamino)-6-benzyloxy-1-hydroxy-5-nitro-1,2,3,4-tetrahydronaphthalene hydrochloride melting at 251°–253° C and cis-2-(N-benzyl-N-methylamino)-6-benzyloxy-1-hydroxy-5-nitro-1,2,3,4-tetrahydronaphthalene hydrochloride, melting at 235°–236° C.

REFERENCE EXAMPLE 53

In the manners similar to those of Reference Example 13, 14 and 51, 6-benzyloxy-5-methoxycarbonyl-3,4-dihydro-1(2H)-naphthaleone is converted to trans- and cis-6-benzyloxy-5-methoxycarbonyl-2-(N-benzyl-N-methylamino)-1-hydroxy-1,2,3,4,-tetrahydronaphthalene hydrochloride. Melting points: trans-compound, 225°–226° C; cis-compound, 245°–246° C(decomp.).

REFERENCE EXAMPLE 54

To 20 ml. of tetrahydrofuran is added 120 mg. of lithium aluminum hydride and, under nitrogen sparging, a solution of 500 mg. trans-6-benzyloxy-5-cyano-1-hydroxy-2-isopropylamino-1,2,3,4-tetrahydronaphthalene in 10ml. anhydrous tetrahydrofuran is added dropwise. The mixture is refluxed for 2 hours, at the end of which time the excess lithium aluminum hydride is decomposed with ethyl acetate. Following the addition of saturated aqueous sodium chloride, the reaction mixture is extracted with ethyl acetate. The ethyl acetate layers are pooled, washed with saturated aqueous sodium chloride and dried over anhydrous sodium sulfate. The solvent is distilled off under reduced pressure and the residue is dissolved in ethyl acetate and treated with alcoholic hydrochloric acid. The resulting hydrochloride is recrystallized from isopropyl alcohol-ethyl acetate. The procedure provides 490 mg. of trans-5-aminomethyl-6-benzyloxy-1-hydroxy-2-isopropylamino-1,2,3,4-tetrahydronaphthalene hydrochloride as white crystalline powders.

REFERENCE EXAMPLE 55

To a solution of 3.0 g. cis-2-(N-benzyl-N-methylamino)-6-benzyloxy-1-hydroxy-5-nitro-1,2,3,4-tetrahydronaphthalene hydrochloride in 30ml. ethanol is added 1.0 g. of Raney nickel. The mixture is refluxed under stirring. Then, a solution of 3.0 g. hydrazine hydrate in 30 ml. ethanol is added dropwise. After the dropwise addition has been completed, the reaction is further continued for 30 minutes. The Raney nickel is filtered off and the filtrate is concentrated under reduced pressure, whereupon crystals separate. The crystals are recovered by filtration, rinsed with a small amount of ethanol and dried. The procedure provides 1.8 g. of cis-5-amino-2-(N-benzyl-N-methylamino)-1-hydroxy-6-benzyloxy-1,2,3,4-tetrahydronaphthalene as colorless prisms melting at 148°–150° C.

Elemental analysis; for $C_{25}H_{28}O_2N_2$; Calculated C, 77.29; H, 7.27; N, 7.21; Found C, 77.14; H, 7.35; N, 7.26.

In a manner similar to that mentioned above, trans-2-(N-benzyl-N-methylamino)-6-benzyloxy-1-hydroxy-5-nitro-1,2,3,4-tetrahydronaphthalene hydrochloride is reduced to obtain trans-5-amino-2(N-benzyl-N-methylamino)-6-benzyloxy-1-hydroxy-1,2,3,4-tetrahydronaphthalene. Colorless prisms melting at 124°–126° C.

REFERENCE EXAMPLE 56

In a manner similar to that of Reference Example 55, 2.0 g. of 6-benzyloxy-1-hydroxy-2-isopropylamino-5-nitro-1,2,3,4-tetrahydronaphthalene hydrochloride is reduced to obtain 0.7 g. of 5-amino-6-benzyloxy-1-hydroxy-2-isopropylamino-1,2,3,4-tetrahydronaphthalene as colorless prisms melting at 218°–220° C.

Elemental analysis; for $C_{20}H_{26}O_2N_2$; Calculated C, 73.56; H, 8.03; N, 8.58; Found C, 73.28; H, 8.00; N, 8.78.

REFERENCE EXAMPLE 57

In 30 ml. of ethanol is dissolved 2.96 g. of 6-benzyloxy-5-methoxycarbonyl-3,4-dihydro-1(2H)-naphthalenone and, under stirring at room temeperature, 400 mg. of sodium borohydride is added. The mixture is stirred for 3 hours, after which time it is concentrated under reduced pressure. Following the addition of water and ethyl acetate, the ethyl acetate layer is washed with water and dried. The solvent is then distilled off to recover 2.8 g. of 6-benzyloxy-1-hydroxy 5-methoxycarbonyl-1,2,3,4-tetrahydronaphthalene. This product is dissolved in 50 ml. of benzene, followed by the addition of 10 mg. of potassium hydrogen sulfate. The mixture is reflexed and the water formed is removed. After 2 hours, the inorganic matter is filtered off and the solvent is distilled off under reduced pressure. The residue is recrystallized from methanol. The procedure provides 2.2 g. of 6-benzyloxy-5-methoxycarbonyl-3,4-dihydronaphthalene as colorless needles melting at 100°–101° C.

Elemental analysis; for $C_{19}H_{18}O_3$; Calculated C, 77.53; H, 6.16; Found C, 77.34; H, 5.94.

REFERENCE EXAMPLE 58

In a mixture of 30 ml. dimethylsulfoxide and 1 ml. water is dissolved 1.5 g. of 6-benzyloxy-5-methoxycarbonyl-3,4-dihydronaphthalene and, with the addition of 1.1 g. of N-bromosuccinimide, the solution is stirred at room temperature for 30 minutes. The reaction mixture is poured in water and extracted with ethyl ether. The ethereal solution is washed with water and dried. The solvent is then distilled off under reduced pressure and the residue is recrystallized from benzene-n-hexane. The procedure provides 1.65 g. trans-6-benzyloxy-2-bromo-1-hydroxy-5-methoxycarbonyl-1,2,3,4-tetrahydronaphthalene as colorless needless melting at 124°–125° C.

Elemental analysis; for $C_{19}H_{19}O_4Br$; Calculated C, 58.32; H, 4.89; Found C, 58.24; H, 4.59.

REFERENCE EXAMPLE 59

In 20 ml. of anhydrous benzene is dissolved 3.0 g. of trans-6-benzyloxy-2-bromo-1-hydroxy-5-methoxycarbonyl-1,2,3,4-tetrahydronaphthalene, followed by the addition of 5 g. of anhydrous potassium carbonate and 1.0 g. of sodium methoxide. The mixture is stirred at room temperature for 3 hours, after which time the inorganic matter is filtered off. The filtrate is concentrated under reduced pressure and the residue is recrystallized from benzene-n-hexane. The procedure provides 1.98 g. of 6-benzyloxy-1,2-epoxy-5-methoxycarbonyl-1,2,3,4-tetrahydronaphthalene as colorless plates melting at 135°–136° C.

Elemental analysis; for $C_{19}H_{18}O_4$; Calculated C, 73.53; H, 5.85; Found C, 73.47; H, 5.89.

REFERENCE EXAMPLE 60

In a mixture of 20 ml. methanol and 10 ml. tert-butylamine is dissolved 1.67 g. of 6-benzyloxy-1,2-epoxy-5-methoxycarbonyl-1,2,3,4-tetrahydronaphthalene, and the mixture is heated in a sealed tube at 100° C for 12 hours. The reaction mixture is concentrated under reduced pressure and the residue is dissolved in benzene, followed by the addition of ethanolic hydrochloric acid. The resulting precipitate is recovered by filtration and recrystallized from methanol-ether. The procedure yields 1.3 g. of 6-benzyloxy-1-tert-butylamino-2-hydroxy-5-methoxycarbonyl-1,2,3,4-tetrahydronaphthalene hydrochloride as colorless prisms melting at 235°14 236° C(decomp.).

Elemental analysis; for $C_{23}H_{29}O_4N \cdot HCl$; Calculated C, 65.78; H, 7.20; N, 3.34; Found C, 65.52; H, 7.21; N, 3.39.

REFERENCE EXAMPLE 61

In 70 ml. of anhydrous benzene is dissolved 1.0 g. of 6-benzyloxy-1-tert-butylamino-2-hydroxy-5-methoxycarbonyl-1,2,3,4-tetrahydronaphthalene and, with the addition of 600 mg. of anyhydrous sulfuric acid-triethylamine, the solution is heated at 80° C. for 2 hours. Then, 2.0 g. of anhydrous potassium carbonate is added and the mixture is stirred at 80° C for 2 hours, after which time the inorganic matter is filtered off. The filtrate is concentrated under reduced pressure and the residue is recrystallized from ethyl etherpetroleum ether. The procedure provides 890 mg. of 6-benzyloxy-1,2-tert-butylimino-5-methoxycarbonyl-1,2,3,4-tetrahydronaphthalene as colorless needles melting at 78°–80° C.

Elemental analysis; for $C_{23}H_{27}O_3N$; Calculated C, 75.59; H, 7.45; N, 3.83; Found C, 75.31; H, 7.59; N, 3.58.

REFERENCE EXAMPLE 62

In a mixture of 30ml. dioxane, 10 ml. water and 250 mg. glacial acetic acid is dissolved 1.0 g. of 6-benzyloxy-1,2-tert-butylimino-5-methoxycarbonyl-1,2,3,4-tetrahydronaphthalene, and the solution is agitated at 80° C for 3 hours. The reaction mixture is concentrated under reduced pressure and the residue is dissolved in ethyl acetate, followed by the addition of alcoholic hydrochloric acid. The procedure yields trans-6-benzyloxy-2-tert-butylamino-1-hydroxy-5-methoxycarbonyl-1,2,3,4-tetrahydronaphthalene hydrochloride. Melting point: 240°–242° C(decomp.)

REFERENCE EXAMPLE 63

By procedures similar to those of Reference Example 57 to 61, 6-benzyloxy-5-cyano-3,4-dihydro-1(2H)-naphthalenone is converted to 6-benzyloxy-1,2-tert-butylimino-5-cyano-1,2,3,4-tetrahydronaphthalene. Melting point: 114°–114.5° C.

Elemental analysis; for $C_{22}H_{24}ON_2$; Calculated C, 79.48; H, 7.28; N, 8.43; Found C, 79.63; H, 6.90; N, 8.27.

The above-mentioned compound is hydrolyzed in a manner similar to that of Reference Example 62 to obtain trans-6-benzyloxy-2-tert-butylamino-5-cyano-1-hydroxy-1,2,3,4-tetrahydronaphthalene. Melting point: 120°–122° C.

REFERENCE EXAMPLE 64

By procedures similar to those of Reference Examples 57 to 62, 6-benzyloxy-5-nitro-3,4-dihydro-1(2H)-naphthalenone is converted to trans-6-benzyloxy-2-tert-butylamino-1-hydroxy-5-nitro-1,2,3,4-tetrahydronaphthalene hydrochloride. Melting point: 255°–257° C(decomp.).

REFERENCE EXAMPLE 65

Under stirring, 10 g. of lithium cyanoborohydride is added a mixed solution of 20 g. 5-amino-6-benzyloxy-3,4-dihydro-1(2H)-napthalenone hydrochloride and 20 g. benzaldehyde in 200 ml. methanol. After 2 hours, the reaction mixture is added to water and the resulting oily precipitate is extracted into benzene. The benzene layer is washed with sodium hydrogen sulfite and with water, dried and concentrated under reduced pressure. The procedure provides 20 g. of 5-benzylamino-6-benzyloxy-3,4-dihydro-1(2H)-naphthalenone. NMR(CDCl$_3$) γ : 4.08(1H,s), 4.60(2H,s), 5.00(1H,s), 7.20–7.50(10H,m)

REFERENCE EXAMPLE 66

To a methanolic solution of 20 g. 5-benzylamino-6-benzyloxy-3,4-dihydro-1(2H)-napthalenone is added 5.0 g. of sodium borohydride and the mixture is stirred at room temperature for 30 minutes. To the reaction mixture is added water and the resulting oily precipitate is extracted with chloroform. The extract is washed with water, dried and concentrated under reduced pressure. The residue is recrystallized from a solvent mixture of ethyl ether and petroleum ether. The procedure provides 13 g. of 5-benzylamino-6-benzyloxy-1-hydroxy-1,2,3,4-tetrahydronaphthalene as colorless needles melting at 88°–90° C.

REFERENCE EXAMPLE 67

A mixture of 10 g. 5-benzylamino-6-benzyloxy-1-hydroxy-1,2,3,4-tetrahydronaphthalene, 100ml. formic acid and 100 ml. formalin is refluxed for 5 hours, after which time it is concentrated under reduced pressure. The residue is dissolved in water and rendered alkaline with aqueous ammonia. The resulting oily precipitate is extracted with ethyl acetate, washed with water, dried and concentrated under reduced pressure. The procedure provides 6.0 g. of 8-(N-benzyl-N-methylamino)-7-benzyloxy-1,2-dihydronaphthalene as a colorless oil.

REFERENCE EXAMPLE 68

In a manner similar to that of Reference Example 58, 19 g. of 8-(N-benzyl-N-methylamino)-7-benzyloxy-1,2-dihydronaphthalene is converted to 23 g. of 5-(N-benzyl-N-methylamino)-6-benzyloxy-2-bromo-1-hydroxy-1,2,3,4-tetrahydronaphthalene.

NMR(CDCl$_3$) spectrum $\delta$ : 2.60(3H,s), 4.21(2H,s), 4.82(1H, d,J=8Hz), 5.18(2H,s)

REFERENCE EXAMPLE 69

By procedures to those of Reference Examples 59 and 60, 11.0 g. of 5-(N-benzyl-N-methylamino)-6-benzyloxy-2-bromo-1-hydroxy-1,2,3,4-tetrahydronaphthalene is converted to 5.5 g. of 5-(N-benzyl-N-methylamino)-6-benzyloxy-1-t-butylamino-2-hydroxy-1,2,3,4-tetrahydronaphthalene oxalate as colorless needles melting at 186°–188° C.

Elemental analysis; for $C_{28}H_{34}O_2N_2 \cdot C_2H_2O_4$; Calculated C, 69.21; H, 6.97; N, 5.38; Found C, 69.33; H, 6.95; N, 5.08.

REFERENCE EXAMPLE 70

In a sealed tube, 12 g. of 5-(N-benzyl-N-methylamino)-6-benzyloxy-2-bromo-1-hydroxy-1,2,3,4-tetrahydronaphthalene is reacted with 36 ml. of isopropylamine at 100°110° C for 2 hours. The reaction mixture is concentrated under reduced pressure and the residue is diluted with water and extracted with ethyl acetate. The extract is washed with water, dried and concentrated under reduced pressure. The residue is purified by column chromatography on silica gel (developer solvent system: acetone-benzene=1:4) to obtain an oil. This oil is dissolved in 20 ml. of methanol and, following the addition of an ethereal solution of oxalic acid, the mixture is allowed to stand at room temperature. The procedure provides 7.2 g. of 5-(N-benzyl-N-methylamino)-6-benzyloxy-2-hydroxy-1-isopropylamino-1,2,3,4-tetrahydronaphthalene oxalate as colorless needless melting at 156°–157° C.

Elemental analysis; for $C_{27}H_{32}O_2N_2 \cdot C_2H_2O_4$; Calculated C, 68.75; H, 6.77; N, 5.53; Found C, 68.44; H, 6.89; N, 5.60.

REFERENCE EXAMPLE 71

In water is dissolved 7.0 g. of 5-(N-benzyl-N-methylamino)-6-benzyloxy-2-hydroxy-1-isopropylamino-1,2,3,4-tetrahydronaphthalene oxalate and the solution is rendered alkaline with sodium hydrogen carbonate and extracted with 200 ml. of benzene. The extract is washed with water and dried. Following the addition of 7.0 g. of an adduct of sulfuric anhydride to triethylamine, the solution is refluxed under stirring for 3 hours. Then, with the addition of 14 g. potassium carbonate and 14 g. sodium methoxide, it is further refluxed for 28 hours.

To the reaction mixture is added water and the organic layer is taken, washed with water, dried and concentrated under reduced pressure. The residue is dissolved in a solvent mixture of 80 ml. dioxane and 20 ml. water, followed by the addition of 1 ml. acetic acid. The mixture is further refluxed for 10 hours.

The reaction mixture is diluted with 500 ml. of water and extracted with chloroform. The chloroform layer is washed with water, dried and concentrated under reduced pressure. The residue is purified by column chromatography on silica gel (developer solvent system: acetone-benzene=1:4) to obtain an oil. The oil is dissolved in 5 ml. of methanol. To the solution is added an ethereal solution of oxalic acid and the mixture is allowed to stand at room temperature. The procedure provides 0.7 g. of 5-(N-benzyl-N-methylamino)-5-benzyloxy-1-hydroxy-2-isopropylamino-1,2,3,4-tetrahydronaphthalene oxalate as colorless needles melting at 168° –172° C.

Elemental analysis; for $C_{27}H_{32}O_2N_2 \cdot C_2H_2O_4$; Calculated C, 68,75; H, 6.77; N, 5.23; Found C, 68.44; H, 6.96; N, 5.20.

NMR(DMSO-d$_6$) $\delta$ : 4.76–4.55(1H,m)

REFERENCE EXAMPLE 72

In a manner similar to that of Reference Example 71, 5.5 g. of 5-(N-benzyl-N-methylamino)-6-benzyloxy-1-t-butylamino-2-hydroxy-1,2,3,4-tetrahydronaphthalene oxalate is treated to obtain 0.2 g. of cis-5-(N-benzyl-N-methylamino)-6-benzyloxy-2-t-butylamino-1-hydroxy-1,2,3,4-tetrahydronaphthalene oxalate as colorless needles melting at 179° –180° C, and 1.0 g. of trans-5-(N-benzyl-N-methylamino)-6-benzyloxy-1-hydroxy-2-t-butylamino-1,2,3,4-tetrahydronaphthalene oxalate as colorless needles melting at 189°–190° C.

REFERENCE EXAMPLE 73

In 2.5 l. of glacial acetic acid is dissolved 417 g. of methyl 2-hydroxy-1-naphthoate, and with the addition of 150 g. of 5% palladium-on-carbon, reduction is carried out at a temperature of 60° to 80° C with hydrogen introduced at a pressure of 100kg./cm$^2$. In 3 hours, approximately 2 moles of hydrogen is absorbed. The reaction mixture is filtered and the filtrate is concentrated under reduced pressure. The residue is then subjected to distillation under reduced pressure and the fraction boiling at 123°–125° C (0.6 mmHg) is recovered to obtain methyl 2-hydroxy-5,6,7,8-tetrahydro-1-naphthoate as a colorless oil. The oil solidifies on standing in the cold.

REFERENCE EXAMPLE 74

In a manner similar to that of Reference Example 3, 117 g. of 2-hydroxy-5,6,7,8-tetrahydro-1-naphthoate is treated to obtain methyl 2-benzyloxy-5,6,7,8-tetrahydro-1-naphthoate as colorless prisms melting at 59°–61° C. Yield 122 g.

Elemental analysis; for $C_{19}H_{20}O_3$; Calculated C, 77.00; H, 6.80; Found C, 77.06; H, 6.75.

REFERENCE EXAMPLE 75

In 250 ml. of glacial acetic acid is dissolved 60 g. of methyl 2-benzyloxy-5,6,7,8-tetrahydro-1-naphthoate and while the solution is cooled to 10°–15° C with icewater, a solution of 45 g. chromic anhydride (CrO$_3$) in a mixture of 30 ml. water and 100 ml. glacial acetic acid is added dropwise under constant agitation.

The mixture is agitated at 10°–15° C for 3 hours, after which time the excess oxidizing agent is decomposed by addition of 20 ml. of methanol. The solvent is then distilled off under reduced pressure and 2 l. of acetone is added to the residue. The insolubles are filtered off and the filtrate is concentrated under reduced pressure. The residue is dissolved in 1 l. of ethyl acetate, followed by washing with water, 10% aqueous sodium hydrogen carbonate solution and water in the order mentioned. The solution is dried over anhydrous sodium sulfate and concentrated under reduced pressure. Finally, the residue is recrystallized from n-hexane-ether to recover 6-benzyloxy-5-methoxycarbonyl-3,4-dihydro-1(2H)-naphthalenone as colorless prisms melting at 55°–56° C. Yield 55 g.

Elemental analysis; for $C_{19}H_{18}O_4$; Calculated C, 73.53; H, 5.85; Found C, 73.98; H, 5.91.

REFERENCE EXAMPLE 76

In 20 ml. of acetic anhydride is dissolved 5.2 g. of methyl 2-hydroxy-5,6,7,8-tetrahydro-1-naphthoate, followed by the addition of 5 ml. of anhydrous pyridine. The mixture is agitated at room temperature overnight.

The reaction mixture is poured in ice-water, followed by stirring for a while. The resulting colorless crystals are recovered by filtration, rinsed with water and dissolved in ethyl acetate. The solution is washed with dilute hydrochloric acid and with water. The solvent is then distilled off under reduced pressure, followed by recrystallization from methanol. The procedure yields 6 g. of methyl 2-acetoxy-5,6,7,8-tetrahydro-1-naphthoate as colorless prisms melting at 93°–96° C.

Elemental analysis; for $C_{14}H_{16}O_4$; Calculated C, 67.73; H, 6.50; Found C, 67.51; H, 6.48.

NMR(CLCl$_3$) δ : 2.24(3H,s), 3.88(3H,s), 6.85(1H,d,J=7.2Hz), 7.15(1H,d,J=7.2Hz)

REFERENCE EXAMPLE 77

In 5 ml. of acetic acid is dissolved 1.0 g. of methyl 2-acetoxy-5,6,7,8-tetrahydro-1-naphthoate and, under agitation at 10°–15° C, a solution of 886 mg. chromic anhydride in a mixture of 0.75 ml. water and 2 ml. acetic acid is added dropwise. After the dropwise addition has been completed, the reaction mixture is further agitated at the temperature indicated above for 3 hours. Then, at room temperature, the mixture is agitated overnight. To this reaction mixture is added 1 ml. of methanol and, after the solvent is distilled off under reduced pressure, 100 ml. of acetone is added to the residue. The insolubles are filtered off and the filtrate is concentrated under reduced pressure. The concentration residue is dissolved in ethyl acetate, followed by washing with water, 10% aqueous sodium hydrogen carbonate solution and water in the order mentioned. After drying, the solvent is distilled off and the residue is dissolved in a mixture of methanol and ethyl ether, followed by the addition of n-hexane. The procedure yields 59 mg. of 6-acetoxy-5-methoxycarbonyl-3,4-dihydro-1(2H)-naphthalenone as colorless powders melting at 149.5°–153.5° C.

Elemental analysis; for $C_{14}H_{14}O_5$; Calculated C, 64.12; H, 5.38; Found C, 63.93; H, 5.26.

NMR(CDCl$_3$) δ : 2.20(3H,s), 3.90(3H,s), 7.30(2H,s)

REFERENCE EXAMPLE 78

In 20 ml. of dimethylformamide is dissolved 5.0 g. of methyl 2-hydroxy-5,6,7,8-tetrahydro-1-naphthoate, followed by addition of 2.9 g. of potassium carbonate. Under agitation, 25 g. of methyl iodide is added dropwise, and the mixture is heated on reflux for about 1 hour. After cooling, the reaction mixture is poured in ice-water and extracted with ethyl acetate. The ethyl acetate layer is washed with water and dried. Finally, the solvent is distilled off under reduced pressure to recover about 6 g. of methyl 2-methoxy-5,6,7,8-tetrahydro-1-naphthoate as a brown-colored oil.

NMR(CDCl$_3$) δ : 3.78(3H,s), 3.88(3H,s), 6.67(1H,d,J=8.4Hz), 7.03(1H,d,J=8.4Hz).

IR ν liq. max (cm$^{-1}$): 1730.

REFERENCE EXAMPLE 79

One gram of methyl 2-methoxy-5,6,7,8-tetrahydro-1-naphthoate is treated in the same manner as Reference Example 77 and the resulting crude crystals are recrystallized from methanol. The procedure yields 480 mg. of 6-methoxy-5-methoxycarbonyl-3,4-dihydro-1(2H)-naphthalenone as pale yellowish needles melting at 141°–145° C.

Elemental analysis; for $C_{13}H_{14}O_4$; Calculated C, 66.66; H, 6.02; Found C, 66.56; H, 5.88.

NMR(CDCl$_3$) δ : 3.87(3H,s), 3.90(3H,s), 6.88(1H,d,J=9Hz), 8.10(1H,d,J=9Hz)

REFERENCE EXAMPLE 80

By the procedures similar to those of Reference Examples 20 and 21, 6-benzyloxy-5-methoxycarbonyl-3,4-dihydro-1(2H)-naphthalenone is converted to 2-amino-6-benzyloxy-5-methoxycarbonyl-3,4-dihydro-1(2H)-naphthalenone hydrochloride. Pale-yellow prisms melting at 205°–210° C (decomp.).

Elemental analysis; for $C_{19}H_{19}NO_4 \cdot HCl$; Calculated C, 63.07; H, 5.57; N, 3.87; Found C, 62.77; H, 5.63; N, 3.79.

REFERENCE EXAMPLE 81

In 20 ml. of anhydrous tetrahydrofuran is dissolved 535 mg. of trans-6-benzyloxy-2-cyclobutylamino-1-hydroxy-5-methoxycarbonyl-1,2,3,4-tetrahydronaphthalene and with the addition of 200 mg. of lithium aluminum hydride, the solution is refluxed in a current of molecular nitrogen for 4 hours. After cooling, a 20% solution of sodium hydroxide is added, followed by extraction with ethyl acetate. The ethyl acetate layer is washed with water, dried and concentrated under reduced pressure. The residue is recrystallized from ethyl acetate. The procedure provides trans-6-benzyloxy-2-cyclobutylamino-1-hydroxy-5-hydroxymethyl-1,2,3,4-tetrahydronaphthalene as colorless platelets melting at 156°–158° C. Yield 377 mg.

NMR spectrum (DMSO-d$_6$) δ : 4.13(1H,d,J=7Hz)

Elemental analysis; for $C_{22}H_{27}NO_3$; Calculated C, 74.75; H, 7.70; N, 3.96; Found C, 74.46; H, 7.75; N, 3.82.

REFERENCE EXAMPLE 82

In manners similar to that of Reference Example 81, the 5-hydroxymethyl compounds listed in Table below are obtained from the corresponding 5-methoxycarbonyl compounds having the same configuration, respectively.

| Reference Ex. | R¹ | Configuration | Melting point °C | NMR spectrum, δ(solvent) |
|---|---|---|---|---|
| 82 | -cyclohexyl | trans | 145–147 | 4.13:1H,d, J=8Hz (DMSO-d₆) |
| 83 | -cyclopentyl | trans | 128–130 | 4.22:H,d =8Hz 4.57:2H,s (DMSO-d₆+D₂O) |
| 84 | -CH(CH₃)CH₂-C₆H₄-OCH₃ | trans | 119–125 (decomp.) | 4.58:1H,d, J=9Hz (CDCl₃) |
| 85 | -CH(CH₃)CH₂-C₆H₄-OH | trans | 175–179 | 4.61:2H,s 4.78:1H,d J=9Hz 5.09:2H,s (DMSO-d₆+D₂O) |
| 86 | -CH(CH₃)₂ | cis | 131–133 | 4.46-1H,d, J=3Hz 4.58:2H,s (DMSO-d₆) |
| 87 | -C(CH₃)₃ | cis | 120–122 | 4.32:1H,d J=4Hz (DMSO-d₆) |
| 88 | -CH(CH₃)₂ | trans | 142 | — |
| 89 | -C(CH₃)₃ | trans | 143–144 | — |
| 90 | -C₂H₅ | | 158–159 | — |
| 91 | -H | | 148–150 | — |

REFERENCE EXAMPLE 92 a. To a solution of 7.6 g. of 5-amino-6-benzyloxy-3,4-dihydro-1(2H)-naphthalenone in 200 ml. of chloroform is added 10 g. of anhydrous trifluoroacetic acid. The mixture is stirred at room temperature for 2 hours and, then, concentrated under reduced pressure. The residue is recrystallized from methanol. The procedure provides 8.0 g. of 6-benzyloxy-5-trifluoroacetylamino-3,4-dihydro-1(2H)-naphthalenone as colorless needles melting at 190°–191° C.

Elemental analysis; for $C_{19}H_{16}O_3NF_3$; Calculated C, 62.81; H, 4.44; N, 3.86; Found C, 62.66; H, 4.20; N, 3.71.

b. To a solution of 9.7 g. of the trifluoroacetyl compound according to a) in 40 ml. acetone is added 6.4 g. of potassium hydroxide and, under stirring and reflux, 16 g. of methyl iodide is added dropwise. The mixture is further refluxed for 30 minutes, after which time it is concentrated under reduced pressure. To the residue are added 50 ml. of ethanol and a solution of 14 g. potassium hydroxide in 50 ml. water, followed by refluxing for 2 hours. After cooling, the reaction mixture is diluted with 500 ml. of water and extracted with chloroform. The chloroform layer is washed with water, dried and concentrated under reduced pressure. To the residue are added 20 ml. of alcoholic hydrochloric acid and 100 ml. of ethyl ether and the mixture is allowed to stand at room temperature. The procedure provides 7.2 g. of 6-benzyloxy-5-methylamino-3,4-dihydro-1(2H)-naphthalenone hydrochloride as pale-yellow needles melting at 193°–195° C.

Elemental analysis; for $C_{18}H_{19}O_2N \cdot HCl \cdot \frac{1}{2}H_2O$; Calculated C, 66.15; H, 6.17; N, 4.29; Found C, 66.31; H, 6.17; N, 4.12.

c. To a solution of 20 g. of the methylamino-compound hydrochloride according to (b) in 200 ml. of chloroform are added 50 ml. of water and 20 g. of potassium carbonate and, under vigorous stirring, 13 g. of benzyloxycarbonyl chloride is added dropwise. The reaction is carried out at room temperature for 3 hours. Following the addition of 200 ml. water, the chloroform layer is taken, dried and concentrated under reduced pressure.

The procedure provides 30 g. of 5-(N-benzyloxycarbonyl-N-methylamino)-6-benzyloxy-3,4-dihydro-1(2H)-naphthalenone as an oil.

Infrared absorption spectrum: 1700, 1670 cm⁻¹

NMR spectrum (CDCl$_3$) δ : 3.16(3H,s), 5.05(4H,s), 6.80–7.40(12H,m).

d. The benzyloxycarbonyl-compound according to c) is reacted in a manner similar to that described in Reference Example 20 to obtain 30 g. of 5-(N-benzyloxycarbonyl-N-methylamino)-6-benzyloxy-3,4-dihydro-1(2H)-naphthalenone oxime as an oil.

Infrared absorption spectrum: 3350, 1680 cm$^{-1}$ e. The oxime according to (d) is reacted with p-toluenesulfonyl chloride in a manner similar to that described in Reference Example 8 to obtain 5-(N-benzyloxycarbonyl-N-methylamino)-6-benzyloxy-1-(p-toluenesulfonyloxyimino)-1,2,3,4-tetrahydronaphtalene as colorless prisms melting at 158°–160° C.

Elemental analysis; for C$_{33}$H$_{32}$O$_8$N$_2$S; Calculated C, 67.80; H, 5.52; N, 4.79; Found C, 67.60; H, 5.59; N, 4.68.

REFERENCE EXAMPLE 93

In a manner similar to that of Reference Example 28, 6-benzyloxy-5-methylamino-3,4-dihydro-1(2H)-naphthalenone is treated to obtain 6-benzyloxy-5-(N-benzyl-N-methylamino)-3,4-dihydro-1(2H)-naphthalenone hydrochloride. Melting point: 157°–159° C.

REFERENCE EXAMPLE 94

By procedures similar to those of Reference Examples 20 and 21, 2-amino-6-benzyloxy-5-(N-benzyl-N-methylamino)-3,4-dihydro-1(2H)-naphthalenone hydrochloride is obtained from 6-benzyloxy-5-(N-benzyl-N-methylamino)-3,4-dihydro-1(2H)-naphthalenone hydrochloride. Melting point: 215°–219° C.

REFERENCE EXAMPLE 95

By procedures similar to those of Reference Examples 20 and 21, 2-amino-6-benzyloxy-5-methanesulfonylmethyl-3,4-dihydro-1(2H)-naphthalenone hydrochloride is obtained from 6-benzyloxy-5-methanesulfonylmethyl-3,4-dihydro-1(2H)-naphthalenone. Melting point: 250° C or up.

REFERENCE EXAMPLE 96

By procedures similar to those of Reference Examples 20 and 21, 2-amino-6-benzyloxy-5-(N-benzoyl-N-methylamino)-3,4-dihydro-1(2H)-naphthalenone hydrochloride is obtained from 6-benzyloxy-5-(N-benzoyl-N-methylamino)-3,4-dihydro-1(2H)-naphthalenone. Melting point: 220°–223° C.

REFERENCE EXAMPLE 97

By procedures similar to those of Reference Example 60 and 61, 6-benzyloxy-1,2-epoxy-5-methoxycarbonyl-1,2,3,4-tetrahydronaphthalene is converted to 6-benzyloxy-5-methoxy-carbonyl-1,2-isopropylimino-1,2,3,4-tetrahydronaphthalene. Melting point: 103° C.

REFERENCE EXAMPLE 98

In a manner similar to that of Reference Example 62, 6-benzyloxy-5-methoxycarbonyl-1,2-isopropylimino-1,2,3,4-tetrahydronaphthalene is hydrolyzed to obtain cis-6-benzyloxy-1-hydroxy-5-methoxycarbonyl-2-isopropylamino-1,2,3,4-tetrahydronaphthalene. Melting point: 113°–114° C.

REFERENCE EXAMPLE 99

In a manner similar to that of Reference Example 62, 6-benzyloxy-1,2-tert-butylimino-5-cyano-1,2,3,4-tetrahydronaphthalene is hydrolyzed to obtain cis-6-benzyloxy-2-tert-butylamino-5-cyano-1-hydroxy-1,2,3,4-tetrahydronaphthalene. Melting point: 165°–166° C.

REFERENCE EXAMPLE 100

In a manner similar to that of Reference Example 62, 6-benzyloxy-1,2-tert-butylimino-5-methoxycarbonyl-1,2,3,4-tetrahydronaphthalene is hydrolyzed with concentrated sulfuric acid to obtain cis-6-benzyloxy-2-tert-butylamino-1-hydroxy-5-methoxycarbonyl-1,2,3,4-tetrahydronaphthalene. Melting point: 104°–105° C.

REFERENCE EXAMPLE 101

In a manner similar to that of Reference Example 54, trans-5-aminomethyl-6-benzyloxy-2-tert-butylamino-1-hydroxy-1,2,3,4-tetrahydronaphthalene is obtained from trans-6-benzyloxy-2-tert-butylamino-5-cyano-1-hydroxy-1,2,3,4-tetrahydronaphthalene. Melting point: 170°–171° C.

REFERENCE EXAMPLE 102

To a solution of 1.0 g. of trans-2-amino-6-benzyloxy-1-hydroxy-5-methoxycarbonyl-1,2,3,4-tetrahydronaphthalene in 15 ml. of pyridine is added 3 ml. of anhydrous acetic acid and the mixture is stirred at room temperature for 15 hours. The reaction mixture is poured into ice water and the resulting precipitates are recovered by filtration, washed with water, dried and recrystallized from ethyl acetate-isopropyl ether to obtain trans-1-acetoxy-2-acetylamino-6-benzyloxy-5-methoxycarbonyl-1,2,3,4-tetrahydronaphthalene as colorless needles melting at 171°–172° C.

REFERENCE EXAMPLE 103

To a solution of 1.0 g. of trans-2-amino-6-benzyloxy-1-hydroxy-5-methoxycarbonyl-1,2,3,4-tetrahydronaphthalene in 20 ml. of ethyl acetate are added 5 ml. of water and 400 mg. of ethyl chlorcarbonate, and with stirring at room temperature, 1.0 g. of anhydrous potassium carbonate is added in small portions. After one-hour stirring, the organic layer is recovered, washed with water, dried and concentrated under reduced pressure. The residue is recrystallized from ethyl acetate-n-hexane to obtain trans-6-benzyloxy-2-ethoxycarbonylamino-1-hydroxy-5-methoxycarbonyl-1,2,3,4-tetrahydronaphthalene as colorless needles melting at 147°–148° C.

REFERENCE EXAMPLE 104

To a solution of 3.65 g. of 6-benzyloxy-1,2-tert-butylimino-5-methoxycarbonyl-1,2,3,4-tetrahydronaphthalene in 100 ml. of anhydrous dioxane is added dropwise, under cooling with ice, a solution of 1.0 g. of concentrated sulfuric acid dissolved in 50 ml. of anhydrous dioxane. The mixture is stirred for 2 hours, and the resulting precipitates are recovered by filtration, rinsed with ethyl ether and dried to obtain 3.4 g. of trans-6-benzyloxy-2-tert-butylamino-1-hydroxy-5-methoxycarbonyl-1,2,3,4-tetrahydronaphthalene O-sulfonate as a white powder. Melting point: 232°–234° C(decomp.).

NMR spectrum (DMSO-d$_6$) δ : 5.30(1H,d,J=10Hz, C$_1$-H)

REFERENCE EXAMPLE 105

In a manner similar to that of Reference Example 104, trans-6-benzyloxy-2-isopropylamino-1-hydroxy-5-methoxycarbonyl-1,2,3,4-tetrahydronaphthalene O-sulfonate is obtained from 6-benzyloxy-1,2-isopropylimino-5-methoxycarbonyl-1,2,3,4-tetrahydronaphthalene. White powder: Melting point: 210°–213° C(decomp.).

NMR spectrum (DMSO-$d_6$) δ : 5.32(1H,d,J=9Hz,$C_1$-H)

REFERENCE EXAMPLE 106

To a solution of 1.21 g. of 6-benzyloxy-1,2-isopropylimino-5-methoxycarbonyl-1,2,3,4-tetrahydronaphthalene in 100 ml. of anhydrous dioxane is added 20 ml. of glacial acetic acid, and the mixture is heated at 60° C for 30 minutes. The reaction mixture is concentrated under reduced pressure and the residue is recrystallized from ethyl ether-n-hexane to obtain 1.39 g. of trans-1-acetoxy-6-benzyloxy-2-isopropylamino-5-methoxycarbonyl-1,2,3,4-tetrahydronaphthalene acetate as colorless crystals melting at 106°–109° C.

NMR spectrum ($CDCl_3$) δ : 5.85(1H,d,J=5Hz, $C_1$-H)

REFERENCE EXAMPLE 107

To a suspension of 1.5 g. of trans-6-benzyloxy-5-(N-benzyloxycarbonyl-N-methylamino)-1-hydroxy-2-isopropylamino-1,2,3,4-tetrahydronaphthalene hydrochloride in 50 ml. of tetrahydrofuran is added, with stirring, 1.0 g. of lithium aluminum hydride, and the mixture is refluxed with stirring for 1.5 hours. After cooling, the reaction mixture is admixed with water to decompose the excess reagent and rendered alkaline with sodium hydrogen carbonate. The insolubles are filtered off and the filtrate is dried, concentrated under reduced pressure. The residue is dissolved in 10 ml. of alcoholic hydrochloric acid, and, after the addition of ethyl ether, the solution is allowed to stand at room temperature to obtain 0.7 g. of trans-6-benzyloxy-1-hydroxy-2-isopropylamino-5-dimethylamino-1,2,3,4-tetrahydronaphthalene hydrochloride. Melting point: 220°–222° C(decomp.).

REFERENCE EXAMPLE 108

10 ml. of anhydrous acetic acid is added dropwise to a solution of 2.0 g. of trans-2-amino-6-benzyloxy-5-(N-benzyl-N-methylanino)-1-hydroxy-1,2,3,4-tetrahydronaphthalene oxalate in 50 ml. of methanol under cooling with ice, and the mixture is stirred at room temperature for 2 hours. The reaction mixture is poured into water and rendered alkaline with sodium hydrogen carbonate. The resulting precipitates are extracted, washed with water and concentrated under reduced pressure. The resulting crude crystals are recrystallized from ethyl ether to yield 2.0 g. of trans-2-acetylamino-6-benzyloxy-5-(N-benzyl-N-methylamino)-1-hydroxy-1,2,3,4-tetrahydronaphthalene. Melting point: 125°–127° C.

Elemental analysis; for $C_{27}H_{30}O_3N_2$; Calculated C, 75.32; H, 7.02; N, 6.51; Found C, 75.41; H, 7.05; N, 6.65.

REFERENCE EXAMPLE 109

Trans-2-amino-6-benzyloxy-5-(N-benzyl-N-methylamino)-1-hydroxy-1,2,3,4-tetrahydronaphthalene is treated in a manner similar to that of Reference Example 103 to obtain trans-2-ethoxycarbonylamino-6-benzyloxy-5-(N-benzyl-N-methylamino)-1-hydroxy-1,2,3,4-tetrahydronaphthalene. Melting point: 119°–120° C.

EXAMPLE 1

In 10 ml. of ethanol is suspended 100 mg. of sodium borohydride and, under stirring, is added 200 mg. of 6-benzyloxy-5-formyl-2-isopropylamino-3,4-dihydro-1(2H)-naphthalenone hydrochloride. The mixture is agitated at room temperature for 2 hours, after which time a saturated solution of sodium chloride and ethyl acetate was added. The ethyl acetate layer is taken, washed with a saturated aqueous solution or sodium chloride and dried over anhydrous sodium sulfate. The solvent is then distilled off under reduced pressure and the residue is recrystallized from ethyl acetate-ethanol. The above procedure provides trans-6-benzyloxy-1-hydroxy-5-hydroxymethyl-2-isopropylamino-1,2,3,4-tetrahydronaphthalene as white crystals. Yield 128 mg.; melting point: 138°–139° C.

Elemental analysis; for $C_{21}H_{27}O_3N\cdot\frac{1}{2}H_2O$; Calculated C, 71.98; H, 8.05; N, 4.00; Found C, 72.37; H, 8.06; N, 3.92.

EXAMPLE 2

In a manner similar to that of Example 1, 500 mg. of 2-amino-6-benzyloxy-5-formyl-3,4-dihydro-1(2H)-naphthalenone hydrochloride is reduced to obtain trans-2-amino-6-benzyloxy-1-hydroxy-5-hydroxymethyl-1,2,3,4-tetrahydronaphthalene as white crystals. Yield 260 mg.; melting point: 148°–150° C.

Elemental analysis; for $C_{18}H_{21}O_3N\cdot\frac{1}{2}H_2O$; Calculated C, 70.11; H, 7.19; N, 4.54; Found C, 70.51; H, 7.09; N, 4.79.

EXAMPLE 3

In 80 ml. of ethanol is dissolved 300 mg. of sodium borohydride and, under agitation at room temperature, 3.1 g. of 6-benzyloxy-5-cyano-2-isopropylamino-3,4-dihydro-1(2H)-naphthalenone hydrochloride is added in small portions. The mixture is agitated at room temperature for 2 hours, after which time it is concentrated to about 10 ml. under reduced pressure.

Following addition of a saturated aqueous solution of sodium chloride, the concentrate is extracted with ethyl acetate. The ethyl acetate layer is washed with a saturated aqueous solution of sodium chloride and dried. The solvent is distilled off under reduced pressure, and ethyl acetate is added to the residue. On standing, there is obtained trans-6-benzyloxy-5-cyano-1-hydroxy-2-isopropylamino-1,2,3,4-tetrahydronaphthalene as white crystals. Yield 2.8 g.; melting point: 141°–143° C. The hydrochloride of the above compound gives colorless prisms (from methanol) melting at 258°–260° C(decomp.).

Elemental analysis; for $C_{21}H_{24}O_2N_2\cdot HCl\cdot H_2O$; Calculated C, 64.52; H, 6.96; N, 7.17; Found C, 64.56; H, 6.50; N, 7.18.

EXAMPLE 4

In a manner similar to that of Example 3, 850 mg. of 2-amino-6-benzyloxy-5-cyano-3,4-dihydroxy-1(2H)-naphthalenone hydrochloride is reduced to obtain 700 mg. of trans-2-amino-6-benzyloxy-5-cyano-1-hydroxy-1,2,3,4-tetrahydronaphthalene hydrochloride. Colorless prisms melting at 272°–276° C(decomp.).

Elemental analysis; for $C_{18}H_{18}O_2N_2\cdot HCl$; Calculated C, 65.35; H, 5.79; N, 8.47; Found C, 65.24; H, 5.47; N, 8.32.

EXAMPLE 5

In a manner similar to that of Example 3, 200 mg. of 2-acetylamino-5-acetoxymethyl-6-benzyloxy-3,4-dihydro-1(2H)-naphthalenone is reduced to obtain trans-2-acetoxy-5-acetoxy-methyl-6-benzyloxy-1-hydroxy-1,2,3,4-tetrahydronaphthalene as colorless prisms. Yield 76 mg.; melting point: 190°–194° C.

Elemental analysis; for $C_{22}H_{25}NO_5$; Calculated C, 68.91; H, 6.57; N, 3.65; Found C, 68.75; H, 6.54; N, 3.68.

EXAMPLE 6

In a manner similar to that of Example 3, 1.4 g. of 2-amino-6-benzyloxy-5-methoxycarbonyl-3,4-dihydro-1(2H)-naphthalenone hydrochloride is reduced to obtain trans-2-amino-6-benzyloxy-1-hydroxy-5-methoxycarbonyl-1,2,3,4-tetrahydronaphthalene as colorless prisms melting at 124°–126° C.

Elemental analysis; for $C_{19}H_{21}NO_4$; Calculated C, 69.70; H, 6.47; N, 4.28;
Found C, 69.20; H, 6.59; N, 4.07.

EXAMPLE 7

In a manner similar to that of Example 3, 2-amino-3,2-benzyloxy-5-nitro-3,4-dihyro-1(2H)-naphthalenone hydrochloride is treated to obtain trans-2-amino-6-benzyloxy-5-nitro-1-hydroxy-1,2,3,4-tetrahydronaphthalene hydrochloride as colorless needles melting at 213°–215° C.

Elemental analysis; for $C_{17}H_{18}O_4N_2 \cdot HCl$; Calculated C, 58.20; H, 5.46; N, 7.99; Found C, 58.34; H, 5.59; N, 7.68.

EXAMPLE 8

In a manner similar to that of Example 3, 150 mg. of 6-hydroxy-5-hydroxymethyl-2-isopropylamino-3,4-dihydro-1(2H)-naphthalenone hydrochloride is reduced to obtain 63 mg. of trans-1,6-dihydroxy-5-hydroxymethyl-2-isopropylamino-1,2,3,4-tetrahydronaphthalene as white crystals melting at 182°–185° C (decomp.).

EXAMPLE 9

In a manner similar to that of Example 3, 85 mg. of trans-2-amino-5-ethoxymethyl-1-hydroxy-6-methoxy-1,2,3,4-tetrahydronaphthalene is obtained from 200 mg. of 2-amino-5-ethoxymethyl-6-methoxy-3,4-dihydro-1(2H)-naphthalenone hydrochloride. White crystals melting at 117°–118° C.

Elemental analysis; for $C_{14}H_{21}NO_3$; Calculated C, 66.90; H, 8.42; N, 5.57; Found C, 66.82; H, 8.58; N, 5.31.

EXAMPLE 10

0.3 g. of sodium borohydride is added to a solution of 0.6 g. 2-amino-6-benzyloxy-5-(N-benzyl-N-methanesulfonylamino)-3,4-dihydro-1(2H)-naphthalenone hydrochloride in 10 ml. of methanol and the mixture is agitated under cooling with ice for 30 minutes. The reaction mixture is poured in water and extracted with ethyl acetate. The extract is washed with water, dried and concentrated under reduced pressure. The residue is dissolved in alcoholic hydrochloric acid and the crystals formed on addition of ethyl ether are recovered by filtration. The procedure yields 0.5 g. of 2-amino-6-benzyloxy-5-(N-benzyl-N-methanesulfonylamino)-1-hydroxy-1,2,3,4-tetrahydronaphthalene hydrochloride as colorless needles melting at 205°–207° C.

Element analysis; for $C_{25}H_{28}O_4N_2S \cdot HCl$; Calculated C, 61.40; H, 5.98; N, 5.73; Found C, 61.76; H, 5.96; N, 5.72.

EXAMPLE 11

2-amino-6-benzyloxy-1-hydroxy-5-methanesulfonylmethyl-1,2,3,4-tetrahydronaphthalene acetate is obtained by reducing 2-amino-6-benzyloxy-5-methanesulfonylmethyl-3,4-dihydro-1(2H)-naphthalenone hydrochloride in a manner similar to that of Example 10 and converting the resultant to the acetate. Melting point: 110°–115° C(decomp.).

Mass spectrum (m/e): 361($M^+$)

EXAMPLE 12

2-amino-6-benzyloxy-5-(N-benzyl-N-methylamino)-1-hydroxy-1,2,3,4-tetrahydronaphthalene oxalate is obtained by reducing 2-amino-6-benzyloxy-5-(N-benzyl-N-methylamino)-3,4-dihydro-1(2H)-naphthalenone in a manner similar to that of Example 10 and converting the resultant to the oxalate. Melting point: 189°–191° C.

Elemental analysis; for $C_{25}H_{28}O_2N_2 \cdot C_2H_2O_4$; Calculated C, 67.76; H, 6.32; N, 5.85; Found C, 67.55; H, 6.01; N, 5.76.

EXAMPLE 13

To a solution of 7.0 g. of 2-amino-6-benzyloxy-5-nitro-3,4-dihydro-1-(2H)-naphthalenone hydrochloride in 70 ml. of methanol is added 1.3 g. of sodium borohydride and the mixture is agitated at room temperature for 30 minutes. The reaction mixture is poured in water, followed by extraction with ethyl acetate. The organic layer is washed with water, dried and concentrated under reduced pressure. The oily residue is dissolved in a small amount of alcoholic hydrochloric acid. The solution is treated with activated carbon and, then, ethyl ether is added. The resulting crystals are recovered by filtration. The procedure yields 6.0 g. of 2-amino-6-benzyloxy-5-nitro-1-hydroxy-1,2,3,4-tetrahydronaphthalene hydrochloride as colorless needles melting at 213°–215° C.

Elemental analysis; for $C_{17}H_{18}O_4N_2 \cdot HCl$; Calculated C, 58.20; H, 5,46; N, 7.99; Found C, 58.34; H, 5.59; N, 7.68.

EXAMPLE 14

In a manner similar to that of Example 13, 1.7 g. of 2-benzylamino-6-benzyloxy-1-hydroxy-5-nitro-1,2,3,4-tetrahydronaphthalene hydrochloride is obtained from 2.0 g. of 2-benzylamino-6-benzyloxy-5-nitro-3,4-dihydro-1-(2H)-naphthalenone. Colorless needles melting at 241°–246° C.

Elemental analysis; for $C_{24}H_{24}O_4N_2 \cdot HCl$; Calculated C, 65.37; H, 5.72; N, 6.35; Found C, 65.40; H, 5.52; N, 6.32.

EXAMPLE 15

In a manner similar to that of Example 13, 0.4 g. of 6-benzyloxy-1-hydroxy-2-isopropylamino-5-nitro-1,2,3,4-tetrahydronaphthalene hydrochloride is obtained from 0.6 g. of 6-benzyloxy-2-isopropylamino-5-nitro-3,4-dihydro-1(2H)-naphthalenone hydrochloride. Colorless needles melting at 268°–270° C.

Elemental analysis; for $C_{20}H_{24}O_4N_2 \cdot HCl$; Calculated C, 61.14; H, 6.41; N, 7.13; Found C, 61.44; H, 6.30; N, 7.21.

EXAMPLE 16

In a manner similar to Example 13, 0.7 g. of 2-amino-6-benzyloxy-5-chloro-3,4-dihydro-1(2H)-naphthalenone hydrochloride is reduced to obtain 0.5 g. of 2-amino-6-benzyloxy-5-chloro-1-hydroxy-1,2,3,4-tetrahydronaphthalene hydrochloride as colorless prisms melting at 277°–279° C.

Elemental analysis; for $C_{17}H_{18}O_2NCl \cdot HCl$; Calculated C, 60.01; H, 5.63; N, 4.12; Found C, 60.41; H, 5.14; N, 4.10.

EXAMPLE 17

In a mixture of 20 ml. ethanol and 2 ml. of triethylamine is dissolved 200 mg. of 6-hydroxy-5-hydroxymethyl-2-isopropylamino-3,4-dihydro-1(2H)-naphthalenone hydrochloride and, with the addition of 50 mg. of 5 % palladium-on-carbon, the solution is agitated in a current of hydrogen for 15 hours. The catalyst is filtered off and the filtrate is concentrated under reduced pressure. The resiude is dissolved in tetrahydrofuran. The insolubles are filtered off and the filtrate is concentrated under reduced pressure. The residue is recrystallized from ethanol-ethyl acetate. The procedure yields colorless crystals of 1,6-dihydroxy-5-hydroxymethyl-2-isopropylamino-1,2,3,4-tetrahydronaphthalene which is identical with the product according to the procedure of Example 71. Yield 108 mg.

EXAMPLE 18

A procedure similar to that of Example 17 is conducted using 6-hydroxy-5-(2-hyroxyethyl)-2-isopropylamino-3,4-dihydro-1(2H)-naphthalenone hydrochloride to obtain 0.1 g. of 1,6-dihydroxy-5-(2-hydroxyethyl)-2-isopropylamino-1,2,3, 4-tetrahydronaphthalene as colorless crystalline powders.

Elemental analysis; for $C_{15}H_{23}O_3N$; Calculated C, 67.89; H, 8.74; N, 5.28; Found C, 67.39; H, 8.68; N, 5.13.

EXAMPLES 19–22

The results set forth below in the table are obtained by procedures similar to the procedure described in Example 17.

| Ex. | Starting compound | Product compound | Melting point (°C) |
|---|---|---|---|
| 19 | [structure: BzO, NHCONH₂, tetralone with NHCH(CH₃)₂] | [structure: HO, NH₂, NHCONH₂, tetralol with NHCH(CH₃)₂, OH] | 198–200° (hydrochloride) |
| 20 | [structure: BzO, NO₂, tetralone with NHCHCH₂-indole, CH₃] | [structure: HO, NH₂, tetralol with NHCH-CH₂-indole, CH₃, OH] | 215–217° (hydrochloride) |
| 21 | [structure: BzO, NO₂, tetralone with NH-cyclohexyl] | [structure: HO, NH₂, tetralol with NH-cyclohexyl, OH] | 206–209° (hydrochloride) |
| 22 | [structure: BzO, NO₂, tetralone with NHCH₂CH₂OCH₃] | [structure: HO, NH₂, tetralol with NHCH₂CH₂OCH₃, OH] | 162–164° (fumarate) |

(Bz represents a benzyl group)

EXAMPLE 23

In 10 ml. of water is dissolved 0.5 g. of 2-amino-6-benzyloxy-5-(N-benzyl-N-methanesulfonylamino)-3,4-dihydro-1(2H)-naphthalene hydrochloride and, with the addition of 0.25 g. of platinum oxide, catalytic reduction is carried out at atmospheric temerature and pressure. After the stoichiometric amount of hydrogen has been absorbed, the catalyst is filtered off and the filtrate is concentrated under reduced pressure. The residue is dissolved in a small amount of ethanol, followed by the addition of ethyl ether. The resulting white needles are recovered by filtration. The procedure yields 0.15 g. of 2-amino-1,6-dihydroxy-5-methanesulfonylamino-1,2,3,4-tetrahydronaphthalene hydrochloride, melting point: 233°–235° C(decomp.).

Elemental analysis; for $C_{11}H_{16}O_4N_2S \cdot HCl \cdot H_2O$; Calculated C, 40.43; H, 5.86; N, 8.7; Found C, 40.87; H, 5.47; N, 8.48.

EXAMPLE 24

To a solution of 0.5 g. of 2-benzylamino-6-benzyloxy-5-nitro-3,4-dihydro-1(2H)-naphthalenone hydrochloride in 10 ml. of ethanol are added 1 ml. of alcoholic hydrochloric acid and 0.5 g. of platinum oxide, and catalytic reduction is carried out. After the hydrogen has ceased to be absorbed, the catalyst is filtered off and ethyl ether is added to the filtrate, whereupon colorless crystals separate out. The crystals are recovered by filtration, rinsed with ethyl ether and dried. The procedure yields 0.2 g. of 5-amino-2-cyclohexylmethylamino-1,6-dihyroxy-1,2,3,4-tetrahydronaphthalene hydrochloride as colorless needles melting at 230°–234° C (decomp.).

Elemental analysis; for $C_{17}H_{26}O_2N_2 \cdot HCl$; Calculated C, 56.20; H, 7.77; N, 7.71; Found C, 56.43; H, 7.49; N, 7.85.

EXAMPLE 25

To 10 ml. of an aqueous solution containing 0.5 g. of 2-amino-6-benzyloxy-5-nitro-3,4-dihydro-1(2H)-naphthalenone are added 0.5 ml. of concentrated hydrochloric acid and 0.25 g. of platinum oxide, and catalytic reduction is carried out. After the stoichiometric amount of hydrogen has been absorbed, the catalyst is filtered off and the filtrate is concentrated under reduced pressure. The residue is dissolved in a small amount of ethanol, followed by the addition of ethyl ether. The resulting crystals are recovered by filtration. The procedure yields 0.3 g. of 2,5-diamino-1,6-dihydroxy-1,2,3,4-tetrahydronaphthalene hydrochloride as colorless prisms. Melting point: higher than 300° C.

Elemental analysis; for $C_{10}H_{14}O_2N_2 \cdot 2HCl \cdot 3/2H_2O$; Calculated C, 40.82; H, 6.51; N, 9.52; Found C, 41.14; H, 6.52; N, 9.25.

EXAMPLE 26

In 10 ml. of methanol is dissolved 1 g. of 6-benzyloxy-2-oxyimino-5-methanesulfonylamino-3,4-dihydro-1(2H)-naphthalene and catalytic reduction is carried out in the presence of 0.1 g. of 5 % palladium-on-carbon as the catalyst until no more hydrogen is absorbed. The catalyst is filtered off and the filtrate is concentrated under reduced pressure. The residue is dissolved in a small amount of ethanolic hyrochloric acid, and ethyl ether is then added in small portions, whereupon colorless needles separate out. The procedure yields 0.5 g. of 2-amino-1,6-dihydroxy-5-methanesulfonylamino-1,2,3,4-tetrahydronaphthalene hydrochloride, melting point: 233°–235° C(decomp.). Mixture-melting of this product with the product according to Example 23 shows no melting point depression. The two products are also identical in infrared absorption spectrum.

EXAMPLE 27

In a manner similar to that of Example 26, 0.5 g. of 6-benzyloxy-5-methanesulfonylmethyl-2-oxyimino-3,4-dihydro-1(2H)-naphthalenone is reduced to obtain 0.2 g. of 2-amino-1,6-dihydroxy-5-methanesulfonylmethyl-1,2,3,4-tetrahydronaphthalene hydrochloride. Colorless amorphous powders.

Elemental analysis; for $C_{12}H_{17}O_4NS \cdot HCl$; Calculated C, 46.83; H, 5.89; N, 4.55; Found C, 46,58; H, 5.58; N, 4.34.

EXAMPLE 28

To a mixture of 10 ml. of ethanol and 20 and ml. acetone is dissolved 1 g. of 6-benzyloxy-2-oxyimino-5-methanesulfonylamino-3,4-dihydro-1(2H)-naphthalenone, and with the addition of 0.2 g. of triethylamine and 0.5 g of 5 % palladium-on-carbon, catalytic reduction is carried out in hydrogen streams. The catalyst is filtered off and ethanolic hydrochloric acid is added to the filtrate. The mixture is concentrated to dryness under reduced pressure and the concentrate is washed with a small amount of chloroform and recrystallized from ethanol-ethyl ether. The procedure yields 0.2 g. of 1,6-dihydroxy-2-isopropylamino-5-methanesulfonylamino-1,2,3,4-tetrahydronaphthalene hydrochloride. Melting point: 210°–213° C.

EXAMPLE 29

To 150 ml. of benzene is added 2.5 g. of 6-benzyloxy-2,5-dinitro-3,4-dihydro-1(2H)-naphthalenone, followed by dropwise addition of 26 g. of a 70 % benzene solution of sodium bis(2-methoxyethoxy)aluminum hydride. The mixture is refluxed for 6 hours and, following the addition of 70 ml. water, the mixture is filtered. The filtrate is concentrated to dryness under reduced pressure and the residue is dissolved in 100 ml. of methanol. With the addition of 1 g. of 5 % palladium-on-carbon, the solution is catalytically reduced in a current of hydrogen. The catalyst is filtered off and the filtrate is concentrated to dryness under reduced pressure. The residue is dissolved in a small amount of ethanolic hydrochloric acid, followed by the addition of ethyl ether. The procedure yields 0.8 g. of 2,5-diamino-1,6-dihydroxy-1,2,3,4-tetrahydronaphthalene hydrochloride as colorless crystals melting above 300° C.

EXAMPLE 30

In 20 ml. of 2N hydrochloric acid is dissolved 200 mg. of 6-hydroxy-5-hydroxymethyl-2-isopropylamino-3,4-dihydro-1(2H)-naphthalenone hydrochloride and with the addition of 100 mg. of 5 % palladium-on-carbon, the solution is agitated in hydrogen streams for 4 hours. After the hydrogen has ceased to be absorbed, the catalyst is filtered off and the filtrate is concentrated under reduced pressure and at a temperature not exceeding 40° C. The residue is then recrystallized from ethanol-ether. The procedure yields 1,6-dihydroxy-2-isopropylamino-5-methyl-1,2,3,4-tetrahydronaphthalene hydrochloride as colorless powders. Yield 152 mg.

Elemental analysis; for $C_{14}H_{21}NO_2 \cdot HCl \cdot H_2O$; Calculated C, 58.02; H, 8.35; N, 4.83; Found C, 57.72; H, 8.09; N, 4.61.

EXAMPLE 31

In a mixture of 10 ml. acetone and 10 ml. methanol is dissolved 0.5 g. of 6-benzyloxy-5-chloro-1-hydroxy-2-isopropylideneamino-1,2,3,4-tetrahydronaphthalene and, with the addition of 0.1 g. of 5 % palladium-on-carbon, catalystic reduction is carried out in hydrogen streams until no more hydrogen is absorbed. The catalyst is filtered off and the filtrate is concentrated to dryness and the residue is dissolved in a small amount of ethanolic hydrochloric acid, followed by the addition of 20 ml. of ethyl ether. The resulting crystals are recovered by filtration. The procedure yields 0.2 g. of 5-chloro-2-isopropylamino-1,6-dihydroxy-1,2,3,4-tetrahydronaphthalene hydrochloride as colorless needles melting at 204°–205° C. Mixture-melting of this product with the product according to Example 69 shows no melting point depression.

EXAMPLE 32

In a mixture of 5 ml. methanol and 10 ml. acetone of dissolved 0.3 g. of 6-benzyloxy-5-chloro-2-isopropylideneamino-3,4-dihydro-1(2H)-naphthalenone and, with the addition of 0.1 g. of 5 % palladium-on-carbon, catalystic reduction is carried out until no more hydrogen is absorbed. Thereafter, the reaction mixture is treated in the same manner as Example 31 to obtain 0.1 g. of 5-chloro-2-isopropylamino-1,6-dihydroxy-1,2,3,4-tetrahydronaphthalene hydrochloride. Melting point: 204°–205° C.

EXAMPLE 33

To a solution of 1.0 g. of 2-amino-5-(N-benzoyl-N-methylamino)-6-benzyloxy-3,4-dihydro-1(2H)-naphthalenone hydrochloride in 20 ml. of methanol is added 0.5 g. of sodium borohydride and the mixture is stirred under cooling with ice for 30 minutes. The reaction mixture is admixed with 100 ml. of water and extracted with ethyl acetate. The extract is washed with water, dried and concentrated under reduced pressure. The residue is recrystallized from a mixture of ethyl acetate and ethyl ether to obtain 0.6 g. of trans-2-amino-5-(N-benzoyl-N-methylamino)-6-benzyloxy-1-hydroxy-1,2,3,4-tetrahydronaphthalene as colorless prisms melting at 192°–194° C.

Elemental analysis: for $C_{25}H_{26}O_3N_2$; Calculated C, 74.60; H, 6.51; N, 6.9; Found C, 74.45; H, 6.70; N, 6.77.

NMR spectrum $(CDCl_3)$ $\delta$ : 4.10(1H,d,J=8Hz)

EXAMPLE 34

To a solution of 1.2 g. of trans-6-benzyloxy-5-(N-benzyl-N-methylamino)-2-ethoxycarbonylamino-1-hydroxy-1,2,3,4-tetrahydronaphthalene in 50 ml. of tetrahydrofuran is added 0.6 g. of lithium aluminum hydride, and the mixture is refluxed with stirring for 2 hours. After cooling, the reaction mixture is admixed with water decompose the excess reagent and the insoluble are filtered off. The filtrate is dried and concentrated under reduced pressure. The resulting oil substance is dissolved in 10 ml of methanol, and after the addition of an ethereal solution of oxalic acid, allowed to stand at room temperature. The procedure yields 1.0 g. of trans-6-benzyloxy-5-(N-benzyl-N-methylamino)-1-hydroxy-2-methylamino-1,2,3,4-tetrahydronaphthalene oxalate. Melting point: 191°–192° C(decomp.).

Elemental analysis; for $C_{26}H_{30}O_2N_2 \cdot C_2H_2O_4$; Calculated C, 68.24; H, 6.55; N, 5.69; Found C, 68.05; H, 6.41; N, 5.52.

EXAMPLE 35

1.2 g. of trans-2-acetylamino-6-benzyloxy-5-(N-benzyl-N-methylamino)-1-hydroxy-1,2,3,4-tetrahydronaphthalene is subjected to the same reduction procedure as described in Example 34 except 3 hour-reflux to obtain 0.9 g. of trans-6-benzyloxy-5-(N-benzyl-N-methylamino)-2-ethylamino-1-hydroxy-1,2,3,4-tetrahydronaphthalene oxalate. Melting point: 178°–180° C.

Elemental analysis; for $C_{27}H_{32}O_2N_2 \cdot C_2H_2O_4$; Calculated C, 68.75; H, 6.77; N, 5.53; Found C, 68.70; H, 6.54; N, 5.38.

EXAMPLE 36

In 640 ml. of benzene is suspended 31 g. of 5-(N-benzyloxycabonyl-N-methylamino)-6-benzyloxy-1-(p-toluenesulfonyloxyimino)-1,2,3,4-tetrahydronaphthalene and a potassium ethoxide solution, prepared from 2.6 g. potassium metal and 78 ml. ethanol, is added dropwise under cooling with ice. The reaction mixture is allowed to stand in the cold for 3 days and the resulting crystals are filtered off. To the filtrate is added 140 ml. of 10 % hydrochloric acid, followed by concentration under reduced pressure at a temperature not exceeding 400° C.

The residue (crude 2-amino-5(N-benzyloxycarbonyl-N-methylamino)-6-benzyloxy-3,4-dihydro-1(2H)-naphthalenone hydrochloride) is dissolved in 300 ml. of methanol and, under cooling with ice, 10 g. of sodium borohydride is added. After stirring for 1 hour, 1 l. of water is added and the mixture is extracted with ehtyl acetate. The extract is washed with water, dried and concentrated under reduced pressure. The residue is dissolved in 100 ml. of alcoholic hydrochloric acid and, following treatment with activated carbon, ethyl ether is added. On standing, there is obtained 7.5 g. of trans-2-amino-5-(N-benzyloxycarbonyl-N-methylamino)-6-benzyloxy-1-hydroxy-1,2,3,4-tetrahydronaphthalene hydrochloride as colorless needles melting at 145°–147° C.

Elemental analysis; for $C_{26}H_{28}O_4N_2 \cdot HCl$; Calculated C, 66.66; H, 6.22; N, 5.96; Found C, 66.40; H, 6.01; N, 5.70.

NMR spectrum $(DMSO-d_6)$ $\delta$ : 4.75(1H,d,J=9Hz)

EXAMPLE 37

In a mixture of 15 m. acetone and 20 ml. methanol is dissolved 450 mg. of trans-2-amino-6-benzyloxy-5-cyano-1-hydroxy-1,2,3,4-tetrahydronaphthalene hydrochloride and, while nitrogen gas is introduced, 150 mg. of the adduct of lithium cyanoborohydride-dioxane complex is added in small portions at 5°–10° C. After stirring for 2 hours, a saturated aqueous solution of sodium chloride is added and the mixture is extracted with ethyl acetate. The ethyl acetate layers are washed with a saturated aqueous solution of sodium chloride and dried. The solvent is distilled off under reduced pressure and the residue is recrystallized from ethanol-ethyl acetate. The procedure yields white crystals of trans-6-benzyloxy-5-cyano-1-hydroxy-2-isopropylamino-1,2,3,4-tetrahydronaphthalene. This compound is in agreement with the sample according to the prcedure of Example 3. Yield 297 mg.

EXAMPLE 38

To a solution of 5.0 g. of 2-amino-6-benzyloxy-1-hydroxy-5-nitro-1,2,3,4-tetrahydronaphthalene hydrochloride in 50 ml. of methanol are added 5.0 g. of lithium cyanoborohydride and 150 ml. of acetone, and the mixture is stirred at room temperature for 3 hours. The reaction mixture is added in water and the resulting crystals are recovered by filtration, rinsed with water, dried and dissolved in alcoholic hydrochloric acid. After treatment with activated carbon, ethyl ether is added, whereupon 4.7 g. of 6-benzyloxy-2-isopropylamino-5-nitro-1-hydroxy-1,2,3,4-tetrahydronaphthalene hydrochloride is obtained as colorless needles melting at 268°–270° C.

EXAMPLE 39

The procedure similar to that of Example 37 is conducted using 0.3 g. of 2-amino-6-benzyloxy-1-hydroxy-5-(2-hydroxyethyl)-1,2,3,4-tetrahydronaphthalene hydrochloride to obtain 0.15 g. of 6-benzyloxy-1-hydroxy-5-(2-hydroxyethyl)-2-isopropylamino-1,2,3,4-tetrahydronaphthalene as amorphous powders.

Elemental analysis; for $C_{22}H_{29}O_3N$; Calculated C, 74.33; H, 8.22; N, 3.94; Found C, 74.01; H, 7.98; N, 4.14;

EXAMPLE 40

In a manner similar to that of Example 37, 300 mg. of trans-2-amino-6-benzyloxy-1-hydroxy-5-hydroxymethyl-1,2,3,4-tetrahydronaphthalene is reduced in the presence of 10 ml. of acetone to obtain 250 mg. of trans-6-benzyloxy-1-hydroxy-5-hydroxymethyl-2-isopropylamino-1,2,3,4-tetrahydronaphthalene.

EXAMPLE 41

In a manner similar to that of Example 37, 0.5 g. of 2-amino-6-benzyloxy-5-chloro-1-hydroxy-1,2,3,4-tetrahydronaphthalene hydrochloride is reduced in the presence of 30 ml. of acetone to obtain 0.3 g. of 6-benzyloxy-5-chloro-2-isopropylamino-1-hydroxy-1,2,3,4-tetrahydronaphthalene hydrochloride as colorless needles melting at 265–267° C.

Elemental analysis; for $C_{20}H_{25}O_2NCl \cdot HCl \cdot H_2O$; Calculated C, 60.00; H, 6.80; N, 3.50; Found C, 59.96; H, 6.83; N, 3.42.

EXAMPLES 42–45

By procedures similar to that of Example 37, the products listed below in the table are obtained.

| Example | Carbonyl compound | R¹ (Product) | Melting point °C(decomp.) |
|---|---|---|---|
| 42 | O=C(CH₃)(CH₂CH₃) | —CH(CH₃)(CH₂CH₃) | 250–252 |
| 43 | O=C(CH₃)(CH(CH₃)CH₃) | —CH(CH₃)(CH(CH₃)CH₃) | 250–253 |
| 44 | O=C(CH₃)(CH₂—CH(CH₃)CH₃) | —CH(CH₃)(CH₂—CH(CH₃)CH₃) | 225–227 |
| 45 | CH₃-cyclohexanone (O=) | CH₃-cyclohexyl (=) | 260–263 |

(trans starting material with NO₂, BzO, OH, NH₂ → trans product with NO₂, BzO, OH, NHR'·HCl via Carbonyl compound / LiBH₃CN)

EXAMPLE 46

A procedure similar to that of Example 37 is conducted using 450 mg. of 2-amino-5-cyano-1,6-dihydroxy-1,2,3,4-tetrahydronaphthalene hydrochloride to obtain colorless crystals of 5-cyano-1,6-dihydroxy-2-isopropylamino-1,2,3,4-tetrahydronaphthalene. Melting point: 183°–185° C (decomp.). Mixture-melting of this compound with the sample according to Example 73 shows no melting-point depression. The two products are also identical in NMR spectrum. Yield 300 mg.

EXAMPLE 47

A procedure similar to that of Example 37 is conducted using 0.5 g. of 2-amino-1,6-dihydroxy-5-ureido-1,2,3,4-tetrahydronaphthalene and the resulting oily product is dissolved in methanolic hydrochloric acid, followed by the addition of acetone.

The procedure yields 0.2 g. of 1,6-dihydroxy-2-isopropylamino-5-ureido-1,2,3,4-tetrahydronaphthalene hydrochloride. Melting point: 198°–200° C(decomp.). Mixture-melting of this product with the sample according to Example 127 shows no melting-point depression.

EXAMPLE 48

To a solution of 0.5 g. of 2-amino-6-benzyloxy-5-(N-benzyl-N-methanesulfonylamino)-1-hydroxy-1,2,3,4-tetrahydronaphthalene hydrochloride in 10 ml. of ethanol are added 5 ml. of acetone and 0.3 g. of lithium cyanoborohydride and the mixture is agitated at room temperature for 1 hour. To this reaction mixture is added 10% hydrochloric acid, followed by the addition of a small amount of water. The solution is rendered alkaline with a saturated aqueous solution of sodium hydrogen carbonate and extracted with ethyl acetate. The extract is washed with water, dried and concentrated under reduced pressure. The residue is dissolved in alcoholic hydrochloric acid, followed by the addition of ethyl ether. The resulting crystals are recovered by filtration. The procedure yields 0.3 g. of 6-benzyloxy-5-(N-benzyl-N-methanesulfonylamino)-1-hydroxy-2-isopropylamino-1,2,3,4-tetrahydronaphthalene hydrochloride as colorless needles melting at 212°–214° C.

Elemental analysis; for $C_{28}H_{34}O_4N_2S \cdot HCl$; Calculated C, 60.18; H, 6.31; N, 5.02; Found C, 60.29; H, 6.46; N, 5.20.

EXAMPLE 49

In a manner similar to that of Example 48, 2.0 g. of trans-2-amino-6-benzyloxy-5-(N-benzyloxycarbonyl-N-methylamino)-1-hydroxy-1,2,3,4-tetrahydronaphthalene hydrochloride is reduced in the presence of acetone to obtain 1.5 g. of trans-6-benzyloxy-5-(N-benzyloxycarbonyl-N-methylamino)-1-hydroxy-2-isopropylamino-1,2,3,4-tetrahydronaphthalene hydrochloride. Melting point: 224°–225° C.

Elemental analysis; for $C_{29}H_{34}O_4N_2 \cdot HCl$; Calculated C, 68.15; H, 6.90; N, 5.48; Found C, 67.85; H, 7.00; N, 5.54.

EXAMPLE 50

To a solution of 1.0 g. of 2-amino-6-benzyloxy-1-hydroxy-5-nitro-1,2,3,4-tetrahydronaphthalene hydrochloride in 30 ml. of methanol are added 3.0 g. of phenylacetone and 1.0 g. of sodium cyanoborohydride and the mixture is agitated at room temperature for 5 hours. Following addition of water, the reaction mixture is admixed with 10% hydrochloric acid and rendered alkaline with sodium bicarbonate. The resulting oily residue is extracted with ethyl acetate and the extract is washed with water, dried and concentrated under reduced pressure. The residue is dissolved in alcoholic hydrochloric acid, followed by the addition of ethyl ether. The resulting crystals are recovered by filtration and dried. The procedure yields 0.8 g. of 6-benzyloxy-1-hydroxy-2-(α-methylphenethylamino)-5-nitro-1,2,3,4-tetrahydronaphthalene hydrochloride as colorless needles melting at 204°–206° C.

Elemental analysis; for $C_{26}H_{28}O_4N_2 \cdot HCl$; Calculated C, 66.58; H, 6.23; N, 5.98; Found C, 66.50; H, 6.04; N, 5.59.

EXAMPLE 51

In a manner similar to that of Example 50, 1.0 g. of 2-amino-6-benzyloxy-1-hydroxy-5-nitro-1,2,3,4-tetrahydronaphthalene hydrochloride is reduced in the presence of 3.0 g. of p-hydroxyphenylacetone to obtain 0.7 g. of 6-benzyloxy-1-hydroxy-2-(α-methyl-p-hydroxyphenethylamino)-5-nitro-1,2,3,4-tetrahydronaphthalene hydrochloride as colorless needles melting at 232°–234° C.

Elemental analysis; for $C_{26}H_{28}O_5N_2 \cdot HCl$; Calculated C, 64.39; H, 6.02; N, 5.78; Found C, 64.00; H, 6.21; N, 5.53.

EXAMPLE 52

In a manner similar to that of Example 50, 2-amino-6-benzyloxy-1-hydroxy-5-nitro-1,2,3,4-tetrahydronaphthalene hydrochloride is reduced in the presence of 3.0 g. of p-methoxyphenylacetone to obtain 0.7 g. of 6-benzyloxy-1-hydroxy-2-(α-methyl-p-methoxyphenethylamino)-5nitro-1,2,3,4-tetrahydronaphthalene hydrochloride as colorless needles melting at 228°–230° C.

Elemental analysis; for $C_{27}H_{30}O_5N_2 \cdot HCl$; Calculated C, 64.98; H, 6.26; N, 5.62; Found C, 64.95; H, 5.86; N, 5.86.

EXAMPLE 53

In a manner similar to that of Example 50, 1.0 g. of 2-amino-6-benzyloxy-1-hydroxy-5-nitro-1,2,3,4-tetrahydronaphthalene hydrochloride is reduced in the present of 3.0 g. of methoxyacetaldehyde to obtain 0.7 g. of 6-benzyloxy-1-hydroxy-2-(2-methoxyethylamino)-5-nitro-1,2,3,4-tetrahydronaphthalene hydrochloride as colorless needles melting at 195°–197° C.

Elemental analysis; for $C_{20}H_{24}O_2N_5 \cdot HCl \cdot C_2H_5OH$; Calculated C, 58.07; H, 6.87; N, 6.16; Found C, 58.32; H, 6.69; N, 5.85.

EXAMPLE 54

In a manner similar to that of Example 50, 1.0 g. of 2-amino-6-benzyloxy-1-hydroxy-5-nitro-1,2,3,4-tetrahydronaphthalene hydrochloride is reduced in the presence of 1.0 g. of acrolein dimer to obtain 0.4 g. of 6-benzyloxy-1-hydroxy-5-nitro-2-(3,4-dihydro-2H-pyran-2-yl)-methylamino-1,2,3,4-tetrahydronaphthalene as colorless needles melting at 175°–178° C.

Elemental analysis; for $C_{23}H_{26}O_5N_2$; Calculated C, 67.30; H, 6.39; N, 6.38 Found C, 67.36; H, 6.31; N, 6.51.

EXAMPLE 55

In a manner similar to that of Example 50, 1.0 g. of 2-amino-6-benzyloxy-1-hydroxy-5-nitro-1,2,3,4-tetrahydronaphthalene hydrochloride is reduced in the presence of 3.0 g. of cyclohexanone to obtain 0.7 g. of 6-benzyloxy-2-cyclohexylamino-1-hydroxy-5-nitro-1,2,3,4-tetrahydronaphthalene hydrochloride as colorless needles (recrystallized from ethanol-ethyl ester) melting at 271°–273° C (decomp.). Elemental analysis; for $C_{23}H_{28}O_4N_2 \cdot HCl \cdot H_2O$; Calculated C, 61.39; H, 6.72; N, 6.23; Found C, 62.01; H, 6.42; N, 6.17.

EXAMPLE 56

In a manner similar to that of Example 50, 1.0 g. of trans-2-amino-6-benzyloxy-5-(N-benzyloxycarbonyl-N-methylamino)-1-hydroxy-1,2,3,4-tetrahydronaphthalene hydrochloride is reduced in the presence of 30 ml. of cyclohexanone to obtain 1.0 g. of trans-6-benzyloxy-5-(N-benzyloxycarbonyl-N-methylamino)-2-cyclohexylamino-1,2,3,4-tetrahydronaphthalene hydrochloride, Melting point: 152°–153° C(decomp.).

Elemental analysis; $C_{32}H_{38}O_4N_2 \cdot HCl$; Calculated C, 69.74; H, 7.13; N, 5.08; Found C, 69.71; H, 7.10; N, 5.04.

EXAMPLE 57

In a manner similar to that of Example 50, 1.0 g. of trans-2-amino-6-benzyloxy-5-(N-benzyloxycarbonyl-N-methylamino)-1-hydroxy-1,2,3,4-tetrahydronaphthalene hydrochloride is reduced in the presence of 3.0 g. of p-methoxyphenylacetone to obtain 1.0 g. of trans-6-benzyloxy-5-(N-benzyloxycarbonyl-N-methylamino)-1-hydroxy-2-(α-methyl-p-methoxyphenethylamino)-1,2,3,4-tetrahydronaphthalene hydrochloride. Melting point: 143°–147° C(decomp.).

Elemental analysis; for $C_{36}H_{39}O_5N_2 \cdot HCl$; Calculated C, 70.17; H, 6.54; N, 4.55; Found C. 69.92; H, 6.36; N, 4.50.

EXAMPLE 58

To a solution of 1.0 g. of 2-amino-6-benzyloxy-1-hydroxy-5-nitro-1,2,3,4-tetrahydronaphthalene hydrochloride in 30 ml. of methanol are added 1.0 g. of 3-indolylacetone and 1.0 g. of lithium cyanoborohydride, and the mixture is stirred at room temperature for 3 hours. The reaction mixture is diluted with water and extracted with ethyl acetate. The extract is washed with water, dried and concentrated under reduced pressure. The residue is purified by column chromatography on silica gel (eluted with acetonebenzene=1:1) to recover 0.5 g. of an oily product. This oil is treated with alcoholic hydrochloric acid and the resulting hydrochloride is recrystallized from methanolethyl ether. The procedure yields 0.5 g. of 6-benzyloxy-1-hydroxy-2-(2-(3-indolyl)-1-methyl)ethylamino-5-nitro-1,2,3,4-tetrahydronaphthalene hydrochloride as pale-red needles melting at 215°–217° C.

Elemental analysis; for $C_{28}H_{29}O_4N_3 \cdot HCl$; Calculated C, 66.20; H, 5.95; N, 8.27; Found C, 65.99; H, 5.81; N, 8.13.

EXAMPLE 59

In 20 ml. of methanol is dissolved 1.0 g. of trans-2-amino-6-benzyloxy-1-hydroxy-5-methoxycarbonyl-1,2,3,4-tretrahydronaphthalene, followed by the addition of 500 mg. of cyclobutanone. Under cooling with ice, 500 mg. of lithium cyanoborohydride is added and the mixture is stirred for 3 hours, after which time it is concentrated under reduced pressure. The residue is diluted with water and extracted with ethyl acetate. The organic layer is washed with water, dried and concentrated under reduced pressure. The residue is recrystallized from ethyl acetate-n-hexane. The procedure yields trans-6-benzyloxy-2-cyclobutylamino-1-hydroxy-5-methoxycarbonyl-1,2,3,4-tetrahydronaphthalene as colorless needles melting at 117°–119° C.

NMR spectrum $(CDCl_3)$ δ : 4.26(1H,d,J=8Hz)

Elemental analysis; for $C_{23}H_{27}NO_4$; Calculated C, 72.42; H, 7.13; N, 3.67; Found C, 72.16; H, 7.08; N, 3.65.

EXAMPLES 60-63

In manners similar to that of Example 59, the products listed below in the table are obtained by reducing trans-2-amino-6-benzyloxy-1-hydroxy-5-methoxycarbonyl-1,2,3,4-tetrahydronaphthalene in the presence of the corresponding carbonyl compounds indicated in the table:

| Example | Carbonyl compound | Product* |
|---|---|---|
| 60 | cyclobutanone | cyclobutyl |
| 61 | cyclohexanone | cyclohexyl |
| 62 | p-methoxyphenylacetone (CH₃-CO-CH₂-C₆H₄-OCH₃) | α-methyl-p-methoxyphenethyl |
| 63 | p-hydroxyphenylacetone (CH₃-CO-CH₂-C₆H₄-OH) | α-methyl-p-hydroxyphenethyl |

*Physico-chemical properties of the product
Appearance of crystals
(Salt)    Melting    Elemental analysis

| Example | (Solvent for recrystallization) | point °C | NMR spectrum, δ (Solvent) | Calculated (Found) |
|---|---|---|---|---|
| 60 | Colorless needles (Ethyl acetate-n-hexane) | 102–104 | 4.31(H,d,J=8Hz) (CDCl$_3$) | C$_{24}$H$_{29}$NO$_4$<br>C 72.88. H 7.39. N 3.54<br>(C 72.76. H 7.38. N 3.46) |
| 61 | Colorless needles (Ethyl acetate-n-hexane) | 111–113 | 4.25(1H,d,J=8Hz) (CDCl$_3$) | C$_{25}$H$_{31}$NO$_4$<br>C 73.32. H 7.63. N 3.42<br>(C 73.18. H 7.52. N 3.32) |
| 62 | Colorless crystals (Ethyl acetate-n-hexane) | 84–86 | 4.18(1H,d,J=9Hz) (CDCl$_3$) | C$_{29}$H$_{35}$NO$_5$<br>C 72.93. H 7.39. N 2.93<br>(C 73.03. H 7.00. N 2.97) |
| 63 | Colorless crystals (hydrochloride) (Acetone-ethyl ether) | 182–192 (decomp.) | 4.80(1H,d,J=9Hz) (DMSO-d$_6$+D$_2$O) | C$_{28}$H$_{37}$NO$_5$ . HCl<br>C 67.25. H 6.85. N 2.80<br>(C67.10. H 6.26. N 2.76) |

EXAMPLE 64

In a manner similar to that of Example 59, 712 mg. of 2-amino-6-benzylozy-1-hydroxy-5-methanesulfonylmethyl-1,2,3,4-tetrahydronaphthalene acetate is reduced in the presence of 15 ml. of acetone to obtain 660 mg. of 6-benzyloxy-1-hydroxy-2-isopropylamino-5-methanesulfonylmethyl-1,2,3,4-tetrahydronaphthalene acetate as colorless crystals melting at 86°–91° C(recrystallized from ethyl acetate-ethyl ether).

NMR spectrum (DMSO-d$_6$) δ : 1.06-1.21(6H,m), 2.82(3H,s), 4.49(2H,s), 5.25(2H,s)

EXAMPLE 65

In a manner similar to that of Example 59, 1.0 g. of trans-2-amino-6-benzyloxy-1-hydroxy-5-nitro-1,2,3,4-tetrahydronaphthalene hydrochloride is reduced in the presence of 1.0 g. of cyclobutanone to obtain 0.7 g. of trans-6-benzyloxy-2-cyclobutylamino-1-hydroxy-5-nitro-1,2,3,4-tetrahydronaphthalene hydrochloride as colorless needles melting at 242°–244° C.

Elemental analysis; for C$_{21}$H$_{24}$O$_4$N$_2$·HCl; Calculated C, 62.29; H, 6.22; N, 6.92; Found C, 61.81; H, 6.44; N, 6.61.

NMR spectrum (DMSO:d$_6$) δ : 4.90(1H,d,J=9Hz)

EXAMPLE 66

In a manner similar to that of Example 59, 1.0 g. of trans-2-amino-5-(N-benzyloxycarbonyl-N-methylamino)-6-benzyloxy-1-hydroxy-1,2,3,4-tetrahydronaphthalene hydrochloride is reduced in the presence of 1.0 g. of cyclobutanone to obtain trans-5-(N-benzyloxycarbonyl-N-methylamino 6-benzyloxy-2-cyclobutylamino-1-hydroxy-1,2,3,4-tetrahydronaphthalene oxalate as colorless needles melting at 119°–121° C(recrystallized from ethyl acetate-ethyl ether).

Elemental analysis; for C$_{30}$H$_{34}$O$_4$N$_2$·C$_2$H$_2$O$_4$; Calculated C, 66.65; H, 6.27; N, 4.86; Found C, 66.44; H, 6.30; N, 4.58.

NMR spectrum (DMSO-d$_6$) δ : 4.80(1H,d,J=8Hz)

EXAMPLE 67

500 mg. of trans-2-amino-6-benzyloxy-1hydroxy-5-methoxycarbonyl-1,2,3,4-tetrahydronaphthalene is dissolved in a mixture of 3 ml. of acetone and 10 ml. of anhydrous benzene and the solution is heated on reflux for 5 hours. The reaction mixture is concentrated under reduced pressure and 10 ml. of ethanol is added to the residue. After the addition of 100 mg. of sodium borohydride with stirring, the mixture is stirred at room temperature for 5 hours. The reaction mixture is concentrated under reduced pressure, and water and ethyl acetate are added to the residue. The mixture is extracted with ethyl acetate. The organic solvent layers are pooled, washed with water, dried and concentrated under reduced pressure. The residue is recrystallized from ethyl acetate-n-hexane to obtain trans-6-benzyloxy-2isopropylamino-1-hydroxy-5-methoxycarbonyl-1,2,3,4-tetrahydronaphthalene as colorless needles melting at 91°–92° C.

Elemental analysis; for C$_{22}$H$_{27}$NO$_4$; Calculated C, 71.52; H, 7.37; N, 3.79 Found C, 71.05; H, 7.46; N, 3.59.

EXAMPLE 68

6.0 g. of trans-2-amino-5-(N-benzyl-N-methylamino)-6-benzyloxy-1-hydroxy-1,2,3,4-tetrahydronaphthalene oxalate is dissolved in 100 ml. of water, and the solution is rendered alkaline with sodium bicarbonate and extracted with ethyl acetate. The extract is washed with water, dried, concentrated under reduced pressure and the residue is dissolved in a mixture of 60 ml. of methanol and 180 ml. of acetone. Ater the addition of 1 ml. of alcoholic hydrochloric acid, 6.0 g. of lithium cyanoborohydride is added to the solution and the mixture is stirred at room temperature for 3 hours, after which time 10 % hydrochloric acid is added to decompose the excess reagent. The reaction mixture is admixed with 300 ml. of water, rendered alkaline with sodium bicarbonate and extracted with ethyl acetate. The extract is washed with water, dried and concentrated under reduced pressure. The residue is dissolved in 10 ml. of methanol, admixed with ethereal solution of oxalic acid, and the solution is allowed to stand at room temperature to obtain 4.2 g. of trans-5-(N-benzyl-N-methylamino)-6-benzyloxy-1-hydroxy-2-isopropylamino-1,2,3,4-tetrahydronaphthalene oxalate melting at 193°–195° C.

Elemental analysis; for C$_{27}$H$_{32}$O$_2$N$_2$·C$_2$H$_2$O$_4$; Calculated C, 68.75; H, 6.77; N, 5.53; Found C, 68.55; H, 7.00; N, 5.40.

MNR spectrum DMSO-d$_6$) δ : 4.80(1H, d,J=9Hz)

EXAMPLE 69

To 3 ml. of trifluoroacetic acid is added 0.3 g. of 6-benzyloxy-5-chloro-2-isopropylamino-1-hydroxy-1,2,3,4-tetrahydronaphthalene hydrochloride and the mixture is heated on a water bath at 80° C for 1 hour. The trifluoroacetic acid is distilled off under reduced pressure and a small amount of ethanolic hydrochloric acid is added to the residue, following by the addition of ethyl ether. The resulting crystals are recrystallized from ethanol-ethyl ether. The procedure provides 0.1 g. of 5-chloro-2-isopropylamino-1,6-dihydroxy-1,2,3,4-tetrahydronaphthalene hydrochloride melting at 204°–205° C.

Elemental analysis; for $C_{13}H_{18}O_2NCl\cdot HCl$; Calculated C, 53.43; H, 6.55; N, 4.79; Found C, 53.50; H, 6.48; N, 4.49.

EXAMPLE 70

To 20 ml. of benzene are added 1g. of 5-chloro-1-hydroxy-6-methoxy-2-isopropylamino-1,2,3,4-tetrahydronaphthalene and 3 g. of aluminum chloride, and the mixture is refluxed for 3 hours. The mixture is extracted with 5 ml. of 1% hydrochloric acid and the aqueous layer is filtered to remove the insolubles. The filtrate is evaporated to dryness under reduced pressure and the residue is extracted with 5 m. of ethanol, followed by the addition of ethyl ether. The procedure provides 0.3 g. of 5-chloro-2-isopropylamino-1,6-dihydroxy-1,2,3,4-tetrahydronaphthalene hydrochloride as a precipitate. This product is recrystallized from ethanol-ethyl ether. Melting point: 204°–205° C. Mixture-melting with the product according to Example 69 shows no melting point depression.

EXAMPLE 71

To 20 ml. of ethanol is added 30 mg. of 5% palladium-on-carbon, followed by purging with hydrogen. To the mixture is added 103 mg. of trans-6-benzyloxy-1-hydroxy-5-hydroxymethyl-2-isopropylamino-1,2,3,4-tetrahydronaphthalene, followed by shaking in a current of hydrogen at room temperature.

In 1 hour, about 9 ml. of hydrogen has been absorbed. The catalyst is filtered off and the filtrate is concentrated under reduced pressure. The residue is recrystallized from ethanol-ethyl acetate. The above procedure yields trans-1,6-dihydroxy-5-hydroxymethyl-2-isopropylamino-1,2,3,4-tetrahydronaphthalene as white crystals. Yield 55 mg.; melting point: 182°–185° C (decomp.).

Elemental analysis; for $C_{14}H_{21}O_3N\cdot\frac{1}{2}H_2O$; Calculated C, 64.59; H, 8.52; N, 5.38; Found C, 64.84; H, 8.49; N, 5.32.

EXAMPLE 72

In a manner similar to that of Example 71, 86 mg. of trans-2-amino-6-benzyloxy-1-hydroxy-5-hydroxymethyl-1,2,3,4-tetrahydronaphthalene is catalytically hydrogenated to obtain trans-2-amino-1,6-dihydroxy-5-hydroxymethyl-1,2,3,4,-tetrahydronaphthalene. The anisate of this compound, on recrystallization from ethyl acetate-ethanol, gives white prisms. Yield 43 mg.; melting point: 120°–123° C(decomp.).

Elemental analysis; for $C_{11}H_{15}O_3N\cdot C_8H_8O_3\cdot H_2O$; Calculated C, 60.15; H, 6.64; N, 3,69; Found C, 59.92; H, 6.26; N, 3.92.

EXAMPLE 73

In the manner similar to that of Example 71, 200 mg. of trans-6-benzyloxy-5-cyano-1-hydroxy-2-isopropylamino-1,2,3,4-tetrahydronaphthalene is catalytically hydrogenated to obtain trans-5-cyano-1,6-dihydroxy-2-isopropylamino-1,2,3,4-tetrahydronaphthalene as white crystals (recrystallized from ethanol-ethyl acetate). Yield 113 mg.; melting point: 183°–185° C(decomp.).

NMR spectrum (DMSO-$d_6$) δ: 4.17(1H,d,J=7Hz)

Elemental analysis; for $C_{14}H_{18}O_2N_2\cdot\frac{1}{2}H_2O$; Calculated C, 65.86; H, 7.50; N, 10.91; Found C, 65.94; H, 7.42; N, 10.53.

EXAMPLE 74

150 mg. of trans-6-benzyloxy-5-cyano-1-hydroxy-2-isopropylamino-1,2,3,4-tetrahydronaphthalene hydrochloride is catalytically reduced in a manner similar to that of Example 71 to obtain trans-5-cyano-1,6-dihydroxy-2-isopropylamino-1,2,3,4-tetrahydronaphthalene hydrochloride. Yield 97 mg.; melting point: 246°–248° C(decomp.).

NMR spectrum (DMSO-$d_6$+$D_2O$) δ: 4.72(1H,d,J=8Hz)

Elemental analysis; for $C_{14}H_{18}O_2N_2\cdot HCl\cdot H_2O$; Calculated C, 55.90; H, 7.04; N, 9.31; Found C, 56.37; H, 6.65; N, 9.14.

EXAMPLE 75

In a manner similar to that of Example 71, 95 mg. of trans-6-benzyloxy-1-hydroxy-2-isopropylamino-5-ureidomethyl-1,2,3,4-tetrahydronaphthalene is catalytically reduced to obtain colorless crystals of trans-1,6-dihydroxy-2-isopropylamino-5-ureidomethyl-1,2,3,4-tetrahydronaphthalene. Yield 48 mg.; melting point: 120°–122° C(decomp.).

Elemental analysis; for $C_{15}H_{23}O_3N_3$; Calculated C, 61.41; H, 7.90; N, 14.33; Found C, 60,89; H, 7.82; N, 13.91.

EXAMPLE 76

In a manner similar to that of Example 71, 0.2 g. of 6-benzyloxy-5-chloro-2-isopropylamino-1-hydroxy-1,2,3,4-tetrahydronaphthalene hydrochloride is catalytically reduced to obtain 0.1 g. of 5-chloro-2-isopropylamino-1,6-dihydroxy-1,2,3,4-tetrahydronaphthalene hydrochloride as colorless needles melting at 204°–205° C. Mixture-melting of this product with the product according to Example 69 shows no melting point depression.

EXAMPLE 77

Using 0.2 g. of 6-benzyloxy-1-hydroxy-5-(2-hydroxyethyl)-2-isopropylamino-1,2,3,4-tetrahydronaphthalene, a procedure similar to that of Example 71 is conducted to obtain 0.1 g. of 1,6-dihydroxy-5-(2-hydroxyethyl)-2-isopropylamino-1,2,3,4-tetrahydronaphthalene as colorless crystalline powder.

Elemental analysis; for $C_{15}H_{23}O_3N$; Calculated C, 67.89; H, 8.74; N, 5.28; Found C, 67.53; H, 8.48; N, 4.91.

EXAMPLE 78

To a solution of 0.3 g. of cis-2-(N-benzyl-N-methylamino)-6-benzyloxy-5-formylamino-1-hydroxy-1,2,3,4-tetrahydronaphthalene in 10 ml. of ethanol is added 0.3 g. of 5% palladium-on-carbon, and catalytic reduction is carried out. After the stoichiometric amount of hydrogen has been absorbed, the catalyst is filtered off. To the filtrate is added an ethereal solution of fumaric acid, followed by recovery of the crystals. The procedure yields 0.2 g. of cis-5-N-formylamino-1,6-dihydroxy-2-methylamino-1,2,3,4-tetrahydronaphthalene fumarate as light-brown needles melting at 198°–201° C(decomp.).

Elemental analysis; for $C_{12}H_{16}O_3N_2\cdot C_4H_4O_4$; Calculated C, 54.54; H, 5.72; N, 7.95; Found C, 54.33; H, 5.82; N, 7.96.

EXAMPLE 79

In a manner similar to that of Example 78, 0.31 g. of trans-2-(N-benzyl-N-methylamino)-6-benzyloxy-5-formylamino-1-hydroxy-1,2,3,4-tetrahydronaphthalene is catalytically reduced to obtain 0.15 g. of trans-5-N-formylamino-1,6-dihydroxy-2-methylamino-1,2,3,4-tetrahydronaphthalene fumarate as colorless crystals melting at 156°–160° C.

Elemental analysis; for $C_{12}H_{16}O_3N_2 \cdot C_4H_4O_4$; Calculated C, 54.54; H, 5.72; N, 7.95; Found C, 54.65; H, 5.88; N, 7.94.

EXAMPLE 80

In a manner similar to that of Example 78, 0.51 g. of cis-2-(N-benzyl-N-methylamino)-6-benzyloxy-1-hydroxy-5-ureido-1,2,3,4-tetrahydronaphthalene is catalytically reduced to obtain 0.2 g. of cis-1,6-dihydroxy-2-methylamino-5-ureido-1,2,3,4-tetrahydronaphthalene hydrochloride as crystalline powder.

NMR spectrum (DMSO-$d_6$) δ: 4.75(1H,d,J=2Hz), 2.60(3H,s)

EXAMPLE 81

In 10 ml. of ethanol is dissolved in 0.2 g. of 6-benzyloxy-5-(N-benzyl-N-methanesulfonylamino)-1-hydroxy-2-isopropylamino-1,2,3,4-tetrahydronaphthalene hydrochloride and, with the addition of 0.2 g. of 10% palladium-on-carbon, catalytic reduction is carried out. After the stoichiometric amount of hydrogen has been absorbed, the catalyst is filtered off, followed by the addition of ethyl ether. The procedure yields 0.1 g. of 1,6-dihydroxy-2-isopropylamino-5-methanesulfonylamino-1,2,3,4-tetrahydronaphthalene hydrochloride as colorless needles melting at 210°–213° C (decomp.).

Elemental analysis; for $C_{14}H_{22}O_4N_2S \cdot HCl$; Calculated C, 47.93; H, 6.61; N, 7.99; Found C, 47.63; H, 6.81; N, 7.47.

EXAMPLE 82

In 70 ml. of ethanol is dissolved 0.7 g. of 6-benzyloxy-1-hydroxy-2-(α-methylphenethylamino)-5-nitro-1,2,3,4-tetrahydronaphthalene hydrochloride and catalytic reduction is carried out in the presence of 0.7 g. of 5% palladium-on-carbon. After the stoichiometric amount of hydrogen has been absorbed, the catalyst is filtered off and 2 ml. of alcoholic hydrochloric acid is added to the filtrate. The mixture is concentrated under reduced pressure and the residue is dissolved in a mixture of methanol and ethyl ether. The solution is allowed to stand in the cold overnight, whereupon pale green crystalline powder separates The powder is recovered by filtration, rinsed with ether and dried. The procedure yields 0.4 g. of 5-amino-1,6-dihydroxy-2-(α-methylphenethylamino)-1,2,3,4-tetrahydronaphthalene hydrochloride.

Elemental analysis; for $C_{19}H_{24}O_2N_2 \cdot 2HCl$; Calculated C, 59.22; H, 6.80; N, 7.27; Found C, 59.01; H, 6.73; N, 7.02.

EXAMPLE 83

In a manner similar to that of Example 82, 0.7 g. of 6-benzyloxy-1-hydroxy-2-(α-methyl-p-hydroxyphenethylamino)-5-nitro-1,2,3,4-tetrahydronaphthalene is catalytically reduced to obtain 0.5 g. of 5-amino-1,6-dihydroxy-2(α-methyl-p-hydroxyphenethylamino)-1,2,3,4-tetrahydronaphthalene hydrochloride as colorless needles (recrystallized from methanol-acetone) melting at 198°–203° C(decomp.).

Elemental analysis; for $C_{19}H_{24}O_3N_2 \cdot 2HCl \cdot 3/2H_2O$; Calculated C, 53.27; H, 6.82; N, 6.54; Found C, 53.44; H, 6.59; N, 6.28.

EXAMPLE 84

In a manner similar to that of Example 82, 0.6 g. of 6-benzyloxy-1-hydroxy-2-(α-methyl-p-methoxyphenethylamino)-5-nitro-1,2,3,4-tetrahydronaphthalene hydrochloride is catalytically reduced to obtain 0.3 g. of 5-amino-1,6-dihydroxy-2-(α-methyl-p-methoxyphenethylamino)-1,2,3,4-tetrahydronaphthalene hydrochloride as colorless needles melting at 189–193° C(recrystallized from methanol-ethyl ether).

Elemental analysis; for $C_{20}H_{26}O_3N_2 \cdot 2HCl$; Calculated C, 57.83; H, 6.79; N, 6.75; Found C, 57.82; H, 6.41; N, 7.01.

EXAMPLE 85

In a manner similar to that of Example 82, 0.5 g. of 6-benzyloxy-1-hydroxy-2-(2-methoxyethylamino)-5-nitro-1,2,3,4-tetrahydronaphthalene is catallytically reduced and the product is converted to its fumarate to obtain 0.2 g. of 5-amino-1,6-dihydroxy-2-(2-methoxyethylamino)-1,2,3,4-tetrahydronaphthalene fumarate as colorless needles melting at 162°–164° C (recrystalized from ethanol-ethyl ether).

Elemental analysis; for $C_{13}H_{20}O_3N_2 \cdot C_4H_4O_4$; Calculated C, 55.49; H, 6.56; N, 7.61; Found C, 55.41; H, 6.87; N, 7.46.

EXAMPLE 86

In a manner similar to that of Example 82, 0.7 g. of 6-benzyloxy-2-cyclohexylamino-1-hydroxy-5-nitro-1,2,3,4-tetrahydronaphthalene hydrochloride is catalytically reduced to obtain 0.4 g. of 5-amino-2-cyclohexylamino-1,6-dihydroxy-1,2,3,4-tetrahydronaphthalene hydrochloride as colorless needles melting at 206°–209° C.

Elemental analysis; for $C_{16}H_{24}O_2N_2 \cdot 2HCl \cdot 3/2H_2O$; Calculated C, 51.20; H, 7.52; N, 7.46; Found C, 51.00; H, 7.24; N, 7.39.

EXAMPLE 87

In a manner similar to that of Example 82, 0.4 g. of 6-benzyloxy-1-hydroxy-5-nitro-2-(3,4-dihydro-2H-pyran-2-yl)-methylamino-1,2,3,4-tetrahydronaphthalene is catalytically reduced, and the product is converted to its fumarate. The procedure yields 0.2 g. of 5-amino-1,6-dihydroxy-2-(3,4,5,6-tetrahydro-2H-pyran-2-yl)methylamino-1,2,3,4-tetrahydronaphthalene fumarate as colorless needles melting at 185°–188° C(recrystallized from ethanol-ethyl ether).

Elemental analysis; for $C_{16}H_{24}O_3N_2 \cdot C_4H_4O_4$; Calculated C, 58.81; H, 6.91; N, 6.86; Found C, 58.59; H, 6.90; N, 7.03.

EXAMPLES 88–91

The products listed in the Table below are obtained by catalytically hydrogenating the corresponding trans-6-benzyloxy-1-hydroxy-2-substituted amino-5-nitro-1,2,3,4-tetrahydronaphthalenes and converting the resulting compounds to their hydrochlorides, in manners similar to that of Example 82.

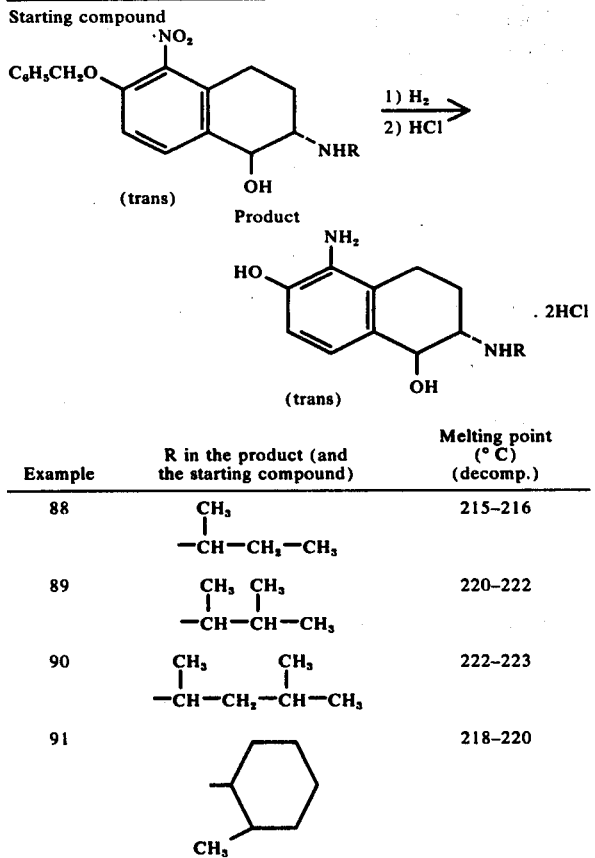

| Example | R in the product (and the starting compound) | Melting point (°C) (decomp.) |
|---|---|---|
| 88 | —CH(CH₃)—CH₂—CH₃ | 215–216 |
| 89 | —CH(CH₃)—CH(CH₃)—CH₃ | 220–222 |
| 90 | —CH(CH₃)—CH₂—CH(CH₃)—CH₃ | 222–223 |
| 91 | cyclohexyl-CH₃ | 218–220 |

EXAMPLE 92

In 20 ml. of methanol is dissolved 200 mg. of trans-2-amino-6-benzyloxy-5-cyano-1-hydroxy-1,2,3,4-tetrahydronaphthalene hydrochloride, followed by the addition of 30 mg. of 5% palladium-on-carbon. The mixture is agitated in hydrogen streams at room temperature for 30 minutes. The catalyst is filtered off and the filtrate is concentrated under reduced pressure. The residue is recrystallized from methanol-ethyl acetate. The procedure yields white crystals of trans-2-amino-5-cyano-1,6-dihydroxy-1,2,3,4-tetrahydronaphthalene hydrochloride. Yield 136 mg.; melting point: 259°–261° C(decomp.).

Elemental analysis; for $C_{11}H_{12}O_2N_2 \cdot HCL \cdot 1/4H_2O$; Calculated C, 53.88; H, 5.55; N, 11.43; Found C, 53.68; H, 5.25; N, 10.91.

EXAMPLE 93

In a manner similar to that of Example 92, 1.2 g. of trans-6-benzyloxy-2-tert-butylamino-5-cyano-1-hydroxy-1,2,3,4-tetrahydronaphthalene is catalytically reduced to obtain trans-2-tert-butylamino-5-cyano-1,6-dihydroxy-1,2,3,4-tetrahydronaphthalene hydrochloride. Melting point: 190°–192° C (decomp.; recrystallized from anthanol-isopropyl ether).

Elemental analysis, for $C_{15}H_{20}O_2N_2 \cdot HCl \cdot C_2H_5OH$; Calculated C, 59.55; H, 7.94; N, 8.17; Found C, 59.12; H, 8.18; N, 8.22.

EXAMPLE 94

In a manner similar to that of Example 92, 520 mg. of trans-6-benzyloxy-2-tert-butylamino-1-hydroxy-5-hydroxymethyl-1,2,3,4-tetrahydronaphthalene is catalytically reduced to obtain 240 mg. of trans-2-tert-butylamino-1,6-dihydroxy-5-hydroxymethyl-1,2,3,4-tetrahydronaphthalene. Melting point: 197°–204° C (decomp.; recrystallized from methanol-ethyl acetate).

Elemental analysis; for $C_{15}H_{23}O_3N$; Calculated C, 67.89; H, 8.74; N, 5.28; Found C, 67.58; H, 8.55; N, 5.40.

EXAMPLE 95

In a manner similar to that of Example 92, 400 mg. of trans-6-benzyloxy-2-tert-butylamino-1-hydroxy-5-methoxycarbonyl-1,2,3,4-tetrahydronaphthalene hydrochlorise is catalytically reduced to obtain285 mg. of trans-2-tert-butylamino-1,6-dihydroxy-5-methoxycarbonyl-1,2,3,4-tetrahydronaphthalene hydrochloride as white crystals melting at 230°–232° C(decomp.; recrystallized from methanol-isopropyl ether).

Elemental analysis, for $C_{16}H_{23}NO_4 \cdot HCl$; Calculated C, 58.26; H, 7.33; N, 4.25; Found C, 58.15; H, 7.52; N, 4.13.

EXAMPLE 96

In a manner similar to that of Example 92, 533 mg. of cis-6-benzyloxy-2-tertbutylamino-1-hydroxy-5-hydroxymethyl-1,2,3,4-tetrahydronaphthalene is catalytically reduced to obtain 279 mg. of cis-2-tert:butylamino-1,6-dihydroxy-5-hydroxymethyl-1,2,3,4-tetrahydronaphthalene as colorless platelets melting at 163°–165° C (decomp.).

NMR spectrum (DMSO-$d_6$) δ: 4.25(1H,d,J=4Hz)

Elemental analysis; for $C_{15}H_{23}O_3N$; Calculated C, 67.89; H, 8.74; N, 5.28; Found C, 67.89; H, 8.98; N, 5.13.

EXAMPLE 97

In a manner similar to that of Example 92, 747 mg. of cis-6-benzyloxy-1-hydroxy-5-hydroxymethyl-2-isopropylamino-1,2,3,4-tetrahydronaphthalene is catalytically hydrogenated to obtain 390 mg. of cis-1,6-dihydroxy-5-hydroxymethyl-2-isopropylamino-1,2,3,4-tetrahydronaphthalene as white crystals melting at 167°–169° C(decomp.).

NMR spectrum (DMSO-$d_6$) δ: 4.40(1H,d,J=4Hz)

Elemental analysis; for $C_{14}H_{21}O_3N$;

Calculated C, 66.90; H, 8.42; N, 5.57; Found C, 66.50; H, 8.94; N, 5.31.

EXAMPLE 98

In 20 ml. of methanol is dissolved 300 mg. of trans-6-benzyloxy-2-cyclobutylamino-1-hydroxy-5-hydroxymethyl-1,2,3,4-tetrahydronaphthalene and catalytic reduction is carried out in the presence of 5% palladium-on-carbon as the catalyst. When no more hydrogen is absorbed, the catalyst is filtered off and 60 mg. of acetic acid is added to the filtrate. The mixture is concentrated under reduced pressure and the residue is recrystallized from methanolethyl acetate. The procedure yields trans-2-cyclobutylamino-1,6-dihydroxy-5-hydroxymethyl-1,2,3,4-tetrahydronaphthalene acetate as colorless platelets melting at 143°–145° C (decomp.)

NMR spectrum (DMSO-$d_6$-$D_2O$) δ: 4.15(1H,d,J=8Hz), 4.48(2H,s)

Elemental analysis; for $C_{15}H_{21}NO_3 \cdot C_2H_4O_2$; Calculated C, 63.14; H, 7.79; N, 4.33; Found C, 63.66; H, 7.71; N, 4.25.

EXAMPLES 99–103

In manners similar to that of Example 98, the products listed in the table below are obtained from the corresponding trans-6-benzyloxy-2-substituted amino-1-hydroxy-5-hydroxymethyl-1,2,3,4-tetrahydronaphthalenes.

EXAMPLE 104

Cis-6-benzyloxy-2-tert-butylamino-5-cyano-1-hydroxy-1,2,3,4-tetrahydronaphthalene is catalytically reduced in a manner similar to that of Example 98, and the resulting product is converted to hydrochloride. The procedure yields cis-2-tert-butylamino-5-cyano-1,6-dihydroxy-1,2,3,4-tetrahydronaphthalene hydrochloride as colorless prisms (recrystallized from

| Example | R$^1$ in the product* (and the starting compound) |
|---|---|
| 99 | cyclohexyl |
| 100 | $-CH(CH_3)CH_2-$C$_6$H$_4$-OCH$_3$ (para) |
| 101 | $-CH(CH_3)CH_2-$C$_6$H$_4$-OH (para) |
| 102 | $-C_3H_7$ |
| 103 | cyclopentyl |

*Physico-chemical properties of the product

| Example | Appearance of crystals [Salt](Solvent for recrystallization) | Melting point °C (decomp.) | NMR spectrum, δ (Solvent) | Elemental analysis Calculated (Found) |
|---|---|---|---|---|
| 99 | Colorless prisms [Acetate] (Methanol ethyl acetate) | 135–137 | 4.25(1H,d,J=8Hz) (DMSO-d$_6$) | C$_{17}$H$_{25}$NO$_3$ . C$_2$H$_4$O$_2$ . H$_2$O<br>C 61.77. H 8.46. N 3.79<br>(C 61.78. H 8.69. N 3.72) |
| 100 | Colorless prisms [Acetate] (Ethanol-isopropyl ether) | 146–148 | 3.88(3H,s)<br>4.26(1H,d,J=8Hz)<br>4.50 (2H,s)<br>6.64(1H,d,J=8Hz)<br>6.78(2H,d,J=8Hz)<br>7.06(2H,d,J=8Hz)<br>7.14(1H,d,J=8Hz)<br>(DMSO-d$_6$) | |
| 101 | Colorless needles (Methanol-ethyl acetate) | 215–220 | 4.56(2H,s)<br>4.78(1H,d,J=9Hz)<br>6.75(2H,d,J=8Hz)<br>6.79(1H,d,J=8Hz)<br>7.10(2H,d,J=8Hz)<br>7.32(1H,d,J=8Hz)<br>(DMSO-d$_6$+D$_2$O) | |
| 102 | Colorless platelets [Acetate] (Methanol-isopropyl ether) | 177–180 | 4.36(1H,d,J=8Hz) (DMSO-d$_6$) | C$_{13}$H$_{19}$NO$_3$ . C$_2$H$_4$O$_2$<br>C 60.59. H 7.80. N 4.71<br>(C 60.26. H 7.88. N 4.71) |
| 103 | Colorless platelets [Acetate] (Methanol-ethyl acetate) | 145–148 | 4.26(1H,d,J=7Hz)<br>4.49(2H,s)<br>(DMSO-d$_6$+D$_2$O) | C$_{16}$H$_{23}$NO$_3$ . C$_2$H$_4$O$_2$ . ½H$_2$O<br>C 63.14. H 8.34. N 4.09<br>(C 63.31. H 8.34. N 3.89) | ethanol-isopropyl ether) melting at 197°–199° C (decomp.).

NMR spectrum (DMSO-d$_6$+D$_2$O) δ: 4.72(1H,d,J=4Hz)

Elemental analysis; for C$_{15}$H$_{20}$N$_2$O$_2$.HCl.H$_2$O; Calculated C, 57.22; H, 7.36; N, 8.90; Found C, 57.28; H, 7.38; N, 8.60.

EXAMPLE 105

Trans-5-aminomethyl-6-benzyloxy-2-tert-butylamino-1-hydroxy-1,2,3,4-tetrahydronaphthalene dihydrochloride is catalytically reduced in a manner similar to that of Example 98, and the resulting product is converted to dihydrochloride. The procedure yields trans-5-aminomethyl-2-tert-butylamino-1,6-dihydroxy-1,2,3,4-tetrahydronaphthalene dihydrochloride as colorless prisms (recrystallized from methanol-ethyl acetate) melting at 247°–250° C(decomp.).

NMR spectrum (DMSO-d$_6$+D$_2$O) δ: 4.62(1H,d,J=9Hz)

Elemental analysis; for C$_{15}$H$_{24}$N$_2$O$_2$.2HCl; Calculated C, 53.41; H, 7.77; N, 8.31; Found C, 53.64; H, 7.80; N, 8.24.

EXAMPLE 106

In the manner similar to that of Example 92, 0.7 g. of trans-6-benzyloxy-1-hydroxy-2-isopropylamino-5-dimethylamino-1,2,3,4-tetrahydronaphthalene hydrochloride is catalytically hydrogenated to obtain 0.35 g. of trans-1,6-dihydroxy-2-isopropylamino-5-dimethylamino-1,2,3,4-tetrahydronaphthalene hydrochloride as colorless needles melting at 220°–222° C(decomp.).

Elemental analysis; for C$_{15}$H$_{24}$O$_2$N$_2$.2HCl; Calculated C, 53.41; H, 7.77; N, 8.31 Found C, 53.25; H, 7.83; N, 8.29.

EXAMPLE 107 a. In a manner similar to that of Example 34, trans-6-benzyloxy-2-ethoxycarbonylamino-1-hydroxy-5-methoxycarbonyl-1,2,3,4-tetrahydronaphthalene is reduced with the use of lithium aluminum hydride to obtain trans-6-benzyloxy-1-hydroxy-5-hydroxymethyl-2-methylamino-1,2,3,4-tetrahydronaphthalene as colorless needles (recrystallized from methanol-ethyl acetate) melting at 172°–173° C.

NMR spectrum (DMSO-d$_6$) δ : 4.37(1H,d,J=8Hz), 4.54(2H,s)

Elemental analysis; for C$_{19}$H$_{23}$NO$_3$.2/3H$_2$O; Calculated C, 70.13; H, 7.54; N, 4.30; Found C, 69.86; H, 7.25; N, 4.19.

b. In a manner similar to that of Example 98, trans-6-benzyloxy-1-hydroxy-5-hydroxymethyl-2-methylamino-1,2,3,4-tetrahydronaphthalene is catalytically reduced and the reaction mixture is purified without the addition of acetic acid to obtain trans-1,6-dihydroxy-5-hydroxymethyl-2-methylamino-1,2,3,4-tetrahydronaphthalene as white crystals (recrystallized from methanol-ethyl acetate) melting at 198°–210° C(decomp.).

NMR spectrum (DMSO-d$_6$) δ : 4.20(1H,d,J=8Hz), 4.47(2H,s)

Elemental analysis; for C$_{12}$H$_{17}$NO$_3$.½H$_2$O; Calculated C, 62.05; H, 7.81; N, 6.03; Found C, 61.75; H, 7.73; N, 5.74.

EXAMPLE 108

To a solution of 0.5 g. of trans-2-amino-5-(N-benzyloxycarbonyl-N-methylamino)-6-benzyloxy-1-hydroxy-1,2,3,4-tetrahydronaphthalene hydrochloride in 20 ml. of methanol is added 0.5 g. of 10% palladium-on-carbon, and catalytic reduction is carried out at atmospheric temperature and pressure. After the stoichiometric amount of hydrogen has been absorbed, the catalyst is filtered off and 20 ml. of ethyl ether is added to the filtrate. The mixture is allowed to stand in the cold to obtain 0.2 g. of trans-2-amino-1,6-dihydroxy-5-methylamino-1,2,3,4-tetrahydronaphthalene hydrochloride as colorless needles melting above 300° C.

Elemental analysis; for C$_{11}$H$_{16}$O$_2$N$_2$.2HCl.H$_2$O; Calculated C, 44.15; H, 6.74; H, 9.30; Found C, 44.35; H, 6.61; H, 9.29.

NMR spectrum (DMSO-d$_6$) δ : 4.61(1H,d,J=8Hz)

EXAMPLE 109

In a manner similar to that of Example 108, 1.0 g. trans-6-benzyloxy-5-(N-benzyloxycarbonyl-N-methylamino)-2-cyclohexylamino-1-hydroxy-1,2,3,4-tetrahydronaphthalene hydrochloride is catalytically hydrogenated to obtain 0.5 g. of trans-2-cyclohexylamino-1,6-dihydroxy-5-methylamino-1,2,3,4-tetrahydronaphthalene hydrochloride as colorless needles melting at 218°–220° C(decomp.).

Elemental analysis; for C$_{17}$H$_{26}$O$_2$N$_2$.2HCl; Calculated C, 56.20; H, 7.77; N, 7.71; Found C, 56.16; H, 7.81; N, 7.55.

EXAMPLE 110

In a manner similar to that of Example 108, 0.9 g. of trans-6-benzyloxy-5-(N-benzoyloxycarbonyl-N-methylamino)-1-hydroxy-2-(α-methyl-p-methoxyphenethylamino)-1,2,3,4-tetrahydronaphthalene hydrochloride is catalytically hydrogenated to obtain 0.4 g. of trans-1,6-dihydroxy-5-methylamino-2-(α-methyl-p-methoxyphenethylamino)-1,2,3,4-tetrahydronaphthalene hydrochloride as colorless needles melting at 216°–218° C(decomp.).

Elemental analysis; for C$_{21}$H$_{27}$O$_3$N$_2$.2HCl; Calculated C, 58.88; H, 6.82; N, 6.54; Found C, 58.70; H, 6.86; N, 6.41.

EXAMPLE 111

In 30 ml. of methanol are suspended 250 mg. of cis-6-benzyloxy-2-(N-benzyl-N-methylamino)-5-cyano-1-hydroxy-1,2,3,4-tetrahydronaphthalene hydrochloride and 5% palladium-on-carbon, and the mixture is agitated in hydrogen streams at room temperature for 30 minutes. After the reaction, the catalyst is filtered off and the filtrate is concentrated under reduced pressure. The procedure provides cis-5-cyano-1,6-dihydroxy-2-methylamino-1,2,3,4-tetrahydronaphthalene hydrochloride as a white precipitate. Recrystallization from ethanol-ethyl acetate provides colorless crystals melting at 226°–227° C(decomp.). Yield 112 mg.

Elemental analysis; for C$_{12}$H$_{14}$O$_2$N.HCl; Calculated C, 56.68; H, 5.94; N, 11.00; Found C, 56.30; H, 6.09; N, 10.88.

EXAMPLE 112

In a manner similar to that of Example 111, 150 mg. of trans-6-benzyloxy-2-(N-benzyl-N-methylamino)-5-cyano-1-hydroxy-1,2,3,4-tetrahydronaphthalene hydrochloride is catalytically hydrogenated to obtain trans-5-cyano-1,6-dihydroxy-2-methylamino-1,2,3,4-tetrahydronaphthalene hydrochloride as a white precipitate. Recrystallization from ethanol-ethyl acetate yields colorless prisms melting at 230°–232° C(decomp.). Yield 65 mg.

Elemental analysis; for $C_{12}H_{14}O_2N.HCl$; Calculaed C, 56.58; H, 5.94; N, 11.00; Found C, 56.13; H, 5.95; N, 10.92.

EXAMPLE 113

In a manner similar to that of Example 111, 1 g. of 2-(N-benzyl-N-methylamino)-6-benzyloxy-1-hydroxy-5-methoxycarbonyl-1,2,3,4-tetrahydronaphthalene is catalytically reduced to obtain 0.3 g. of 1,6-dihydroxy-5-methoxycarbonyl-2-methylamino-1,2,3,4-tetrahydronaphthalene hydrochloride as amorphous powder.

Elemental analysis; for $C_{13}H_{17}O_4N.HCl$; Calculated C, 54.26; H, 6.30; N, 48.69; Found C, 54.00; H, 6.18; N, 48.18.

EXAMPLE 114

To a solution of 0.4 g. of 6-benzyloxy-1-hydroxy-2-[2-(3-indolyl)-1-methyl]ethylamino-5-nitro-1,2,3,4-tetrahydronaphthalene in 20 ml. of methanol is added 0.4 g. of 5% palladium-on-carbon, and catalytic reduction is carried out at atmospheric pressure and temperature. After the stoichiometric amount of hydrogen has beeen absorbed, the catalyst is filtered off and an ethereal solution of fumaric acid is added to the filtrate to make the fumarate. The solution is concentrated to half its volume under reduced pressure, followed by the addition of ethyl ether. The resulting crystals are recovered by filtration. The above procedure yields 0.2 g. of 5-amino-1,6-dihydroxy-2-[2-(3-indolyl)-1-methyl]ethylamino-1,2,3,4-tetrahydronaphthalene fumarate melting above 300° C.

Elemental analysis; for $C_{21}H_{25}O_2N_3.2C_4H_4O_4$; Calculated C, 59.68; H, 5.70; N, 7.20; Found C, 59.44; H, 5.53; N, 7.01.

EXAMPLE 115

In a manner similar to that of Example 114, 0.9 g. of 6-benzyloxy-2-tert-butylamino-1-hydroxy-5-nitro-1,2,3,4-tetrahydronaphthalene is catalytically reduced to obtain 0.4 g. of 5-amino-2-tert-butylamino-1,6-dihydroxy-1,2,3,4-tetrahydronaphthalene fumarate as colorless needles melting above 300° C.

Elemental analysis; for $C_{14}H_{22}O_2N_2.C_4H_4O_4.\frac{1}{2}H_2O$; Calculated C, 57.58; H, 7.25; N, 7.46. Found C, 57.82; H, 7.49; N, 7.86.

NMR spectrum (DMSO-$d_6$) δ : 4.50(1H,d,J=9Hz), 1.32(9H,s)

EXAMPLE 116

6.0 g. of trans-6-benzyloxy-1-hydroxy-2-isopropylamino-5-nitro-1,2,3,4-tetrahydronaphthalene hydrochloride is catalytically reduced in a manner similar to that of Example 114 and the resulting compound is converted to its hydrochloride. The procedure yields 3.5 g. of trans-5-amino-1,6-dihydroxy-2-isopropylamino-1,2,3,4-tetrahydronaphthalene hydrochloride as colorless needles melting at 220°–222° C.

Elemental analysis; for $C_{13}H_{20}O_2N_2.2HCl$; Calculated C, 50.49; H, 7.17; N, 9.06; Found C, 50.47; H, 7.24; N, 8.85.

NMR spectrum (DMSO-$d_6$) δ : 4.80(1H,d,J=9Hz)

EXAMPLE 117

0.7 g. of trans-6-benzyloxy-2-cyclobutylamino-1-hydroxy-5-nitro-1,2,3,4-tetrahydronaphthalene hydrochloride is catalytically reduced in a manner similar to that of Example 114 and the product is converted to its hydrochloride. The procedure yields 0.4 g. of trans-5-amino-2-cyclobutylamino-1,6-dihydroxy-1,2,3,4-tetrahydronaphthalene hydrochloride as colorless needles melting at 205°–207° C (decomp.).

Elemental analysis: for $C_{14}H_{20}O_2N_2.2HCl.3/2H_2O$; Calculated C, 48.27; H, 7.24; N, 8.05; Found C, 48.36; H, 7.26; N, 8.06.

NMR spectrum(DMSO-$d_6$) δ : 4.35(1H,d,J=8Hz)

EXAMPLE 118

200 mg. of 2-amino-6-benzyloxy-1-hydroxy-5-methanesulfonylmethyl-1,2,3,4-tetrahydronaphthalene acetate dissolved in a mixture of 15 ml. ethanol and 0.5 ml. water is catalytically hydrogenated with the use of 5% palladium-on-carbon at atmospheric temperature and pressure. After the stoichiometric amount of hydrogen has been absorbed, the catalyst is filtered off and 0.1 ml. of concentrated hydrochloric acid is added to the filtrate. The ethanol is then distilled off to obtain 2-amino-1,6-dihydroxy-5-methanesulfonylmethyl-1,2,3,4-tetrahydronaphthalene hydrochloride. Melting point: 195°–225° C(slow decomp.).

Elemental analysis; for $C_{12}H_{17}O_4NS.HCl.H_2O$; Calculated C, 44.24; H, 6.19; N, 4.30; Found C, 44.47; H, 5.86; N, 4.12.

EXAMPLE 119

In a manner similar to that of Example 118, 220 mg. of 6-benzyloxy-1-hydroxy-2-isopropylamino-5-methanesulfonylmethyl-1,2,3,4-tetrahydronaphthalene acetate is catalytically hydrogenated to obtain 1,6-dihydroxy-2-isopropylamino-5-methanesulfonylmethyl-1,2,3,4-tetrahydronaphthalene acetate as colorless crystals. Melting point: 160°–190° C(slow decomp.). Elemental analysis; for $C_{15}H_{23}O_4NS.CH_3COOH.H_2O$; Calculated C, 52.16; H, 7.47; N, 3.58; Found C, 52.05; H, 7.20; N, 3.51.

EXAMPLE 120

To a solution of 0.5 g. of trans-5-amino-6-benzyloxy-1-hydroxy-2-isopropylamino-1,2,3,4-tetrahydronaphthalene in 20 ml. of acetic acid is added 1.0 g. of sodium borohydride and the mixture is stirred at room temperature for 7 hours. The reaction mixture is admixed with water, rendered alkaline with sodium bicarbonate and extracted with ethyl acetate. The extract is washed with water, dried and concentrated under reduced pressure to obtain 0.3 g. of crude trans-6-benzyloxy-5-ethylamino-1-hydroxy-2-isopropylamino-1,2,3,4-tetrahydronaphthalene. The compound is dissolved in 10 ml. of methanol and catalytic reduction is carried out in the presence of 0.3 g. of 10% palladium-on-carbon. After the stoichiometric amount of hydrogen has been absorbed, the catalyst is filtered off and 5 ml. of alcoholic hydrochloric acid and 50 ml. of ethyl ether are added to the filtrate. The mixture is allowed to stand at room temperature to obtain 0.1 g. of trans-5-ethylamino-1,6-dihydroxy-2-isopropylamino-1,2,3,4-tetrahydronaphthalene hydrochloride as colorless needles melting at 198°–200° C (decomp.).

Elemental analysis; for $C_{15}H_{24}O_2N_2.2HCl.\frac{1}{2}H_2O$; Calculated C, 52.02; H, 7.86; N, 8.09; Found C, 52.09; H, 7.90; N, 7.62.

EXAMPLE 121

To a solution of 0.5 g. of trans-5-amino-6-benzyloxy-1-hydroxy-2-isopropylamino-1,2,3,4-tetrahydronaphthalene in 20 ml. of acetic acid is added 1.0 g. of sodium borohydride and the mixture is stirred at room temperature for 5 days. The reaction mixture is admixed with water, rendered alkaline with sodium bicarbonate and extracted with ethyl acetate. The extract is washed with water, dried and concentrated under reduced pressure to obtain 0.5 g. of crude trans-6-benzyloxy-5-diethylamino-1-hydroxy-2-isopropylamino-1,2,3,4-tetrahydronaphthalene. The compound is dissolved in 10 ml. of methanol and catalytic reduction is carried out in the presence of 0.5 g. of 10% palladium-on-carbon. After the stoichiometric amount of hydrogen has been absorbed, the catalyst is filtered off and an ethereal solution of fumaric acid is added to the filtrate. The mixture is allowed to stand at room temperature to obtain 0.15 g. of trans-5-diethylamino-1,6-dihydroxy-2-isopropylamino-1,2,3,4-tetrahydronaphthalene hydrochloride as colorless needles melting at 215°–217° C(decomp.).

Elemental analysis; for $C_{17}H_{28}O_2N_2.C_4H_4O_4$; Calculated C, 61.74; H, 7.90; N, 6.86; Found C, 61.73; H, 8.10; N, 7.14.

EXAMPLE 122

Together with 5 ml. of methanol and 2 ml. of concentrated hydrochloric acid, 0.3 g. of 5-acetoxymethyl-2-acetylamino-6-benzyloxy-1-hydroxy-1,2,3,4-tetrahydronaphthalene is heated on a boiling-water bath for 1 hour, after which time the solvent is distilled off. The residue is dissolved in a small amount of methanol and, following the addition of ethyl ether, the solution is allowed to stand, whereupon a colorless powdery product separate. This precipitate is recovered by filtration to obtain 0.05 g. of 2-amino-6-benzyloxy-1-hydroxy-5-hydroxymethyl-1,2,3,4-tetrahydronaphthalene hydrochloride.

EXAMPLE 123

In 5 ml. of methanol is dissolved 0.3 g. of 6-acetoxy-2-acetylamino-5-chloro-1-hydroxy-1,2,3,4-tetrahydronaphthalene and, with the addition of 1 ml. of hydrochloric acid, the solution is heated on a boiling water bath for 1.5 hours. The reaction mixture is concentrated to dryness under reduced pressure and ethyl acetate is added to the residue, whereupon the mixture gradually solidifies. The solidified product is recovered by filtration to obtain 0.15 g. of 2-amino-5-chloro-1,6-dihydroxy-1,2,3,4-tetrahydronaphthalene hydrochloride.

Elemental analysis; for $C_{10}H_8O_2N.HCl$; Calculated C, 57.02; H, 4.31; N, 6.65; Found C, 57.38; H, 4.14; N, 6.30.

EXAMPLE 124

In 40 ml. of ethanol is dissolved 0.4 g. of 6-benzyloxy-2-(2-cyclohexenylamino)-1-hydroxy-5-nitro-1,2,3,4-tetrahydronaphthalene hydrochloride and, with the addition of 0.4 g. of 5% palladium-on-carbon, catalytic reduction is carried out at atmospheric temperature and pressure. After the absorption of hydrogen has ceased, the catalyst is filtered off and the filtrate is concentrated under reduced pressure. The residue is dissolved in alcoholic hydrochloric acid and ethyl ether is added to the solution, whereupon 0.2 g. of 5-amino-2-cyclohexylamino-1,6-dihydroxy-1,2,3,4-tetrahydronaphthalene hydrochloride are crystallized. Melting point: 206°–209° C. Mixture-melting of this product with the product according to Example 86 shows no melting point depression.

EXAMPLE 125

To a solution of 0.5 g. of trans-2-(N-benzyl-N-methylamino)-6-benzyloxy-1-hydroxy-5-ureido-1,2,3,4-tetrahydronaphthalene in 10 ml. of ethanol are added 1ml. of alcoholic hydrochloric acid and 1.0 g. of 5% palladium-on-carbon, and catalytic reduction is carried out. After the stoichiometric amount of hydrogen has been absorbed, the catalyst is filtered off and the filtrate is concentrated under reduced pressure. The residue is dissolved in a mixture of methanol and acetone and the solution is allowed to stand. The procedure yields 0.15 g. of trans-1,6-dihydroxy-2-methylamino-5-ureido-1,2,3,4-tetrahydronaphthalene hydrochloride.

NMR spectrum (DMSO-$d_6$) δ : 4.60(1H,d,J=8.2Hz), 2.64 (3H,s)

EXAMPLE 126

To a solution of 0.4 g. of 6-benzyloxy-2-isopropylamino-5-nitro-1-hydroxy-1,2,3,4-tetrahydronaphthalene hydrochloride in 10 ml. of ethanol are added 1 ml. of concentrated hydrochloric acid and 0.4 g. of 5% palladium-on-carbon, and catalytic reduction is carried out. After the stoichiometric amount of hydrogen has been absorbed, the catalyst is filtered off and ethyl ether is added to the filtrate. The resulting crystals are recovered by filtration. The procedure yields 0.2 g. of 5-amino-1,6-dihydroxy-2-isopropylamino-1,2,3,4-tetrahydronaphthalene hydrochloride as colorless needles melting at 178°–182° C.

Elemental analysis; for $C_{13}H_{20}O_2N_2.2HCl.2H_2O$ Calculated C, 45.21; H, 7.59; N, 8.11; Found C, 45.38; H, 7.36; N, 7.86;

EXAMPLE 127

In 5 ml. of ethanol is dissolved 0.5 g. of 6-benzyloxy-1-hydroxy-2-isopropylamino-5-ureido-1,2,3,4-tetrahydronaphthalene, followed by catalytic reduction with 1 ml. of alcoholic hydrochloric acid and 0.5 g. of 5% palladium-on-carbon. After the stoichiometric amount of hydrogen has been absorbed, the catalyst is filtered off and the filtrate is concentrated under reduced pressure. The residue is then recrystallized from a mixture of ethanol and acetone. The procedure yields 0.2 g. of 1,6-dihydroxy-2-isopropylamino-5-ureido-1,2,3,4-tetrahydronaphthalene hydrochloride as colorless needles melting at 198°–200° C (decomp.).

Elemental analysis; for $C_{14}H_{21}O_3N_3.HCl$; Calculated C, 53.24; H, 7.02; N, 13.31; Found C, 53.01; H, 7.32; N, 13.44.

EXAMPLE 128

1.8 g. of 2-(N-benzyl-N-methylamino)-6-benzyloxy-1-hydroxy-5-nitro-1,2,3,4-tetrahydronaphthalene hydrochloride is neutralized with sodium bicarbonate and dissolved in 50 ml. of methanol. With the addition of 1.8 g. of 105 palladium-on-carbon, catalytic reduction is carried out at atmospheric temperature and pressure. After the stoichiometric amount of hydrogen has been absorbed, the catalyst is filtered off and an ethereal solution of fumaric acid is added to the filtrate. The mixture is allowed to stand. The procedure yields 0.7 g. of trans-5-amino-1,6-dihydroxy-2-methylamino-1,2,3,4-tetrahydronaphthalene fumarate as pale-brown needles melting above 300° C.

Elemental analysis; for $C_{11}H_{16}O_2N_2 \cdot C_4H_4O_4$; Calculated C, 55.55; H, 6.22; N, 8.64; Found C, 55.30; H, 6.14; N, 8.33.

NMR spectrum (DMSO-$d_6$) δ : 4.50(1H,d,J=8Hz), 2.52(3H,s)

EXAMPLE 129

0.3 g. of cis-5-(N-benzyl-N-methylamino)-6-benzyloxy-2-tert-butylamino-1-hydroxy-1,2,3,4-tetrahydronaphthalene oxalate is neutralized with sodium bicarbonate and dissolved in 10 ml. of methanol. With the addition of 0.3 g. of 10% palladium-on-carbon, catalytic reduction is carried out at atmospheric temperature and pressure. After the stoichiometric amount of hydrogen has been absorbed, the catalyst is filtered off and an ethereal solution of fumaric acid is added to the filtrate. The mixture is allowed to stand. The procedure yields 0.1 g. of cis-2-tert-butylamino-1,6-dihydroxy-5-methylamino-1,2,3,4-tetrahydronaphthalene fumarate as colorless needles melting at 195°–197° C.

Elemental analysis; for $C_{15}H_{24}O_2N_2 \cdot C_4H_4O_4$; Calculated C, 59.98; H, 7.44; N, 7.69; Found C, 60.13; H, 7.66; N, 7.63.

NMR(DMSO-$d_6$) δ : 2.64(3H,s), 4.60(1H,d,J=4Hz)

EXAMPLE 130

In a manner similar to that of Example 129, 1.0 g. of trans-5-(N-benzyl-N-methylamino)-6-benzyloxy-2-tert-butylamino-1-hydroxy-1,2,3,4-tetrahydronaphthalene oxalate is catalytically reduced to obtain 0.4 g. of trans-2-tert-butylamino-1,6-dihydroxy-5-methylamino-1,2,3,4-tetrahydronaphthalene fumarate as colorless needles melting at 205°–207° C.

Elemental analysis; for $C_{12}H_{24}O_2N_2 \cdot \frac{1}{2}C_4H_4O_4$; Calculated C, 63.33; H, 8.13; N, 8.69; Found C, 63.30; H, 8.09; N, 8.30.

NMR spectrum (DMSO-$d_6$) δ : 2.63(3H,s), 4.50(1H,d,J=8Hz)

EXAMPLE 131

In a manner similar to that described in Example 129, 0.6 g. of 5-(N-benzyl-N-methylamino)-6-benzyloxy-1-hydroxy-2-isopropylamino-1,2,3,4-tetrahydronaphthalene oxalate (mixture of isomers) is catalytically reduced to obtain 0.15 g. of trans-1,6-dihydroxy-2-isopropylamino-5-methylamino-1,2,3,4-tetrahydronaphthalene fumarate as colorless needles melting at 174°–176° C.

Elemental analysis; for $C_{14}H_{22}O_2N_2 \cdot C_4H_4O_4$; Calculated C, 59.00; H, 7.15; N, 7.65; Found C, 59.44; H, 7.16; N, 7.92.

NMR spectrum (DMSO-$d_6$) δ : 2.60(3H,s), 4.60(1H,d,J=9Hz)

EXAMPLES 132–133

The products listed in the table below are obtained by catalytically hydrogenating the corresponding trans-6-benzyloxy-5-(N-benzyl-N-methylamino)-1-hydroxy-2-substituted amino-1,2,3,4-tetrahydronaphthalenes and converting the resulting compounds to their fumarates, in manners similar to that of Example 129.

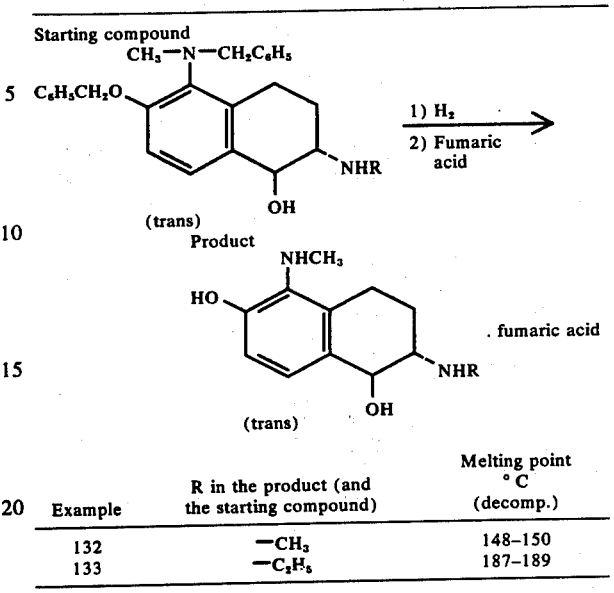

| Example | R in the product (and the starting compound) | Melting point °C (decomp.) |
|---|---|---|
| 132 | —CH$_3$ | 148–150 |
| 133 | —C$_2$H$_5$ | 187–189 |

EXAMPLE 134

0.7 g. of trans-5(N-benzyloxycarbonyl-N-methylamino)-6-benzyloxy-2-cyclobutylamino-1-hydroxy-1,2,3,4-tetrahydronaphthalene oxalate is dissolved in 20 ml. of water, and the solution is rendered alkaline with sodium bicarbonate and extracted with ethyl acetate. The extract is washed with water, dried and concentrated under reduced pressure. The residue is dissolved in 30 ml. of methanol, and catalytic reduction is carried out at atmospheric temperature and pressure in the presence of 0.7 g. of 10% palladium-on-carbon. After the stoichiometric amount of hydrogen has been absorbed, the catalyst is filtered off and an ethereal solution of fumaric acid is added to the filtrate. The filtrate is allowed to stand in the cold to obtain 0.2 g. of trans-2-cyclobutylamino-1,6-dihydroxy-5-methylamino-1,2,3,4-tetrahydronaphthalene fumarate as colorless needles melting at 196°–198° C (decomp.).

Elemental analysis; for $C_{15}H_{22}O_2N_2 \cdot \frac{1}{2}C_4H_4O_4 \cdot \frac{1}{2}H_2O$; Calculated C, 61.98; H, 7.65; N, 8.51; Found C, 62.00; H, 7.85; N, 8.28.

NMR spectrum (DMSO-$d_6$) δ : 4.70 (1H,d,J=8Hz)

EXAMPLE 135

3.4 g. of trans-6-benzyloxy-2-tert-butylamino-1-hydroxy-5-methoxycarbonyl-1,2,3,4-tetrahydronaphthalene O-sulfonate is suspended in a mixture of 300 ml. of water and 80 ml. of dioxane, and the mixture is stirred at 80° C for 15 hours. After cooling, the reaction mixture is rendered alkaline with an aqueous solution of sodium carbonate and extracted with ethyl acetate. The organic layer is dried and concentrated under reduced pressure. The residue is recrystallized from benzene-n-hexane to obtain 2.8 g. of cis-6-benzyloxy-2-tert-butylamino-1-hydroxy-5-methoxycarbonyl-1,2,3,4-tetrahydronaphthalene as colorless prisms melting at 104°–105° C.

NMR spectrum (CDCl$_3$) δ : 4.36 (1H,d,J=4Hz)

Elemental analysis; for $C_{23}H_{29}NO_4$; Calculated C, 72.03; H, 7.62; N, 3.65; Found C, 72.21; H, 7.96; N, 3.63.

EXAMPLE 136

1.0 g. of trans-6-benzyloxy-2-isopropylamino-1-hydroxy-5-methoxycarbonyl-1,2,3,4-tetrahydronaphthalene O-sulfonate is hydrolyzed in a manner similar to that of Example 135 to obtain 800 mg. of cis-6-benzyloxy-2-isopropylamino-1-hydroxy-5-methoxycarbonyl-1,2,3,4-tetrahydronaphthalene as white crystals, melting at 113°–114° C.

NMR spectrum (CDCl$_3$) δ : 4.49 (1H,d,J=3Hz)

Elemental analysis; for C$_{22}$H$_{27}$NO$_4$; Calculated C, 71.52; H, 7.37; N, 3.79; Found C, 71.89; H, 7.43; N, 3.47.

EXAMPLE 137

800 mg. of trans-1-acetoxy-6-benzyloxy-2-isopropylamino-5-methoxycarbonyl-1,2,3,4-tetrahydronaphthalene acetate is added to a solution of 1.0 g. of sodium hydroxide in 60 ml. of methanol, and the mixture is stirred at room temperature for 4 hours. The reaction mixture is concentrated to 10 ml. under reduced pressure and the concentrate is, following the addition of water, extracted with ethyl acetate. The organic layer is washed with water, dried and concentrated under reduced pressure. The residue is recrystalized from ethyl acetate-n-hexane to obtain 450 mg. of trans-6-benzyloxy-2-isopropylamino-1-hydroxy-5-methoxycarbonyl-1,2,3,4-tetrahydronaphthalene as crystals, melting at 91°–92° C. Mixture-melting of this product with that of Example 67 shows no melting-point depression.

EXAMPLE 138

To a solution of 1.0 g. of trans-1-acetoxy-2-acetylamino-6-benzyloxy-5-methoxycarbonyl-1,2,3,4-tetrahydronaphthalene in 20 ml. of tetrahydrofuran is added dropwise a suspension of 500 mg. of lithium alminum hydride in 50 ml. of tetrahydrofuran under a stream of nitrogen gas. After refluxing the mixture for 1 hour, another 300 mg. of lithium alminum hydride is added and the mixture is refluxed for 2 hours. After the excess lithium alminum hydride is decomposed by the addition of ethyl acetate, methanol, and then water, the mixture is extracted with ethyl acetate. The extract is washed with saturated aqueous sodium chloride, dried and evaporated under reduced pressure. The recrystallization of the residue from ethyl acetate yields 480 mg. of trans-6-benzyloxy-2-ethylamino-1-hydroxy-5-hydroxymethyl-1,2,3,4-tetrahydronaphthalene as colorless prisms melting at 158°–159° C.

Elemental analysis; for C$_{20}$H$_{25}$O$_3$N; Calculated C, 73.36; H, 7.70; N, 4.28; Found C, 73.34; H, 7.80; N, 4.05.

NMR spectrum (DMSO-d$_6$) δ : 4.18 (1H,d,J=8Hz)

EXAMPLE 139

Some examples of formulation in which the contemplated products of this invention are utilized, for example, as a bronchdilator are given below:

A. (Tablet)
(1) trans-1,6-dihydroxy-5-hydroxymethyl-2-isopropylamino-1,2,3,4-tetrahydronaphthalene      1.5 mg.
(2) lactose      90.0 mg.
(3) corn starch      38.0 mg.
(4) Magnesium stearate      0.5 mg.
      130.0 mg. per tablet After mixing (1), (2) and 26 mg. of corn starch thoroughly, the mixture is granulated with paste prepared from 7 mg. of corn starch. (4) and the remaining 5 mg. of corn starch are added to the granules and the mixture is compressed into a tablet of 7 mm. in diameter.

B. (Capsule)
(1) trans-2-cyclobutylamino-1,6-dihydroxy-5-hydroxymethyl-1,2,3,4-tetrahydronaphthalene acetate      0.5 mg.
(2) lactose      145.0 mg.
(3) microcrystalline cellulose      70.0 mg.
(4) magnesium stearate      4.5 mg.
      220.0 mg. per capsule All ingredients are thoroughly mixed and is filled into a hard gelatin capsule of size No. 3 (discribed in the Pharmacopoeia of Japan, eight edition).

C. (Injection)
(1) trans-1,6-dihydroxy-2-isopropylamino-5-methylamino-1,2,3,4-tetrahydronaphthalene fumarate      0.05 mg.
(2) sodium chloride      9 mg.
(3) chlorobutanol      5 mg.
(4) sodium bisulfite      1 mg.

All ingredients are dissolved in distilled water to make 1.0 ml. of the solution (pH 5.0). The solution is filled into an amber ampoule. The atmosphere in the ampoule is replaced with nitrogen gas. All the processes are conducted under sterile conditions.

D. (Inhalation)
(1) trans-2-tert-butylamino-1,6-dihydroxy-5-hydroxymethyl-1,2,3,4-tetrahydronaphthalene      0.25 g.
(2) glucose      5 g.

(1) and (2) are dissolved in sterilized distilled water to make 100.0 ml. of the solution, which is then filtered through a membrane filter having porosity of 0.22 micron.

E. (Aerosol for inhalation)
(1) trans-5-amino-1,6-dihydroxy-2-isopropylamino-1,2,3,4-tetrahydronaphthalene hydrochloride      0.25 g.
(2) corn oil      1 g.
(3) sorbitan triolete      0.5 g.
(4) Freon 12-Freon 11(50 W/W %: 50 W/W %) to make a total of 100 g.

In the mixture of (2) and (3), (1) is dispersed homogeneously to make the concentrate. The concentrate and the propellant (4) and then packaged into a metal container under elevated pressure.

What is claimed is:

1. A compound selected from the group consisting of compounds of the formula

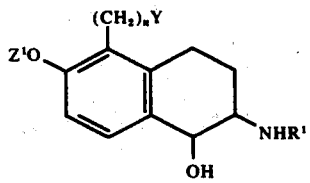

wherein $R^1$ is (1) hydrogen, (2) alkyl of up to 6 carbon atoms, (3) alkenyl of up to 6 carbon atoms, (4) alkynyl of up to 6 carbon atoms, said alkyl, alkenyl and alkynyl groups being unsubstituted or substituted by at least one of (a) cycloalkyl of 3–7 carbon atoms, (b) cycloalkenyl of 3–7 carbon atoms, (c) cycloalkylidene of 3–6 carbon atoms, (d) phenyl, (e) naphthyl, (f) hydroxyl, (g) alkoxy of 1–4 carbon atoms, (h) phenoxy, (i) naphthoxy, (j) halogen, (k) acetyl, (l) propionyl, (m) butyryl, (n) benzoyl, (o) unsubstituted amino and (p) nitro, said cycloalkyl, cycloalkenyl, phenyl and naphthyl groups being unsubstituted or substituted by at least one of (a) alkyl of 1–4 carbon atoms, (b) hydroxyl, (c) alkoxy of 1–4 carbon atoms and (d) halogen, (5) cycloalkyl of 3–7 carbon atoms, (6) cycloalkenyl of 3–7 carbon atoms, (7) phenyl, or (8) naphthyl, said last referred to cycloalkyl, cycloalkenyl, phenyl and naphthyl groups being unsubstituted or substituted or substituted by at least one of (a) alkyl of 1–4 carbn atoms, (b) hydroxyl, (c) alkoxy of 1–4 carbon atoms and (d) halogen, $OZ^1$ is unprotected hydroxyl or protected hydroxyl, Y is (1) hydrogen, (2) unprotected hydroxyl, (3) protected hydroxyl, (4) unsubstituted amino, (5) monoalkylamino of not more than 3 carbon atoms, (6) dialkylamino of not more than 3 carbon atoms in each alkyl group, (7) nitro or (8) halogen, n is zero, 1 or 2, with the proviso that when Y is hydrogen, uprotected hydroxyl or protected hydroxyl n is 1 or 2, and physiologically acceptable salts thereof.

2. A compound according to claim 1, wherein the salt is a physiologically acceptable acid addition salt.

3. A compound according to claim 1, wherein $-OZ^1$ is an unprotected hydroxyl.

4. A compound according to claim 1, wherein $-OZ^1$ is a protected hydroxyl.

5. A compound according to claim 4, wherein the protective group of the protected hydroxyl is aralkyl.

6. A compound according to claim 5, wherein the aralkyl is benzyl.

7. A compound according to claim 4, wherein the protective group of the protected hydroxyl is lower alkyl.

8. A compound according to claim 1, wherein Y is an unprotected hydroxyl and n is 1 or 2.

9. A compound according to claim 1, wherein Y is nitro or halogen and n is zero.

10. A compound according to claim 1, wherein $R^1$ is hydrogen.

11. A compound according to claim 1, wehrein $R^1$ is cycloalkyl of 3–7 carbon atoms which is unsubstituted or substituted by alkyl of 1–4 carbon atoms.

12. A compound according to claim 11, wherein the cycloalkyl is cyclobutyl.

13. A compound according to claim 1, which is in the form of a mixture of trans-and cis-isomers.

14. A compound according to claim 1, which is essentially in the form of a trans-isomer.

15. A compound according to claim 1, wherein U is an unprotected hydroxyl and n is 1.

16. A compound according to claim 1, wherein $R^1$ is alkyl of up to 6 carbon atoms substituted by phenyl, said phenyl being unsubstituted or substituted by hydroxyl or alkoxy of 1–4 carbon atoms.

17. A compound according to claim 16, wherein the $R^1$ alkyl is one having up to 4 carbon atoms.

18. A compound according to claim 16, wherein the $R^1$ alkyl is one ranching at its α-position.

19. A compound according to claim 1, wherein Y is unsubstituted amino, monoalkylamino of not more than 3 carbon atoms or dialkylamino of not more than 3 carbon atoms in each alkyl group.

20. A compound according to claim 1, wherein Y is unsubstituted amino, monoalkylamino of not more than 3 carbon atoms or dialkylamino of not more than 3 carbon atoms in each alkyl group, and n is zero.

21. A compound according to claim 20, wherein Y is unsubstituted amino.

22. A compound according to claim 20, whereis monoalkylamino of not more than 3 carbon atoms or dialky of not more than 3 carbon atoms in each alkyl group.

23. A compound according to claim 22, wherein is monoalkylamino of not more than 3 carbon atoms.

24. A compound according to claim 23, wherein the monoalkylamino is methylamino or ethylamino.

25. A compound according to claim 1, wherein $R^1$ is a group specified in claim 62 other than hydrogen.

26. A compound according to claim 25, wherein $R^1$ is alkyl of up to 6 carbon atoms, alkenyl of up to 6 carbon atoms or alkynyl of up to 6 carbon atoms, said alkyl, alkenyl and alkynyl groups being unsubstituted or substituted by at least one of cycloalkyl of 3–7 carbon atoms, cycloalkenyl of 3–7 carbon atoms, cycloalkylidene of 3–6 carbon atoms, phenyl, naphthyl, hydroxyl, alkoxy of 1–4 carbon atoms, phenoxy, naphthoxy, halogen, acetyl, propionyl, butyryl, benzoyl, unsubstituted amino and nitro, said cycloalkyl, cycloalkenyl, phenyl and naphthyl groups being unsubstituted or substituted by at least one of alkyl of 1–4 carbon atoms, hydroxyl, alkoxy of 1–4 carbon atoms and halogen.

27. A compound according to claim 26, wherein $R^1$ is alkyl of up to 6 carbon atoms, alkenyl of up to 6 carbon atoms or alkynyl of up to 6 carbon atoms, said alkyl, alkenyl and alkynyl groups being unsubsituted or substituted by at least one of cycloalkyl of 3–7 carbon atoms, phenyl or napthyl, said cycloalkyl, phenyl and naphthyl groups being unsubstituted or substituted by at least one of alkyl of 1–4 carbon atoms, hydroxyl, alkoxy of 1–4 carbon atoms and halogen.

28. A compound according to claim 26, wherein $R^1$ is the alkyl of up to 6 carbon atoms which may be substituted.

29. A compound according to claim 28, wherein the $R^1$ alkyl is one branching at its α-position.

30. A compound according to claim 25, wherein $R^1$ is cycloalkyl of 3–7 carbon atoms, cycloalkenyl of 3–7 carbon atoms, phenyl or naphthyl, said cycloalkyl, cycloalkenyl, phenyl and naphthyl groups being unsubstituted or substituted by at least one of alkyl of 1-4 carbon atoms, hydroxyl, alkoxy of 1-4 carbon atoms and halogen.

31. Trans-2-cyclobutylamino-1,6-dihydroxy-5-hydroxymethyl-1,2,3,4-tetrahydronaphthalene.
32. Trans-5-amino-2-cyclobutylamino-1,6-dihydroxy-1,2,3,4-tetrahydronaphthalene.
33. Trans-2-cyclobutylamino-1,6-dihydroxy-5-methylamino-1,2,3,4-tetrahydronaphthalene.
34. Trans-1,6-dihydroxy-5-hydroxymethyl-2-isopropylamino-1,2,3,4-tetrahydronaphthalene.
35. Trans-5-amino-1,6-dihydroxy-2-isopropylamino-1,2,3,4-tetrahydronaphthalene.
36. Trans-1,6-dihydroxy-2-isopropylamino-5-methylamino-1,2,3,4-tetrahydronaphthalene.
37. Trans-2-tert-butylamino-1,6-dihydroxy-5-hydroxymethyl-1,2,3,4-tetrahydronaphthalene.
38. 5-amino-2-tert-butylamino-1,6-dihydroxy-1,2,3,4-tetrahydronaphthalene.
39. Trans-2-tert-butylamino-1,6-dihydroxy-5-methylamino-1,2,3,4-tetrahydronaphthalene.
40. Trans-1,6-dihydroxy-5-hydroxymethyl-2-(α-methyl-p-hydroxyphenethylamino)-1,2,3,4-tetrahydronaphthalene.
41. 5-amino-1,6-dihydroxy-2-(α-methyl-p-hydroxyphenethylamino)-1,2,3,4-tetrahydronaphthalene.
42. Trans-1,6-dihydroxy-5-hydroxymethyl-2-(α-methyl-p-methoxyphenethylamino)-1,2,3,4-tetrahydronaphthalene.
43. Trans-5-amino-1,6-dihydroxy-2-(α-methyl-p-methoxyphenethylamino)-1,2,3,4-tetrahydronaphthalene.
44. Trans-1,6-dihydroxy-5-methylamino-2-(α-methyl-p-methoxyphenethylamino)-1,2,3,4-tetrahydronaphthalene.
45. Trans-2-cyclopentylamino-1,6-dihydroxy-5-hydroxymethyl-1,2,3,4-tetrahydronaphthalene.
46. Trans-5-ethylamino-1,6-dihydroxy-2-isopropylamino-1,2,3,4-tetrahydron phthalene.

47. A compound selected from the group consisting of compounds of the formula

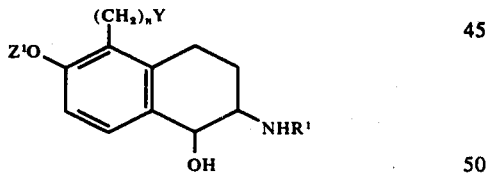

wherein
R$^1$ is alkyl of up to 6 carbon atoms, said alkyl being unsubstituted or substituted by phenyl, said phenyl being unsubstituted or substituted by hydroxyl or alkoxy of 1–4 carbon atoms, or R$^1$ is cycloalkyl of 3–7 carbon atoms,
OZ$^1$ is unprotected hydroxyl,
Y is unprotected hydroxyl, unsubstituted amino or monoalkylamino of not more than 3 carbon atoms,
n is zero when Y is unsubstituted amino or monoalkylamino of not more than 3 carbon atoms, and n is 1 when Y is unprotected hydroxyl,
and physiologically acceptable salts thereof.

48. A pharmaceutical composition which comprises
A. as active ingredient, at least one compound selected from the group consisting of compounds of the formula

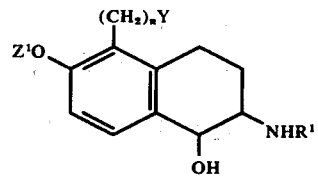

wherein R$^1$ is (1) hydrogen, (2) alkyl of up to 6 carbon atoms, (3) alkenyl of up to 6 carbon atoms, (4) alkynyl of up to 6 carbon atoms,
said alkyl, alkenyl and alkynyl groups being unsubstituted or substituted by at least one of (a) cycloalkyl of 3–7 carbon atoms, (b) cycloalkenyl of 3–7 carbon atoms, (c) cycloalkylidene of 3–6 carbon atoms, (d) phenyl, (e) naphthyl, (f) hydroxyl, (g) alkoxy of 1–4 carbon atoms, (h) phenoxy, (i) naphthoxy, (j) halogen, (k) acetyl, (l) propionyl, (m) butyryl, (n) benzoyl, (o) unsubstituted amino and (p) nitro,
said cycloalkyl, cycloalkenyl, phenyl and naphthyl groups being unsubstituted or substituted by at least one of (a) alkyl of 1–4 carbon atoms, (b) hydroxyl, (c) alkoxy of 1–4 carbon atoms and (d) halogen, (5) cycloalkyl of 3–7 carbon atoms, (6) cycloalkenyl of 3–7 carbon atoms, (7) phenyl, or (8) naphthyl,
said last referred to cycloalkyl, cycloalkenyl, phenyl and naphthyl groups being unsubstituted or substituted by at least one of (a) alkyl of 1–4 carbon atoms, (b) hydroxyl, (c) alkoxy of 1–4 carbon atoms and (d) halogen,
OZ$^1$ is unprotected hydroxyl or protected hydroxyl,
Y is (1) hydrogen, (2) unprotected hydroxyl, (3) protected hydroxyl, (4) unsubstituted amino, (5) monoalkylamino of not more than 3 carbon atoms, (6) dialkylamino of not more than 3 carbon atoms in each alkyl group, (7) nitro or (8) halogen,
n is zero, 1 or 2, with the proviso that when Y is hydrogen, unprotected hydroxyl or protected hydroxyl n is 1 or 2,
and physiologically acceptable salts thereof, and
B. a pharmaceutically acceptable carrier therefor.

49. A pharmaceutical composition which comprises
A. as active ingredient, at least one compound selected from the group consisting of compounds of the formula

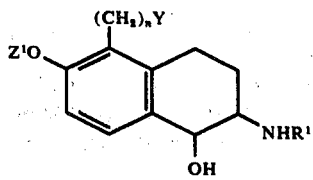

wherein R$^1$ is alkyl of up to 6 carbon atoms, said alkyl being unsubstituted or substituted by phenyl, said phenyl being unsubstituted or substituted by hydroxyl or alkoxy of 1–4 carbon atoms, or R$^1$ is cycloalkyl of 3–7 carbon atoms,
OZ$^1$ is unprotected hydroxyl,
Y is unprotected hydroxyl, unsubstituted amino or monoalkylamino of not more than 3 carbon atoms,
n is zero when Y is unsubstituted amino or monoalkylamino of not more than 3 carbon atoms, and n is 1 when Y is unprotected hydroxyl,
and physiologically acceptable salts thereof, and
B. a pharmaceutically acceptable carrier therefor.

* * * * *

UNITED STATES PATENT OFFICE
CERTIFICATE OF CORRECTION

Patent No. 4,035,512  Dated July 12, 1977

Inventor(s) Hirosada Sugihara, Masazumi Watanabe, Michio Motohashi, Masao Nishikawa and Yasushi Sanno It is certified that error appears in the above-identified patent and that said Letters Patent are hereby corrected as shown below:

In the heading of the Patent, insert the following information:

--[30] Foreign Application Priority Data

| June 12, 1974 | Japan . . . 67539/1974 |
| October 25, 1974 | Japan . . . 123539/1974 |
| November 29, 1974 | Japan . . . 137883/1974 |
| January 17, 1975 | Japan . . . 8148/1975 -- |

Column 3, line 27, change "acryclic" to --acyclic--.

Column 6, line 27, delete entirely.

Column 7, line 38, change "fluoroenylidene" to --fluorenylidene--.

Column 8, line 6, change "ordinary" to --ordinarily--.

Column 12, line 5, change "ascrobic" to --ascorbic--.

Column 14, change the structural formula in the brackets "[]" from

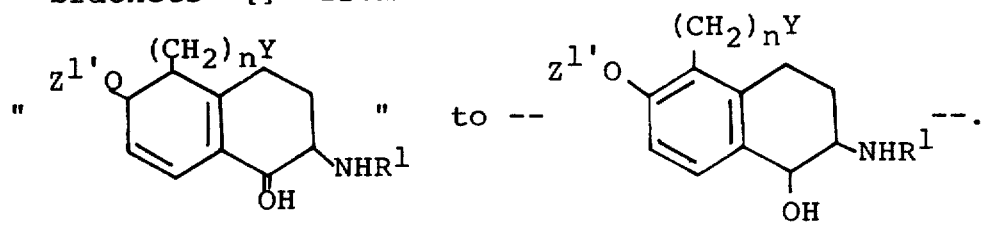

UNITED STATES PATENT OFFICE
CERTIFICATE OF CORRECTION

Patent No. 4,035,512     Dated July 12, 1977

Inventor(s) Hirosada Sugihara, et al.

It is certified that error appears in the above-identified patent and that said Letters Patent are hereby corrected as shown below:

Column 18, line 49, change "acrude" to --a crude--;

line 56, change "instances" to --instance--.

Column 19, line 30, change "1(2)-" to --1(2H)- --;

line 65, change "1(2)-nap-" to --1(2H)-naph- --;

line 66, change "thaalenone" to --thalenone--.

Column 20, line 17, change "Cin" to --C in--.

Column 21, line 16, change "3.34" to --3.32--.

Column 22, line 4, change "of" to --off--;

line 27, change "c" to --C--;

line 34, change "$(C_5H_5N \cdot NBr \cdot Br_2)$" to --$C_5H_5N \cdot HBr \cdot Br_2)$--.

Column 23, line 10, change "benzenethyl" to --benzene-ethyl--;

line 20, change "1(2)-" to --1(2H)- --;

line 59, rewrite to read --Elemental analysis; for $C_{21}H_{22}O_2N_2 \cdot HCl \cdot 1/2H_2O$; Cal- --;

UNITED STATES PATENT OFFICE
CERTIFICATE OF CORRECTION

Patent No. 4,035,512           Dated July 12, 1977

Inventor(s) Hirosada Sugihara, et al.

It is certified that error appears in the above-identified patent and that said Letters Patent are hereby corrected as shown below:

line 65, change "6-bemn-" to --6-ben- --.

Column 24, line 8, change "of" to --off--;

line 14, change "elemental" to --Elemental--;

line 34, change "tothose" to --to those--.

Column 26, line 11, change "(N-benzenyl" to --(N-benzyl--.

Column 27, line 9, change "$cm^{-1}$carbonyl)." to --$cm^{-1}$(carbonyl).--.

Column 28, line 7, after "4.0" insert --g.--.

Column 32, line 60, change "reflexed" to --refluxed--.

Column 33, line 49, change "235°14236°" to --235°-236°--;

line 64, change "etherpe-" to --ether-pe- --.

Column 34, line 19, change "Example" to --Examples--;

line 53, change "$\gamma$" to --$\delta$--.

Column 35, line 52, change "needless" to --needles--.

UNITED STATES PATENT OFFICE
CERTIFICATE OF CORRECTION

Patent No. 4,035,512    Dated    July 12, 1977

Inventor(s) Hirosada Sugihara, et al.

It is certified that error appears in the above-identified patent and that said Letters Patent are hereby corrected as shown below:

Column 36, line 16, change "-5-ben-" to -- -6-ben- --;

line 21, change "5.23" to --5.53--.

Column 37, line 37, change "NMR(CLCl$_3$)" to --NMR(CDCl$_3$)--.

Column 38, line 16, change "IR $\nu$ liq. max" to --IR $\nu_{liq.}^{max}$--.

Column 39, right-hand column corresponding to Reference Example 83, insert a comma (,) after "4.22:H,d";

right-hand column corresponding to Reference Example 83, change "=8Hz" to --J=8Hz--;

second column from the right corresponding to Reference Example 84, change "decomp.)" to --(decomp.)--;

second column from the right corresponding to Reference Example 85, change "175-179" to --175-178--;

second column from the right corresponding to Reference Example 88, change "142" to --142-144--.

Column 41, line 51, change "Example" to --Examples--;

line 54, change "methoxy-carbonyl" to --methoxycarbonyl--.

Column 44, line 10, change "or" to --of--.

UNITED STATES PATENT OFFICE
CERTIFICATE OF CORRECTION

Patent No. 4,035,512     Dated July 12, 1977

Inventor(s) Hirosada Sugihara, et al.

It is certified that error appears in the above-identified patent and that said Letters Patent are hereby corrected as shown below:

Column 45, line 6, change "acetoxy-methyl" to --acetoxymethyl--;

line 25, change "3,2-amino-3," to --3, 2-amino-6- --;

line 26, change "2-benzyloxy" to --benzyloxy--.

Column 46, line 47, change "5,46" to --5.46--.

Column 48, line 15, rewrite to read --hydroxyethyl)-2-isopropylamino-1,2,3,4-tetrahy- --.

Column 51, line 35, change "$C_{17}H_{26}O_2N_2 \cdot HCl$" to --$C_{17}H_{26}O_2N_2 \cdot 2HCl$";

line 60, change "naphthalene" to --naphthalenone--.

Column 52, line 16, change "46,58" to --46.58--.

Column 53, lines 10 and 28, change "catalystic" to --catalytic--;

line 51, change "6.9" to --6.96--;

line 62, after "water" insert --to--;

line 63, change "uble" to --ubles--.

UNITED STATES PATENT OFFICE
CERTIFICATE OF CORRECTION

Patent No. 4,035,512    Dated July 12, 1977

Inventor(s) Hirosada Sugihara, et al.

It is certified that error appears in the above-identified patent and that said Letters Patent are hereby corrected as shown below:

Column 54, line 32, change "400°C" to --40°C--;

line 54, change "m." to --ml.--.

Column 56, in the table, middle column, last formula, change

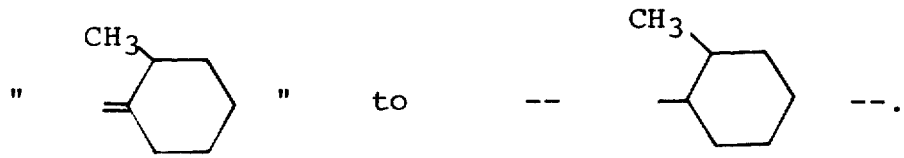

Column 58, line 10, change "234°C" to --235°C--;

line 21, change "5nitro" to --5-nitro--;

line 32, change "present" to --presence--.

Column 59, line 34, change "acetonebenzene=1:1)" to --acetone-benzene=1:1)--.

Column 60, in the table, right-hand column, first formula, change

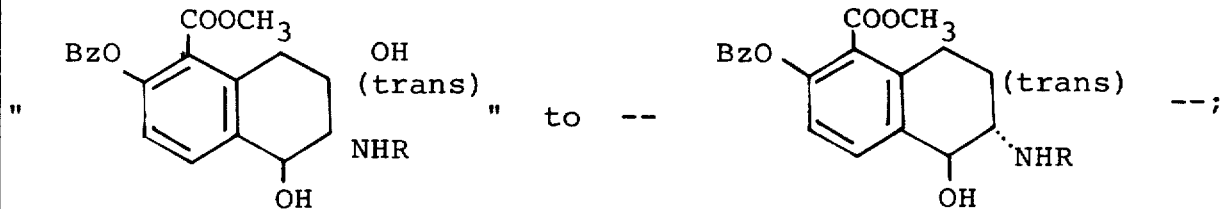

UNITED STATES PATENT OFFICE
CERTIFICATE OF CORRECTION

Patent No. 4,035,512            Dated July 12, 1977

Inventor(s) Hirosada Sugihara, et al.

It is certified that error appears in the above-identified patent and that said Letters Patent are hereby corrected as shown below:

Column 60, in the table, right-hand column, formula corresponding to Example 62, change

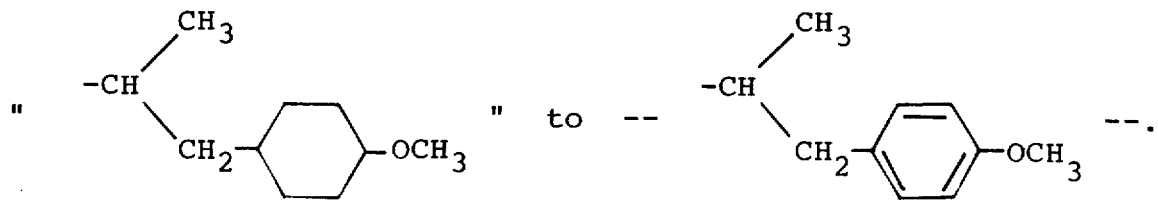

Column 61, in the table, second column from the right corresponding to Example 60, change "4.31(H,d,J=3Hz)" to --4.31(1H,d,J=8Hz)--;

Column 61, line 47, rewrite to read --benzyloxycarbonyl-N-methylamino)-6-benzyloxy-2- --.

Column 62, line 20, change "2isopropylamino" to --2-isopropylamino--;

line 54, change "MNR" to --NMR--.

Column 63, line 13, change "m ." to --ml.--.

Column 64, line 26, change "60,89" to --60.89--.

Column 65, line 15, change "0.51" to --0.5--;

line 53, insert a period (.) after "separates".

UNITED STATES PATENT OFFICE
CERTIFICATE OF CORRECTION

Patent No. 4,035,512        Dated July 12, 1977

Inventor(s) Hirosada Sugihara, et al.

It is certified that error appears in the above-identified patent and that said Letters Patent are hereby corrected as shown below:

Column 67, line 60, change "anthanol" to --ethanol--.

Column 68, line 26, change "ynethyl" to --ymethyl--.

Column 69, in the table, change the formula corresponding to Example 100 from

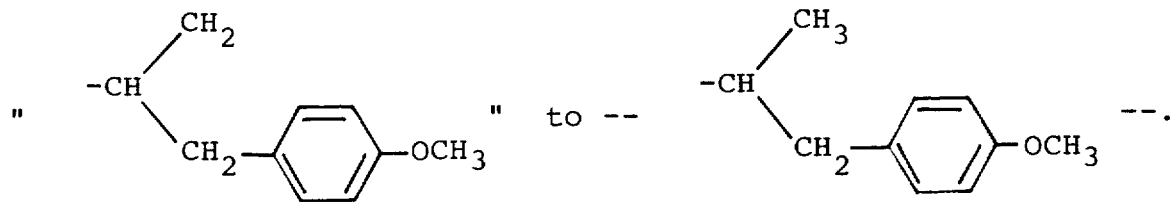

Column 75, line 40, change "separate" to --separates--.

Column 76, line 66, change "105" to --10%--.

Column 78, line 27, change "5(N" to --5-(N--.

Column 80, line 20, change "discribed" to --described--;

line 21, change "eight" to --eighth--.

Column 81, line 31, delete "or substituted";

line 64, change "wehrein" to --wherein--.

UNITED STATES PATENT OFFICE
CERTIFICATE OF CORRECTION

Patent No. 4,035,512            Dated July 12, 1977

Inventor(s) Hirosada Sughiara, et al.

It is certified that error appears in the above-identified patent and that said Letters Patent are hereby corrected as shown below:

Column 82, line 5, change "U" to --Y--;

line 14, change "ranching" to --branching--;

line 25, change "whereis" to --wherein Y is--;

line 27, change "dialky" to --dialkylamino--;

line 29, after "wherein" insert --Y--;

line 34, change "62" to --1--;

line 56, change "or" to --and--.

Column 83, line 40, change "tetrahydron phthalene" to --tetrahydronaphthalene--.

*Signed and Sealed this*

*Thirteenth* Day of *December 1977*

[SEAL]

Attest:

RUTH C. MASON        LUTRELLE F. PARKER
*Attesting Officer*      *Acting Commissioner of Patents and Trademarks*